US012622569B2

(12) United States Patent
Fujii et al.

(10) Patent No.: US 12,622,569 B2
(45) Date of Patent: May 12, 2026

(54) SURGICAL SYSTEM, PROCESSOR AND CONTROL METHOD

(71) Applicant: OLYMPUS CORPORATION, Tokyo (JP)

(72) Inventors: Masahiro Fujii, Tokyo (JP); Shiori Yasuda, Koganei (JP); Ryohei Ogawa, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 218 days.

(21) Appl. No.: 18/426,625

(22) Filed: Jan. 30, 2024

(65) Prior Publication Data

US 2025/0025018 A1      Jan. 23, 2025

Related U.S. Application Data

(60) Provisional application No. 63/527,837, filed on Jul. 20, 2023.

(51) Int. Cl.
*A61B 34/30* (2016.01)
*A61B 1/00* (2006.01)

(52) U.S. Cl.
CPC .... *A61B 1/000094* (2022.02); *A61B 1/00006* (2013.01); *A61B 1/000096* (2022.02); *A61B 1/00043* (2013.01)

(58) Field of Classification Search
CPC ... A61B 34/00; A61B 34/30; A61B 2034/301; A61B 17/3478; A61B 17/3403; A61B 1/00; A61B 1/000094; A61B 1/00006
See application file for complete search history.

(56) References Cited

U.S. PATENT DOCUMENTS

2015/0282749 A1* 10/2015 Zand .................... A61B 1/0676
600/301
2020/0281670 A1* 9/2020 Moskowitz ............ A61B 34/30
2022/0401166 A1* 12/2022 Hashimoto ............ G06N 20/20

FOREIGN PATENT DOCUMENTS

JP          2021-074242 A      5/2021

* cited by examiner

*Primary Examiner* — Vi X Nguyen
(74) *Attorney, Agent, or Firm* — Scully, Scott, Murphy & Presser, P.C.

(57)          ABSTRACT
A surgical system includes an endoscope including an imager which captures an endoscopic image, a medical manipulator with an injection needle at a distal end section thereof, a drive device which controls the medical manipulator to control a position of the injection needle, and a processor. The processor is configured to: control to inject a target amount of a injection fluid into a syringe connected to the injection needle; acquire, from the imager, the endoscopic image in which a treatment target is captured; and perform a prescribed determination to determine success/failure of injection using the endoscopic image, and control the drive device to change the position of the injection needle based on a determination result of the prescribed determination.

9 Claims, 50 Drawing Sheets

FIG.3
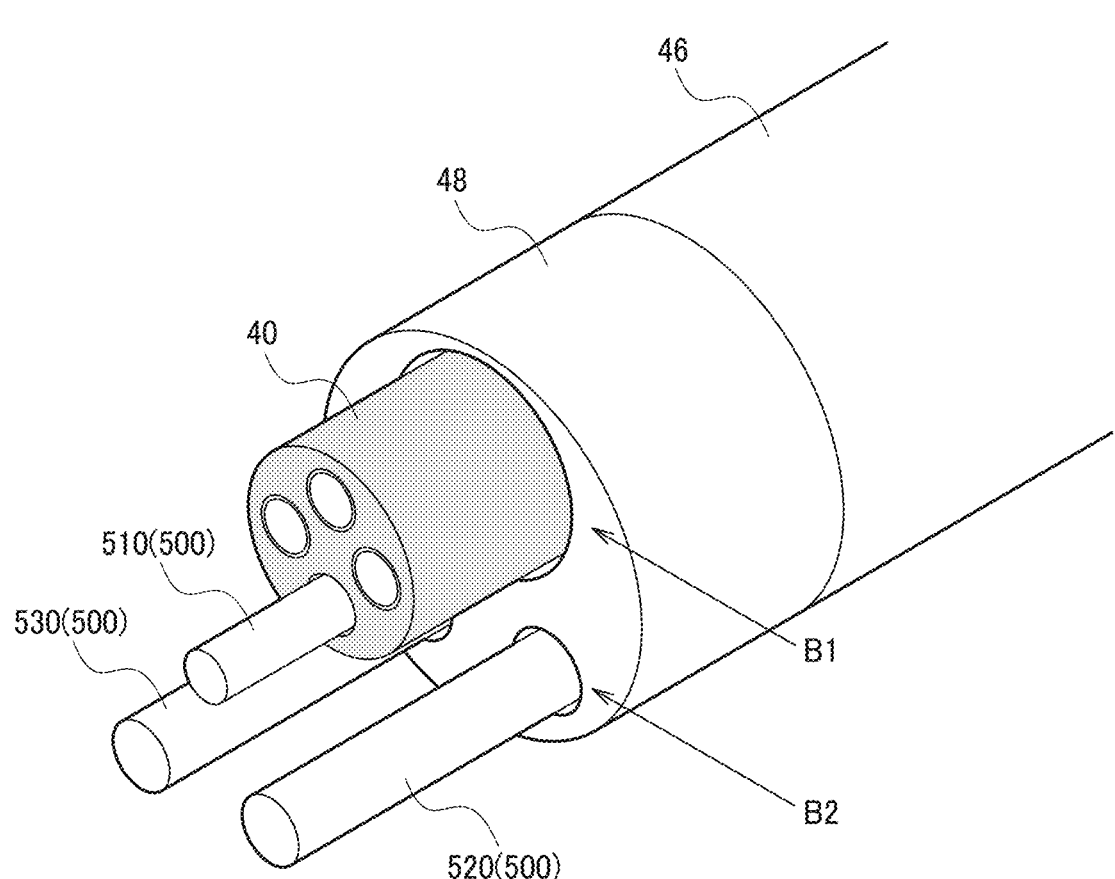
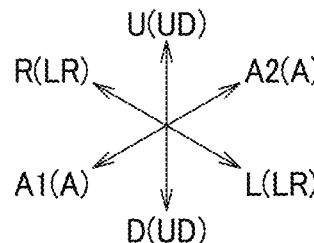

FIG.4
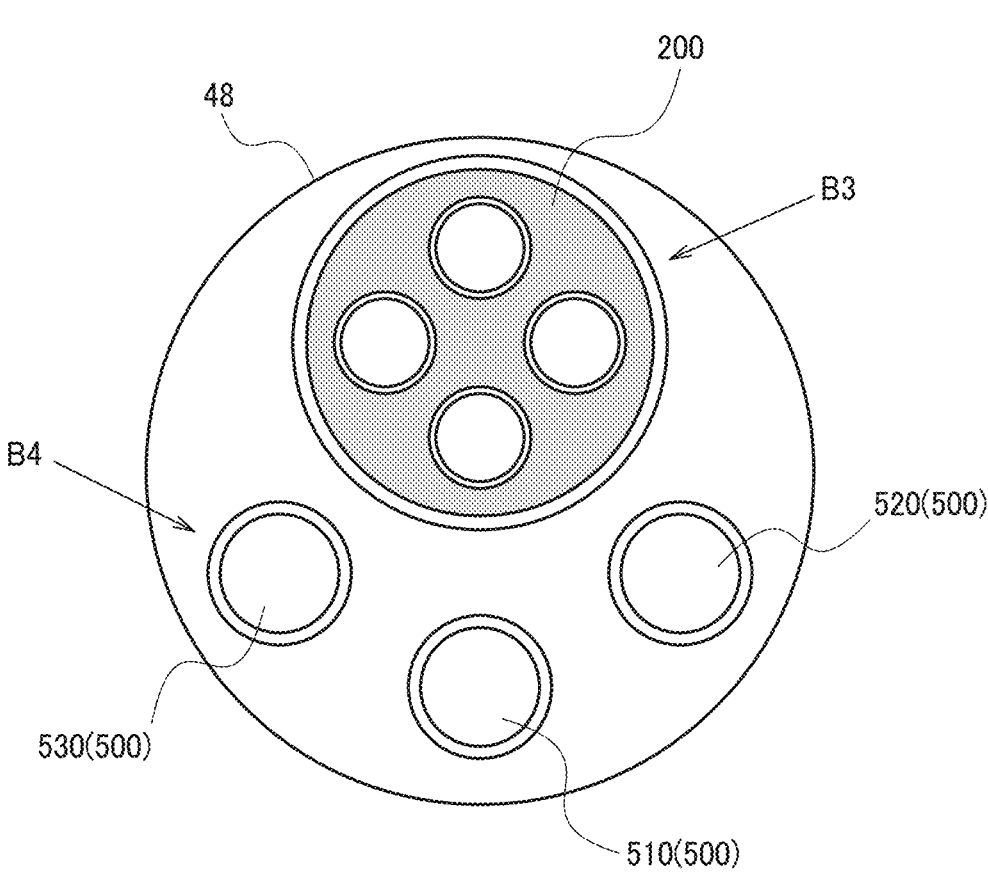
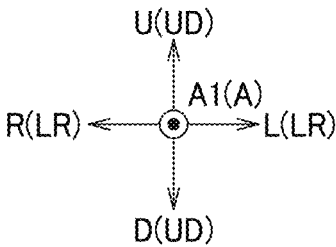

FIG.5
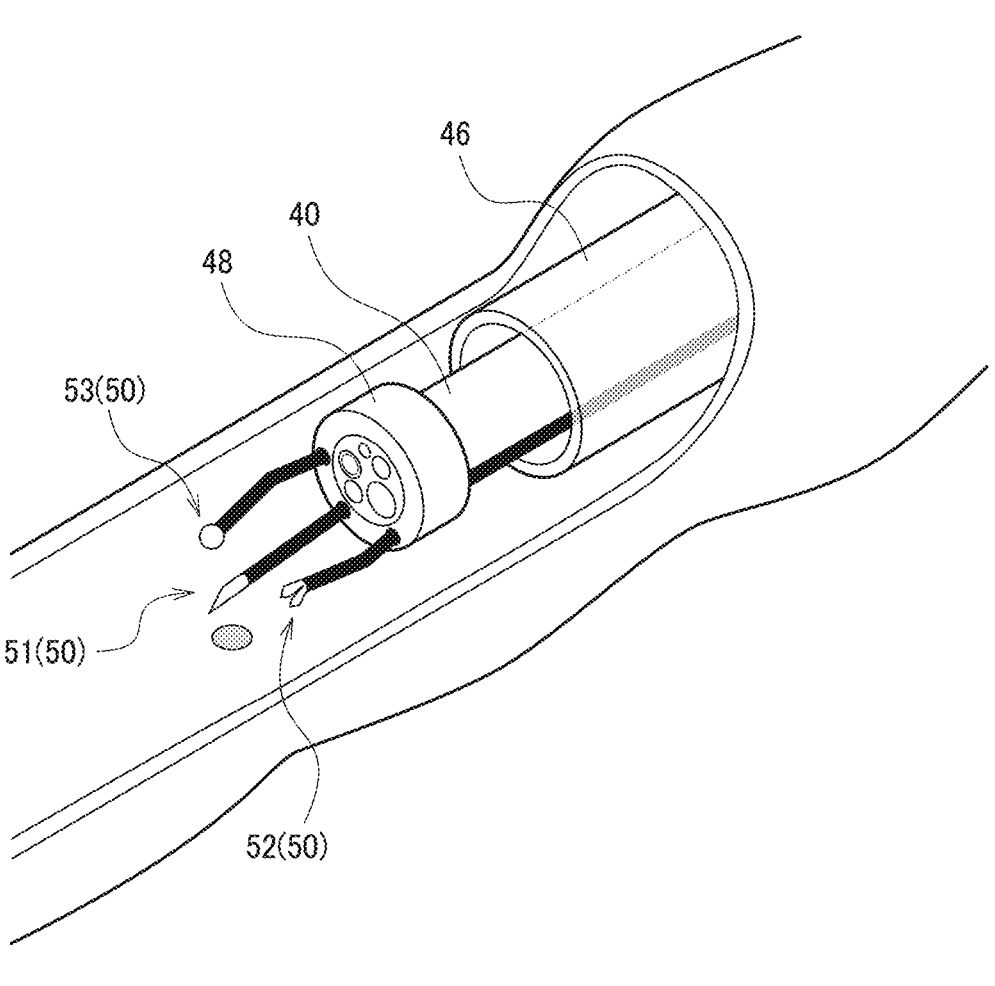
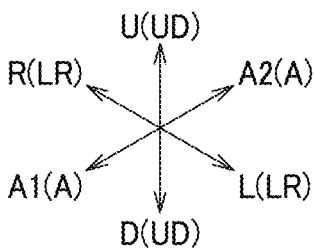

FIG.10

| OPERATED FOOT PEDAL | OPERATED HANDLE | DESTINATION OF CONTROL SIGNAL |
|---|---|---|
| FIRST FOOT PEDAL | FIRST HANDLE | THIRD TREATMENT TOOL DRIVE DEVICE |
| | SECOND HANDLE | SECOND TREATMENT TOOL DRIVE DEVICE |
| SECOND FOOT PEDAL | FIRST HANDLE | ENDOSCOPE DRIVE DEVICE |
| | SECOND HANDLE | — |
| THIRD FOOT PEDAL | FIRST HANDLE | FIRST TREATMENT TOOL DRIVE DEVICE |
| | SECOND HANDLE | — |

FIG.12

| OPERATED FOOT PEDAL | OPERATED HANDLE | | | ENABLEMENT/ DISABLEMENT OF RECEPTION OF CONTROL SIGNAL | |
|---|---|---|---|---|---|
| FIRST FOOT PEDAL | FIRST HANDLE | FIRST PART | FORWARD AND BACKWARD DIRECTION | ENABLED | B71 |
| | | | LEFT AND RIGHT DIRECTION | ENABLED | |
| | | SECOND PART | | ENABLED | |
| | | THIRD PART | | ENABLED | |
| | SECOND HANDLE | FIRST PART | FORWARD AND BACKWARD DIRECTION | ENABLED | B72 |
| | | | LEFT AND RIGHT DIRECTION | ENABLED | |
| | | SECOND PART | | ENABLED | |
| | | THIRD PART | | DISABLED | B73 |
| SECOND FOOT PEDAL | FIRST HANDLE | FIRST PART | FORWARD AND BACKWARD DIRECTION | ENABLED | B74 |
| | | | LEFT AND RIGHT DIRECTION | ENABLED | |
| | | SECOND PART | | ENABLED | |
| | | THIRD PART | | ENABLED | |
| | SECOND HANDLE | | | DISABLED | B75 |
| THIRD FOOT PEDAL | FIRST HANDLE | FIRST PART | FORWARD AND BACKWARD DIRECTION | ENABLED | B76 |
| | | | LEFT AND RIGHT DIRECTION | DISABLED | |
| | | SECOND PART | | DISABLED | |
| | | THIRD PART | | DISABLED | B77 |
| | SECOND HANDLE | | | DISABLED | |

FIG.20
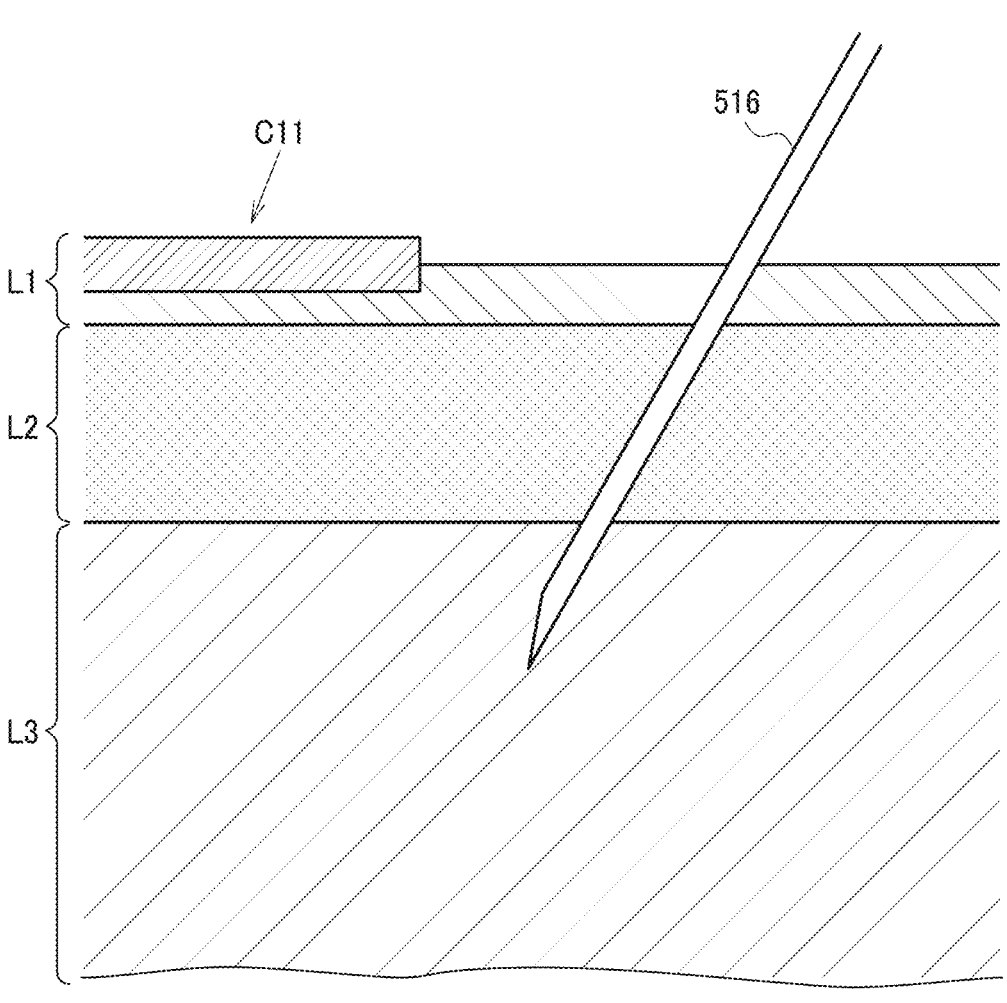
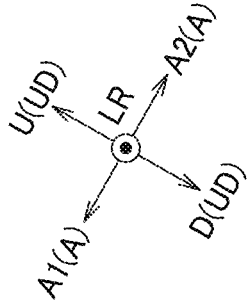

FIG.21
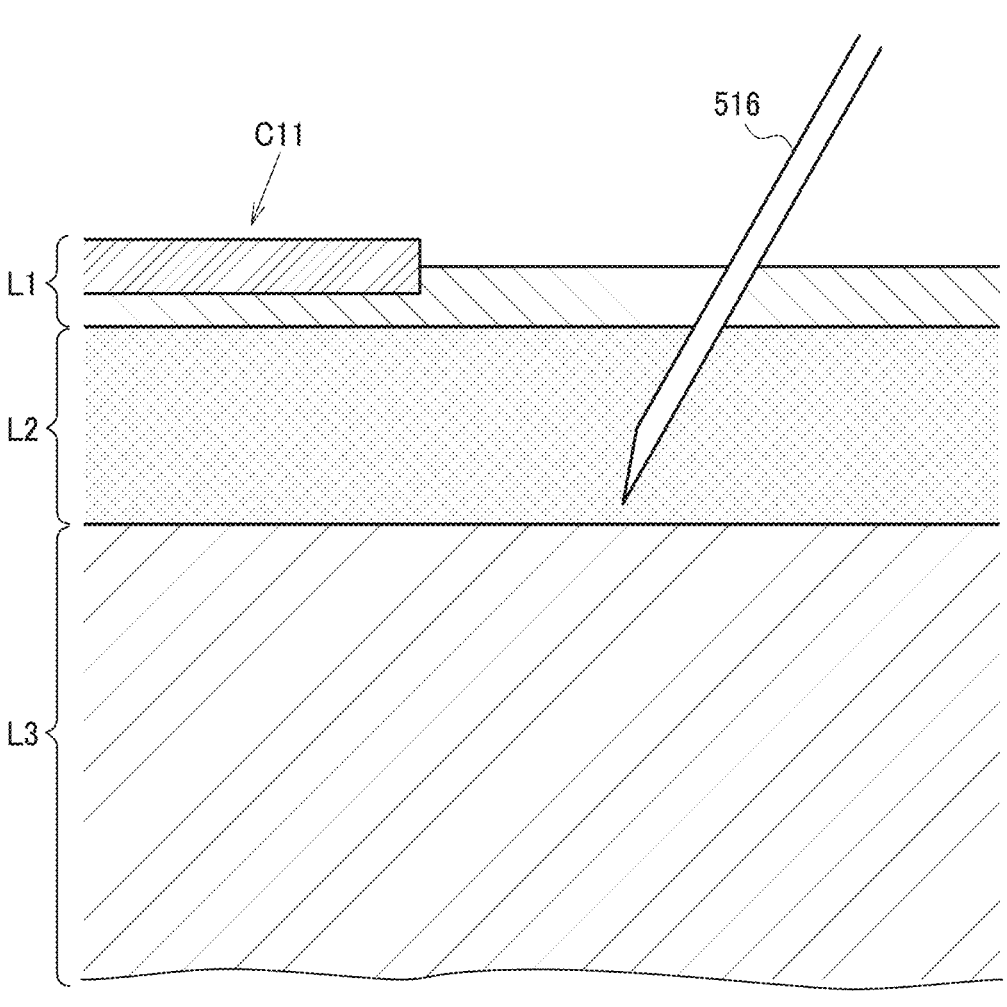
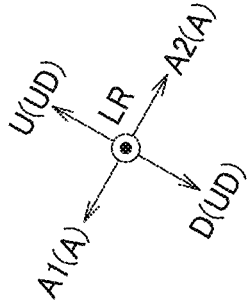

FIG.22
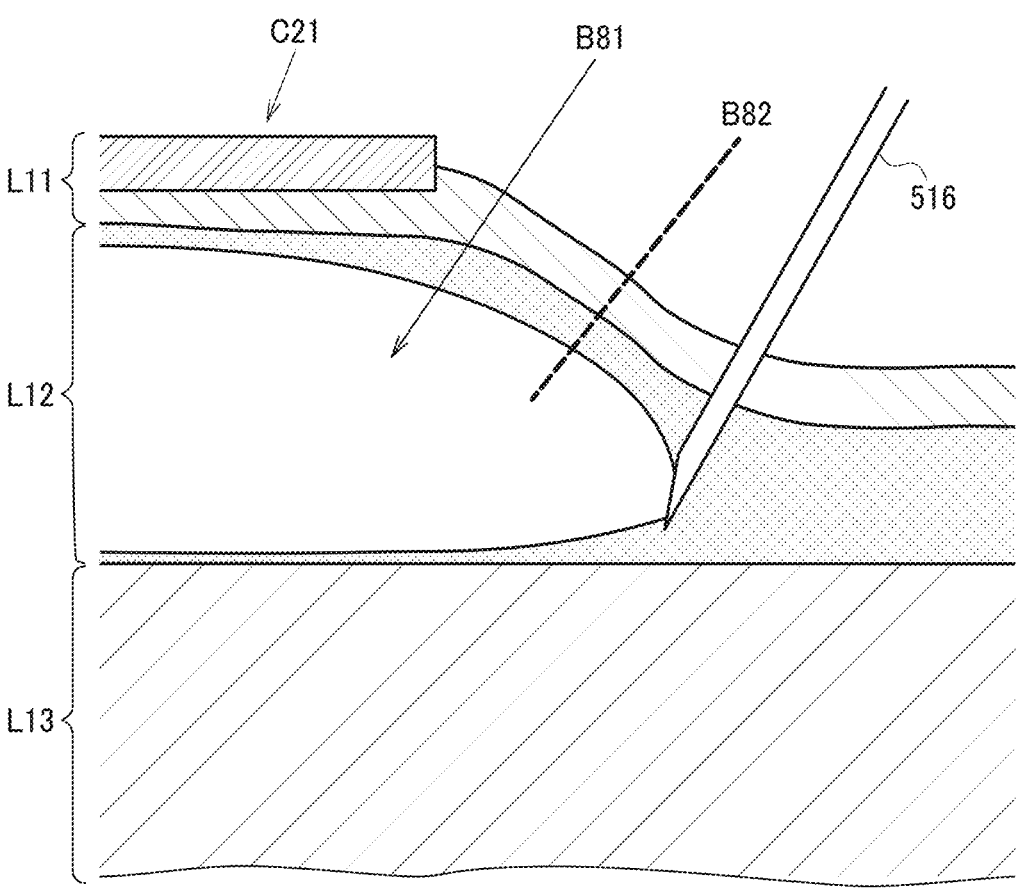
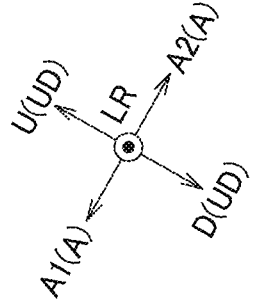

Figure 40:
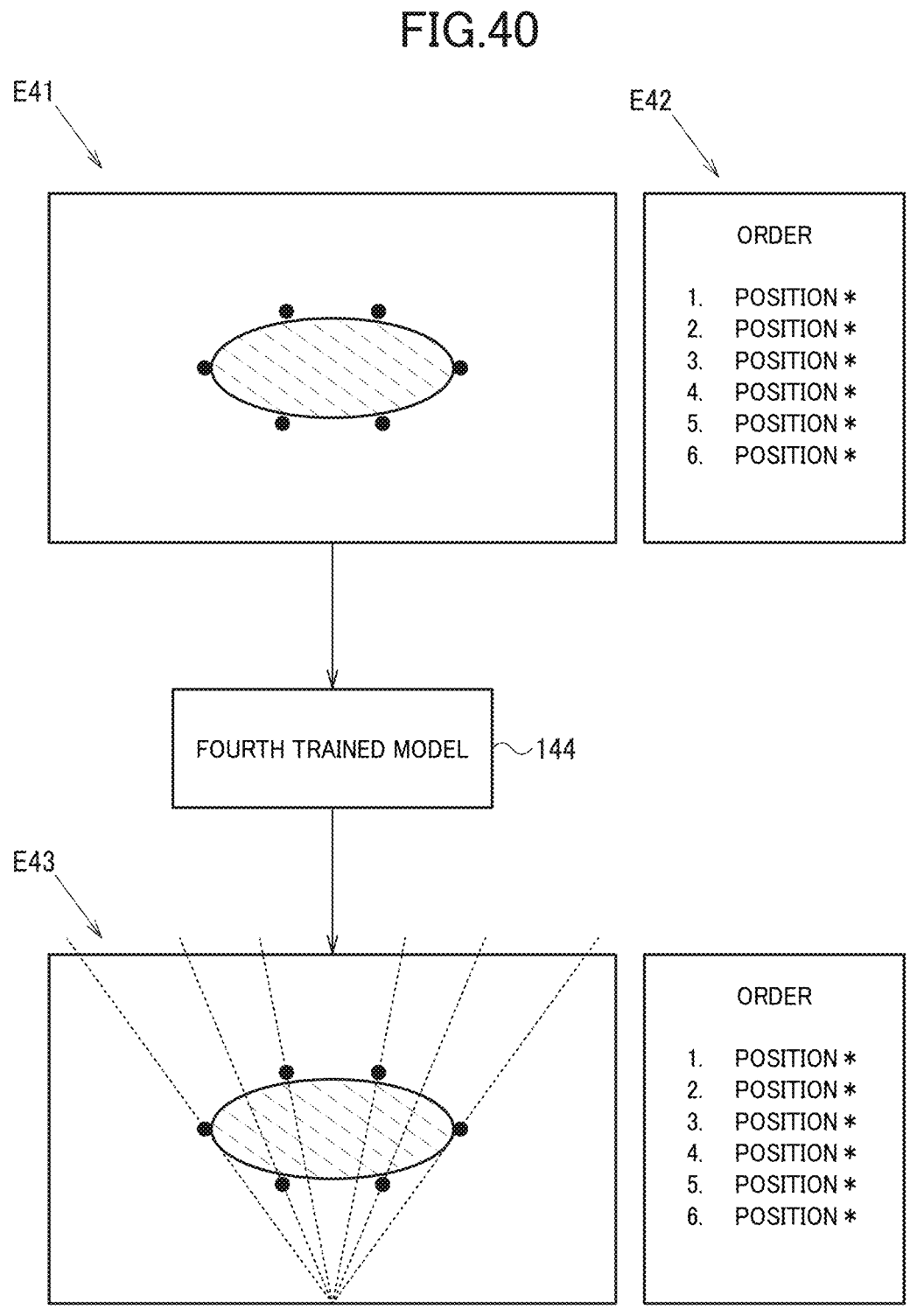

ORDER

1. POSITION *
2. POSITION *
3. POSITION *
4. POSITION *
5. POSITION *
6. POSITION *

FOURTH TRAINED MODEL ～144

E43

ORDER

1. POSITION *
2. POSITION *
3. POSITION *
4. POSITION *
5. POSITION *
6. POSITION *

Figure 43:
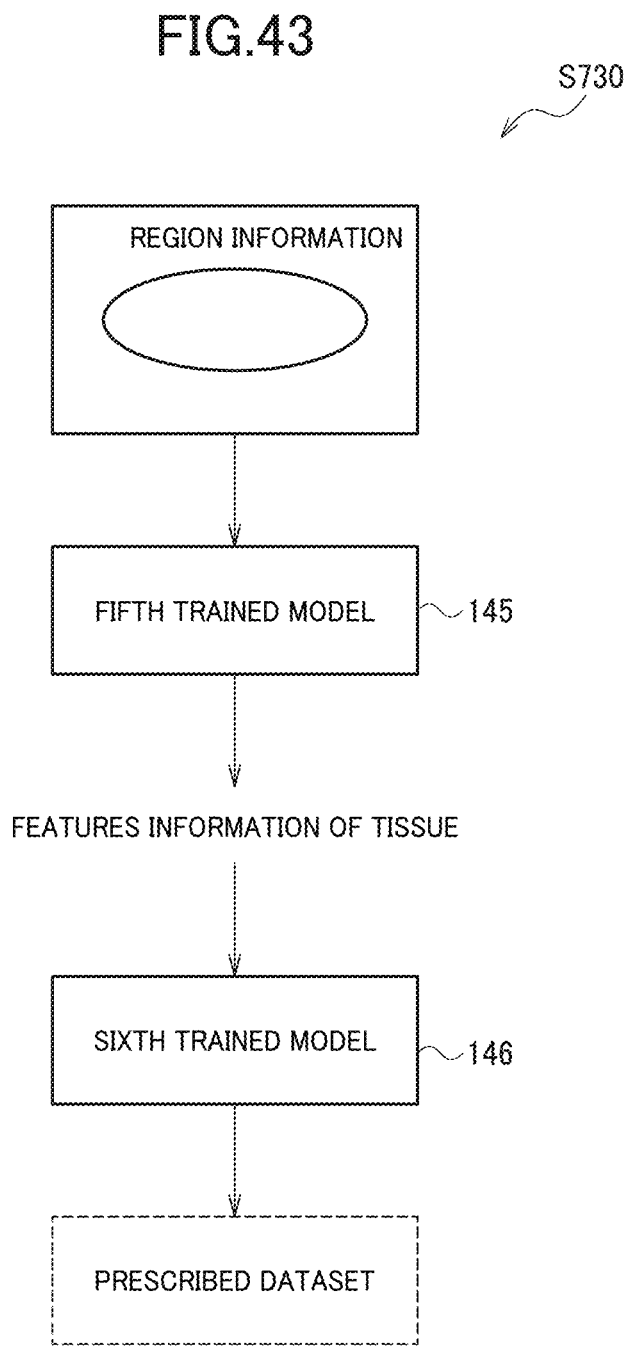

REGION INFORMATION

FIFTH TRAINED MODEL ~145

FEATURES INFORMATION OF TISSUE

SIXTH TRAINED MODEL ~146

PRESCRIBED DATASET

SURGICAL SYSTEM, PROCESSOR AND CONTROL METHOD

CROSS REFERENCE TO RELATED APPLICATIONS

This application is based upon and claims the benefit of priority to U.S. Provisional Patent Application No. 63/527, 837 filed on Jul. 20, 2023, the entire contents of which are incorporated herein by reference.

BACKGROUND OF THE INVENTION

A surgical system which controls a medical equipment such as an endoscope by a robot arm has been known. Japanese Unexamined Patent Application Publication No. 2021-074242 discloses a surgical system which automatically operates using machine learning.

SUMMARY OF THE INVENTION

In accordance with one of some aspect, there is provided a surgical system comprising:
an endoscope including an imager which captures an endoscopic image;
a medical manipulator with an injection needle at a distal end section thereof;
a drive device which controls the medical manipulator to control a position of the injection needle; and
a processor,
wherein the processor is configured to;
control to inject a target amount of a injection fluid into a syringe connected to the injection needle;
acquire, from the imager, the endoscopic image in which a treatment target is captured; and
perform a prescribed determination using the endoscopic image to determine success/failure of injection, and control the drive device to change the position of the injection needle based on a determination result of the prescribed determination.

In accordance with one of some aspect, there is provided a processor that controls an endoscope including an imager which captures an endoscopic image, and a drive device which controls a medical manipulator with an injection needle at a distal end section thereof to control a position of the injection needle,
wherein the processor is configured to:
control to inject a target amount of a injection fluid into a syringe connected to the injection needle;
acquire, from the imager, the endoscopic image in which a treatment target is captured; and
perform a prescribed determination to determine success/failure of injection using the endoscopic image, and control the drive device to change the position of the injection needle based on a determination result of the prescribed determination.

In accordance with one of some aspect, there is provided a control method for controlling an endoscope including an imager which captures an endoscopic image, and a drive device which controls a medical manipulator with an injection needle at a distal end section thereof to control a position of the injection needle,
the method comprising:
controlling to inject a target amount of a injection fluid into a syringe connected to the injection needle;
acquiring, from the imager, the endoscopic image in which a treatment target is captured; and performing a prescribed determination to determine success/failure of injection using the endoscopic image, and controlling the drive device to change the position of the injection needle based on a determination result of the prescribed determination.

BRIEF DESCRIPTION OF THE DRAWINGS

FIG. 3 is a diagram illustrating an example in which three treatment tool channels are included.
FIG. 4 is another diagram illustrating an example in which three treatment tool channels are included.
FIG. 5 is another diagram illustrating an example in which three treatment tool channels are included.
FIG. 10 is a diagram illustrating a drive device which is controlled by a foot pedal and a handle.
FIG. 12 is a diagram illustrating an example of setting for a control signal transmitted from a console.
FIG. 20 is a diagram illustrating an effect of the present embodiment.
FIG. 21 is another diagram illustrating an effect of the present embodiment.
FIG. 22 is another diagram illustrating an effect of the present embodiment.
FIG. 24 is another diagram illustrating an example configuration of a control device.

FIG. 40 is a diagram illustrating example data to be input to or output from a fourth trained model.

FIG. 43 is a diagram illustrating a technique for acquiring a prescribed dataset.

DETAILED DESCRIPTION

Figure 1:
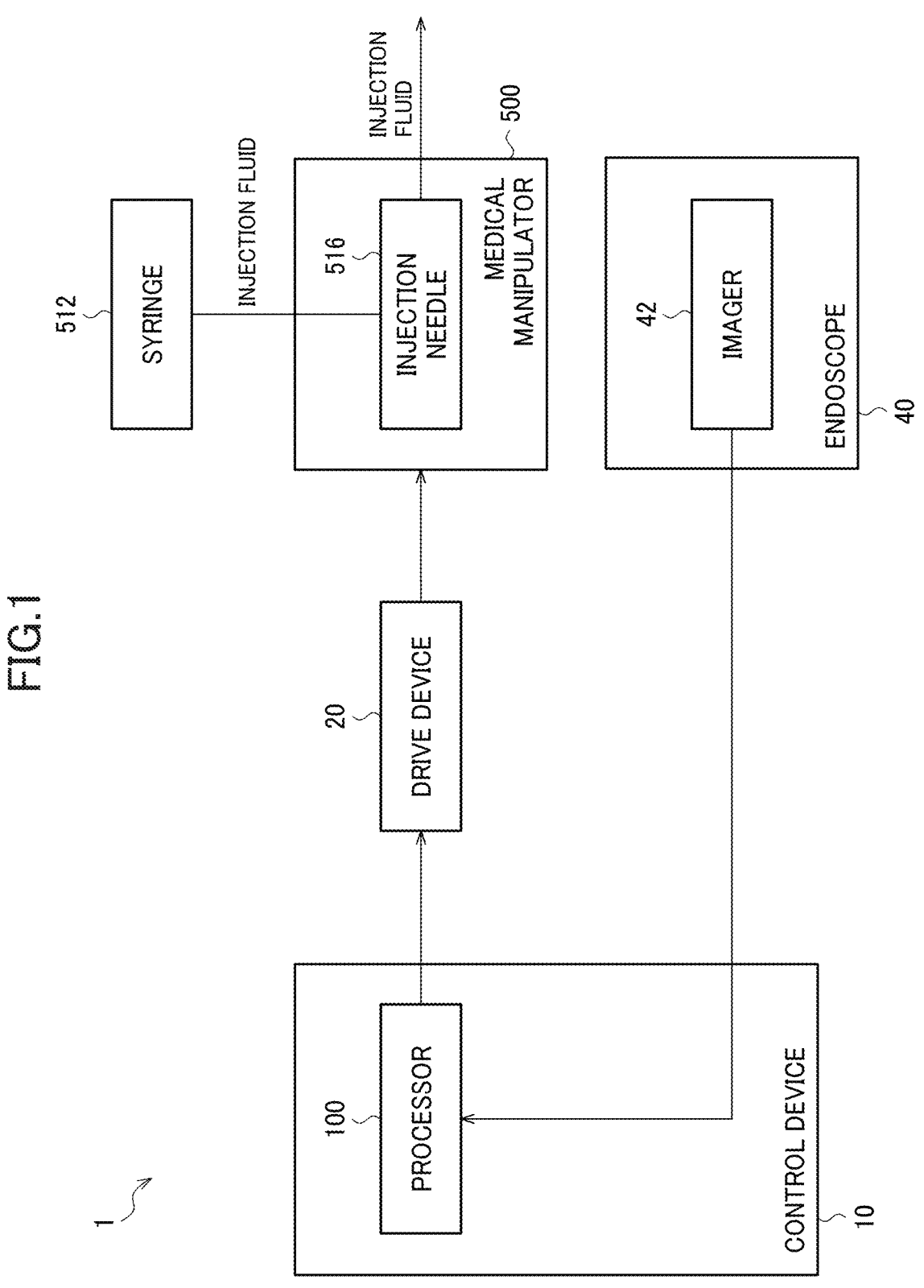
FIG. 1 is a block diagram illustrating an example configuration of a surgical system.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

An example configuration of a surgical system 1 of the present embodiment will be described with reference to FIG. 1. The surgical system 1 of the present embodiment includes a control device 10 including a processor 100, a drive device 20, and an endoscope 40. The control device 10 of the present embodiment controls the drive device 20. Further, while the drive device 20 of the present embodiment controls at least a medical manipulator 500, it may also control the endoscope 40 and the details will be described later with reference to FIG. 2.

The technique according to the surgical system 1 of the present embodiment is applicable to, for example, treatment of ESD (endoscopic submucosal dissection) as described below, and it shall not preclude the application to other treatment such as EMR (endoscopic mucosal resection), for example. In addition, a part of the technique described below may be applied to other treatment. Note that ESD stands for Endoscopic Submucosal Dissection, and EMR stands for Endoscopic Mucosal Resection. In the following description, the endoscope 40 of the present embodiment is illustrated as a flexible endoscope mainly used for ESD, but it shall not preclude the application of the technique of the present embodiment to other endoscopes such as a rigid endoscope. Furthermore, since well-known configurations as a flexible endoscope can widely be applied to each configuration of the endoscope 40 of the present embodiment, hereinafter the detailed illustration and description are omitted as appropriate.

The endoscope 40 of the present embodiment includes an imager 42. The imager 42 includes an imaging sensor which includes a CCD (Charge-Coupled Device) or CMOS (Complementary Metal-Oxide-Semiconductor) sensor and the like, an optical member and the like, and functions as an imaging device. In the present embodiment, an image captured by the imager 42 is referred to as an endoscopic image, and the imager 42 captures an image of returning light from a subject irradiated by an illumination device (not shown), thereby outputting an image signal to the processor 100 of the control device 10 via a cable and the like (not shown). The processor 100 generates a display image based on the image signal, and outputs the display image to, for example, a display 610 and the like described later with reference to FIG. 9, etc. Note that the image signal includes a video signal, and an endoscopic image may be a still image of video generated based on the video signal. Further, the imager 42 of the present embodiment may be a 3D camera. As such, the processor 100 can acquire a stereoscopic image as the endoscopic image. Note that in this case, the display 610 and the like may support stereoscopic images. The display 610 and the like supporting stereoscopic images means that hardware of the display 610 is configured such that a user can recognize a stereoscopic effect of the endoscopic image displayed on the display 610. Further, the fact that a user can recognize a stereoscopic effect of the endoscopic image displayed on the display 610 is, for example, not limited to a case that the user can recognize the stereoscopic effect of the endoscopic image when looking at the display 610 with naked eyes, but also includes, for example, a case that the user can recognize the stereoscopic effect of the endoscopic image when looking at the display 610 through dedicated goggles and the like. Note that in the following description, though a practitioner who operates a console 60 described later with reference to FIG. 8, etc. is uniformly referred to as a user, an assistant who assists operations by the practitioner, for example, may be referred to as a user. Specifically, the assistant is, for example, the one who inserts the endoscope 40 into a subject, the one who replaces a treatment tool 50 described later, and the like. Note that, as described later, there may be a plurality of treatment tools 50, which may specifically be referred to as a first treatment tool 51, a second treatment tool 52, a third treatment tool 53 and the like as necessary. In addition, the illumination device (not shown) may have a plurality of illumination modes, for example. For instance, a plurality of types of filters that control the illumination device to transmit light of desired wavelengths are included, and the control device 10 performs a process of selecting the filter according to the situation as appropriate so that light transmitted through the filter is irradiated to a subject. This allows a user to smoothly perform treatment. Note that there are many known techniques proposed for the illumination modes and thus, the detailed description thereof is omitted.

The processor 100 of the present embodiment is configured with the below hardware. The hardware can include at least one of a circuit that processes digital signals and a circuit that processes analog signals. For example, the hardware can be configured with one or more circuit devices or one or more circuit elements mounted on a circuit board. The one or more circuit devices are, for example, an IC (Integrated Circuit) and the like. The one or more circuit elements are, for example, a resistor, a capacitor, and the like.

Furthermore, for example, the processor 100 of the present embodiment can operate based on a memory 130 (not shown in FIG. 1) and information stored in the memory 130. The information is, for example, such as a program and various data. Note that the program may include, for example, a first trained model 141 and the like described later with reference to FIG. 24. The processor 100 can use a CPU (Central Processing Unit), a GPU (Graphics Processing Unit), a DSP (Digital Signal Processor), and the like. The memory 130 may be a semiconductor memory such as a SRAM (Static Random Access Memory) and a DRAM (Dynamic Random Access Memory), or a register, or a magnetic storage device such as a hard disk device, or an optical storage device such as an optical disk device. For example, the memory 130 stores computer-readable instructions, which are executed by the processor 100 to cause functions of each section of the control device 10 to be implemented as processing. The instructions as referred to herein may be a set of instructions configuring the program, or the instructions instructing the hardware circuit of the processor 100 to operate. Further, the memory 130 is also referred to as a storage device.

The medical manipulator 500 includes at least an injection needle 516. Note that while the details will be described later with reference to FIG. 2, there may be a plurality of medical manipulators 500, which may be specifically referred to as a first medical manipulator 510, a second medical manipulator 520, a third medical manipulator 530, and the like as necessary. The injection needle 516 is used for injecting, for example, a injection fluid filled in a syringe 512, into a submucosal layer described later. The injection fluid is, for example, normal saline and the like, and may contain sodium hyaluronate of a prescribed ratio and the like. This can increase viscosity of the injection fluid. This can maintain a state in which a mucosa is raised high, as described later in detail with reference to FIG. 22. This can minimize damage to a muscle layer by incision (step S610) and the like described later with reference to FIG. 14, etc. This can reduce possibility of occurrence of complications due to the damage to the muscle layer. Further, the injection fluid may contain a predetermined pigment substance. The predetermined pigment substance is, for example, indigo carmine and the like. In this way, a submucosal layer which received injection becomes bluish transparent so that a user can easily determine a region suitable for the incision (step S610) as described later.

Figure 2:
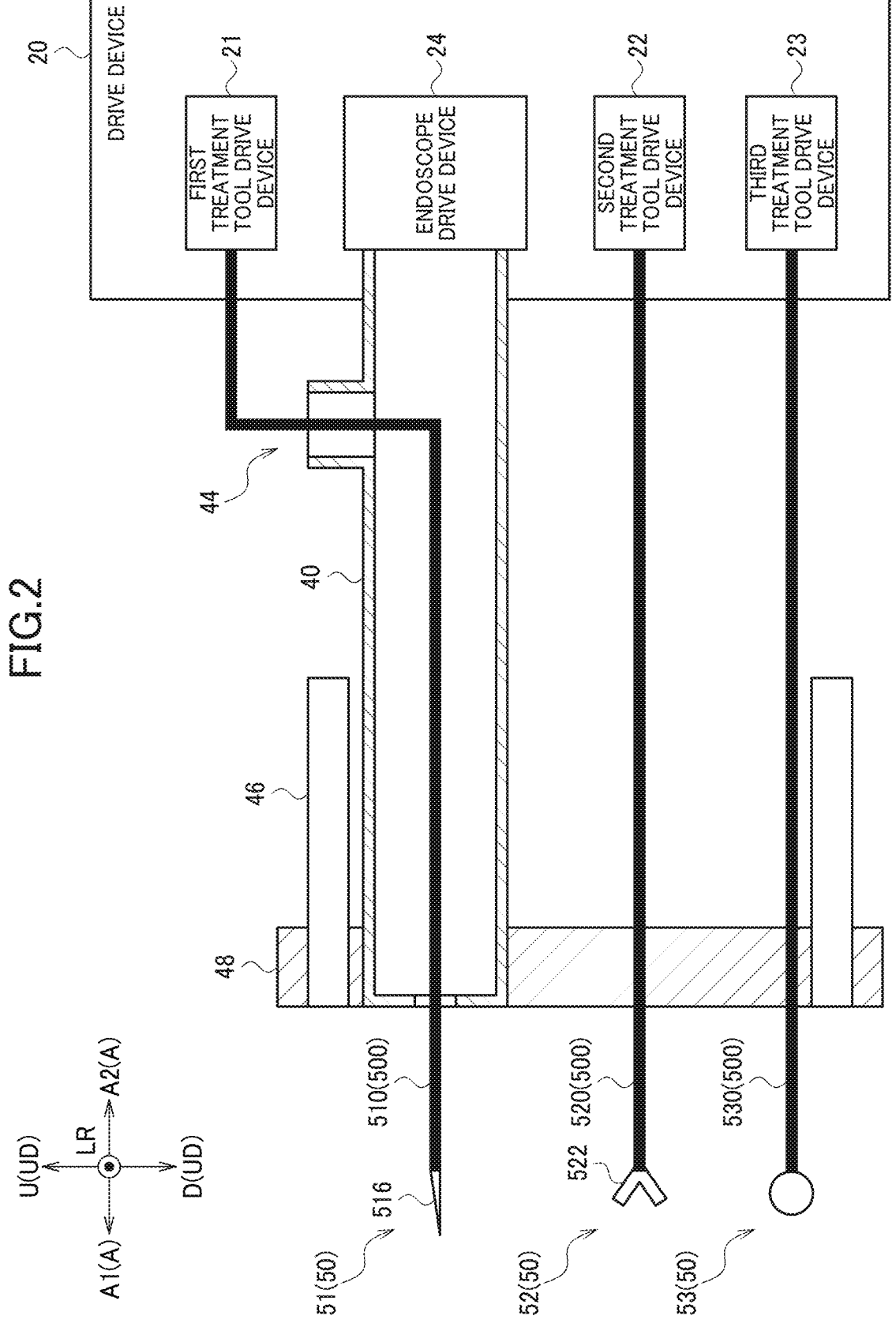
FIG. 2 is a diagram illustrating an example configuration of a drive device.

The drive device 20 of the present embodiment will be described. The drive device 20 of the present embodiment can be configured as illustrated in FIG. 2, for example. The drive device 20 includes a first treatment tool drive device 21 which controls each section of the first treatment tool 51, a second treatment tool drive device 22 which controls each section of the second treatment tool 52, a third treatment tool drive device 23 which controls each section of the third treatment tool 53, and an endoscope drive device 24 which controls each section of the endoscope 40. Note that FIG. 2 is a conceptual diagram, and a part of the configuration such as the imager 42 and the syringe 512 is omitted in the figure for convenience of explanation. The same applies to FIGS. 16 and 17 described later.

Further, for convenience of explanation, an axis A, an axis UD, and an axis LR are illustrated as three axes orthogonal to each other in FIG. 2 and the subsequent figures as appropriate. A direction of the axis A is parallel to a direction along a longitudinal direction of the medical manipulator 500, with respect to a distal end section, which is a distal end of an insertion section of the endoscope 40. Further, a direction in which the medical manipulator 500 moves forward is the direction A1, and a direction in which the medical manipulator 500 moves backward is the direction A2. Note that in the following description, moving forward or moving backward may be simply referred to as "advance/retreat". In other words, the direction of the axis A is a direction along which the medical manipulator 500 advances/retreats. In addition, a direction along the axis UD is referred to as an axis UD direction and a direction along the axis LR is referred to as an axis LR direction.

The first treatment tool 51 is, for example, a injection needle. In this case, the first treatment tool 51 includes, for example, the first medical manipulator 510 and the injection needle 516 located at a distal end of the first medical manipulator 510. That is, the medical manipulator 500 in FIG. 1 corresponds to the first medical manipulator 510 in FIG. 2.

The second treatment tool 52 is, for example, grasping forceps. In this case, the second treatment tool 52 includes, for example, the second medical manipulator 520 and a grasping section 522 located at a distal end of the second medical manipulator 520.

Further, the third treatment tool 53 is, for example, an electrosurgical knife. In this case, the third treatment tool 53 includes, for example, the third medical manipulator 530. In the third treatment tool 53, a knife section is configured to protrude from a distal end of the third medical manipulator 530. The knife section includes a power feeding wire, a high frequency electrode and the like (not shown). For example, a high frequency current is applied to the high frequency electrode from a power feeding device (not shown) via the power feeding wire. By bringing the high frequency electrode into contact with a desired biological tissue in this state, the biological tissue is cauterized by thermal energy generated from the high frequency electrode. By controlling the thermal energy and the like, marking, incision (step S610), hemostasis, or the like as described later are performed. Note that a shape of the knife section illustrated in FIG. 2, etc. is pole-type, but not limited thereto and may be scalpel-type, needle-type, hook-type, scissors-type, tweezers-type, and the like. In other words, known configurations of a high frequency treatment tool can widely be applied to a distal end of the third treatment tool 53 of the present embodiment.

In the surgical system 1 of the present embodiment, at least the first treatment tool 51 is electrically controlled by the technique described later. Note that at least one of the second treatment tool 52, the third treatment tool 53, and the endoscope 40 may also be electrically controlled. Provided in the following description is an example in which all the second treatment tool 52, the third treatment tool 53, and the endoscope 40 are electrically controlled. In addition, something electrically done means that the medical manipulator 500 is driven by an actuator such as a motor based on an electrical signal for controlling operations of the medical manipulator 500 and the like. Further, the medical manipulator 500 and the like being electrically driven includes a case that the medical manipulator 500 and the like are electrically driven based on determination by the processor 100, as well as a case that the medical manipulator 500 and the like are electrically driven by manual operation of the console 60 described later by a user.

By electrically controlling the first treatment tool 51 and the like in this manner, a injection process (step S500) described later can be implemented, and steps associated with injection for ESD can be performed by automatic control of the first treatment tool 51. The automatic control of the first treatment tool 51 refers to a case that the processor 100, rather than a user, makes determination to control each section included in the first treatment tool 51 and the like, that is, the processor 100 controls each section included in the first treatment tool 51 and the like using a predetermined control algorithm.

In this manner, in the surgical system 1 of the present embodiment, the first treatment tool 51, the second treatment tool 52, and the third treatment tool 53 are inserted, together with the endoscope 40, into a body to perform each treatment associated with ESD, but the endoscope 40 need not have three treatment tool channels. For example, the surgical system 1 of the present embodiment may further include an overtube 46. Further, the overtube 46 may be configured to have a plurality of treatment tool channels inside thereof. For example, as shown in FIG. 2, the endoscope 40 has one treatment tool insertion hole 44, where the first treatment tool 51 is inserted into the treatment tool insertion hole 44 whereas the second treatment tool 52 and the third treatment tool 53 are respectively inserted into two treatment tool channels in the overtube 46.

Further, as shown in FIG. 2, the surgical system 1 of the present embodiment may further include a cap 48. While various known shapes of the cap 48 have been proposed, the cap 48 includes, for example, an endoscope outlet hole indicated by B1 and a treatment tool outlet hole indicated by B2 as shown in FIG. 3. In the cap 48 in FIG. 3, one endoscope outlet hole and two treatment tool outlet holes are formed in correspondence with the example shown in FIG. 2. That is, as shown in FIG. 3, the first medical manipulator 510 is protruded from the endoscope outlet hole indicated by B1, whereas the second medical manipulator 520 and the third medical manipulator 530 are protruded from the treatment tool outlet holes indicated by B2, respectively. Although it is illustrated that the distal end of the endoscope 40 is protruding from the endoscope outlet hole indicated by B1 for convenience of explanation, the cap 48 may be configured such that the distal end of the endoscope 40 does not protrude. Further, though illustration is omitted for convenience, a tube may further be included, which forms a channel between each hole of the cap 48 and the drive device 20. This enables smooth operation of the medical manipulator 500.

Further, though not limited thereto, one treatment tool 50 is protruding from the cap 48 via the insertion section of the endoscope 40 whereas two treatment tools 50 are protruding from the cap 48 via the overtube 46 in FIGS. 2 and 3. For example, as shown in FIG. 4, three treatment tools 50 may protrude from the cap 48 via the overtube 46, thereby performing treatment such as ESD according to the technique of the present embodiment. In the cap 48 in FIG. 4, one endoscope outlet hole indicated by B3 and three treatment tool outlet holes indicated by B4 are formed. In addition, though not shown in the drawings, for example, the endoscope 40 may have two treatment tool channels, where the two treatment tools 50 protrude from the cap 48 via the insertion section of the endoscope 40 whereas one treatment tool 50 protrudes from the cap 48 via the overtube 46. Further, though not shown in the drawings, an example in which three treatment tools 50 protrude from the cap 48 via the insertion section of the endoscope 40 may be applied.

Although FIGS. 2 and 3 illustrate that the cap 48 is engaged and integrated with the overtube 46, for example, the cap 48 may be engaged with the endoscope 40 and the endoscope 40 can be displaced independently of the overtube 46 as shown in FIG. 5. For example, at the start of treatment, the endoscope 40, the overtube 46, and the cap 48 may be inserted into a body in an integrated state, and when the distal end section of the endoscope 40 approaches a site to be treated, the overtube 46 may be fixed with a balloon (not shown) and the endoscope 40 engaged with the cap 48 may be driven away from the overtube 46. Further, although FIG. 2, etc. illustrate the size of the cap 48 equal to or larger than the size of the overtube 46, the size of the cap 48 may be, for example, smaller than the size of the overtube 46. In this way, for example, the endoscope 40 engaged with the cap 48 can be driven inside the overtube 46.

Further, though not shown in FIG. 2, etc., for example, the drive device 20 may further include an overtube drive device which drives the overtube 46. The overtube drive device can be configured with a drive device equivalent to the endoscope drive device 24.

The endoscope 40 and the treatment tool 50 of the present embodiment include drive units according to a required number of a degree of freedom. For example, the second treatment tool drive device 22 includes a motor unit 220. The motor unit 220 includes, for example, a first bend operation drive section 221, a second bend operation drive section 222, an opening/closing operation drive section 223, a roll operation drive section 224, and an advance/retreat operation drive section 225.

The first bend operation drive section 221 pulls or loosens a pair of wires (not shown) based on a control signal received from the control device 10, thereby bending the second medical manipulator 520 in the direction along the axis UD. As a result, the direction of the grasping section 522 is changed along the direction indicated by D21. Similarly, the second bend operation drive section 222 bends the second medical manipulator 520 in the direction along the axis LR based on the control signal received from the control device 10. As a result, the direction of the grasping section 522 is changed along the direction indicated by D22.

Figure 6:
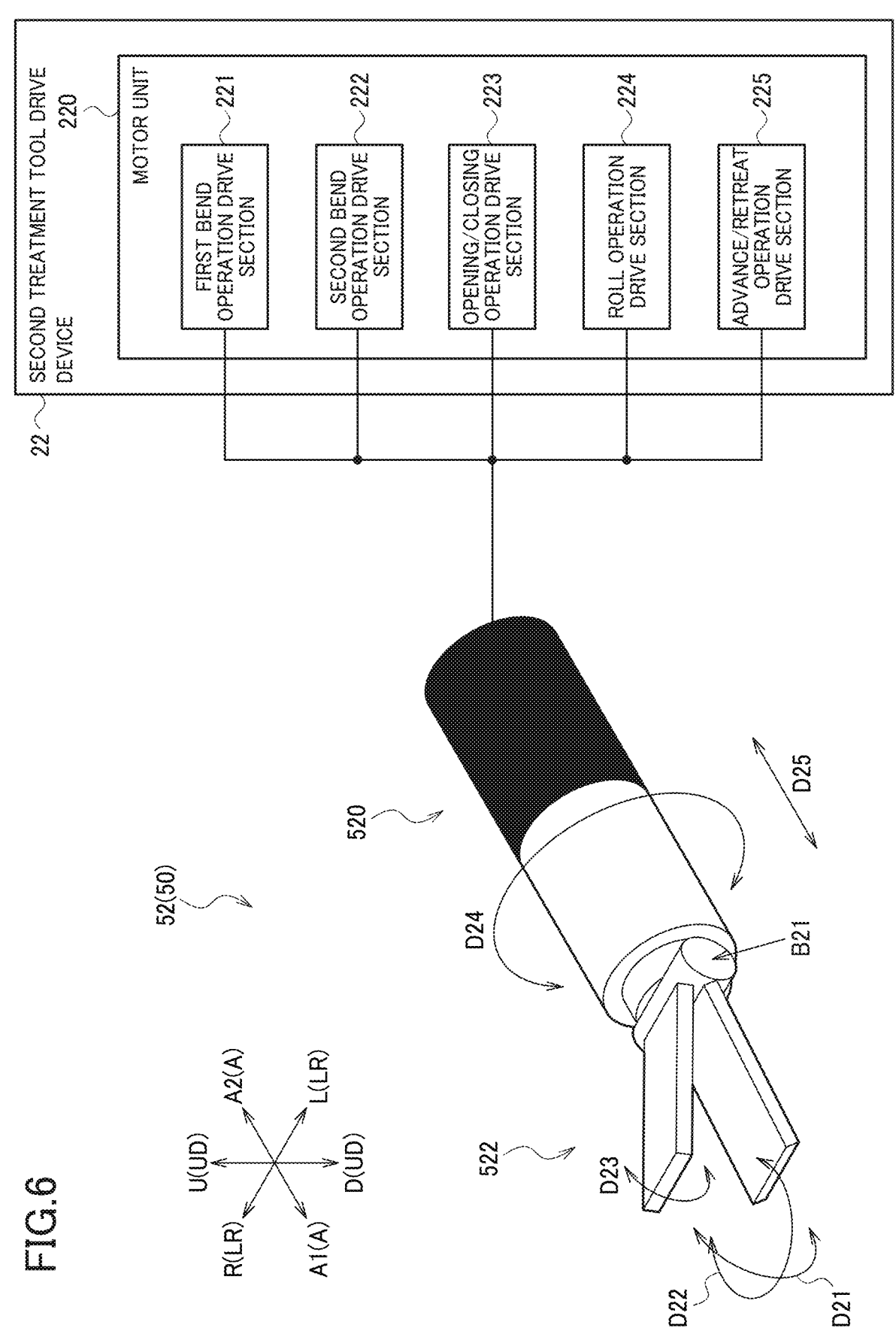
FIG. 6 is a diagram illustrating an example configuration of a second treatment tool drive device.

The opening/closing operation drive section 223 controls an opening/closing operation of the grasping section 522. For example, based on the control signal received from the control device 10, one of grasping pieces rotates about the rotation axis indicated by B21 along the direction indicated by D23. Note that the grasping section 522 shown in FIG. 6 is one example, and known structures can widely be applied.

The roll operation drive section 224 controls a roll rotating operation of the distal end section of the second medical manipulator 520. For example, it rotates the distal end section of the second medical manipulator 520 in the direction indicated by D24 based on the control signal received from the control device 10.

The advance/retreat operation drive section 225 controls an advance/retreat operation of the distal end section of the second medical manipulator 520. The advance/retreat operation drive section 225 moves forward and backward the second medical manipulator 520 by, for example, a drive mechanism including a linear motor, along the axis A based on the control signal received from the control device 10.

Note that the drive units of the third treatment tool drive device 23 and the endoscope drive device 24 can be implemented by a drive unit similar to the motor unit 220 of the second treatment tool drive device 22 described above. Note that in the third treatment tool drive device 23, for example, a configuration corresponding to the roll operation drive section 224 described above may be omitted. In addition, in the endoscope drive device 24, for example, a driving unit 70 described later with reference to FIG. 8 may slide against a floor in a predetermined direction, thereby achieving an equivalent function to the advance/retreat operation drive section 225 described above.

Figure 7:
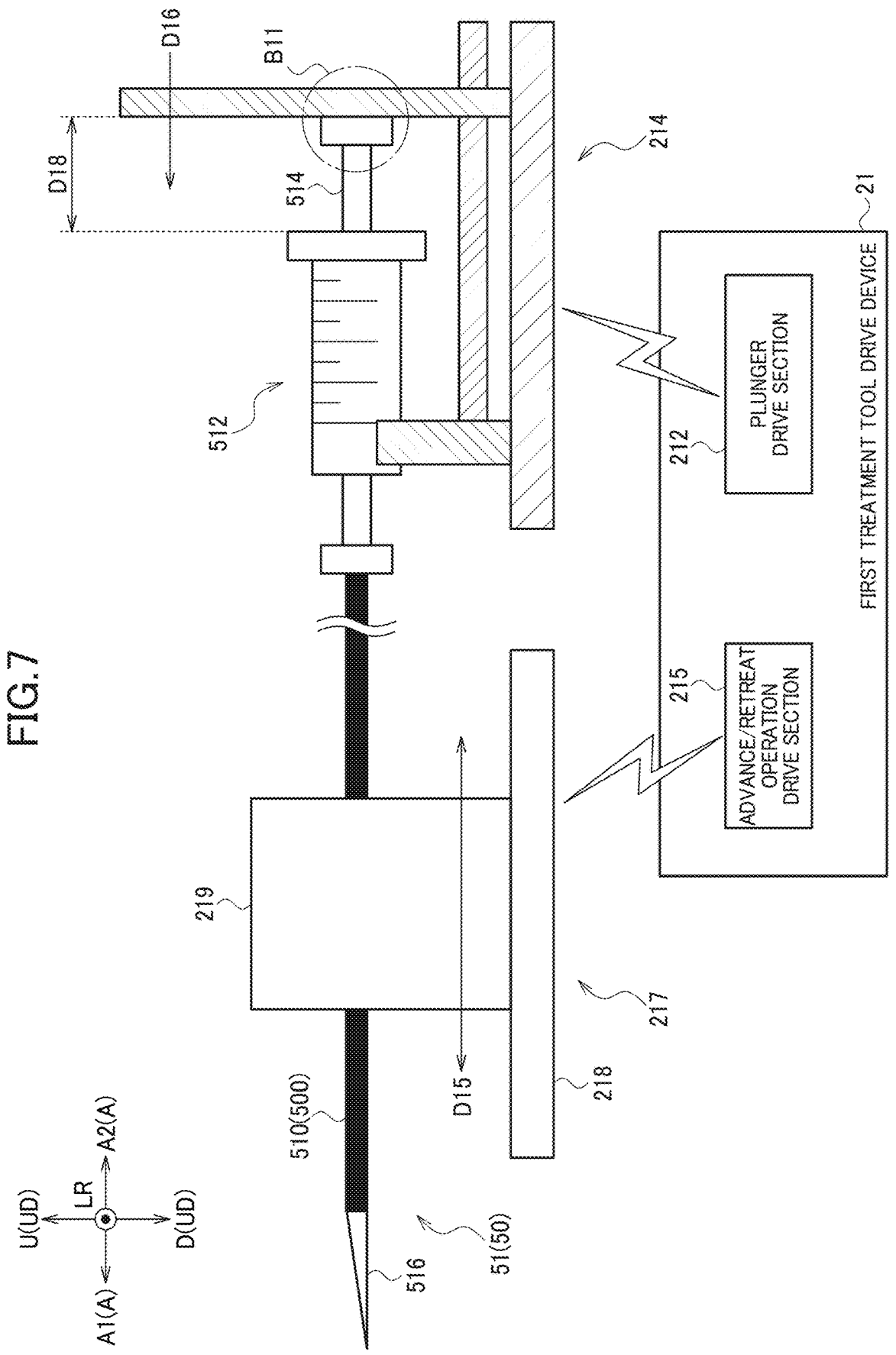
FIG. 7 is a diagram illustrating an example configuration of a first treatment tool drive device.

Further, the first treatment tool drive device 21 may be configured to include a plunger drive section 212 and an advance/retreat operation drive section 215, for example, as shown in FIG. 7. The plunger drive section 212 controls a syringe pump 214, thereby pushing a plunger 514 included in the syringe 512 in the direction indicated by D16, which is a direction toward a distal end side of the syringe 512. As a result, the injection fluid in the syringe 512 is compressed and ejected from the injection needle 516 by a compressive force. Note that the direction indicated by D16 in FIG. 7 may not the same as the direction of the axis A shown in FIG. 7. The advance/retreat operation drive section 215 controls a slider mechanism device 217. The slider mechanism device 217 includes a mechanism such as a linear motor or a rack and pinion, including a fixed section 218 and a slider section 219. The slider section 219 is integrated with a part of the first medical manipulator 510, and advances/retreats in the direction indicated by D15 relative to the fixed section 218 based on the control signal received from the control device 10. Note that the direction indicated by D15 in FIG. 7 is the same as the direction of the axis A. Accordingly, the injection needle 516 advances/retreats along the direction of the axis A.

Figure 8:
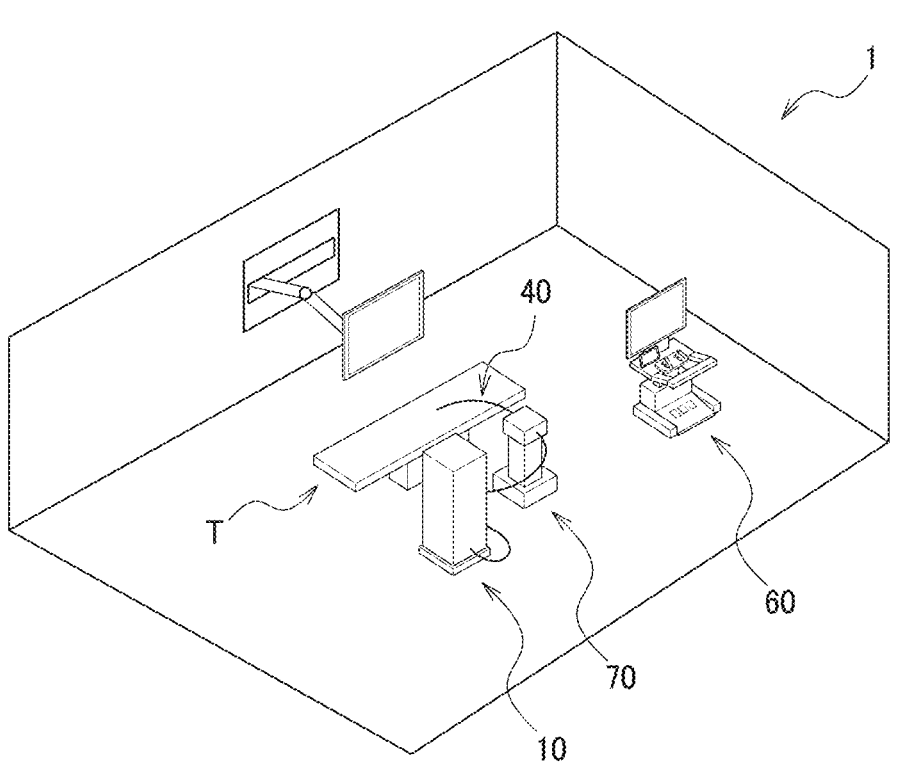
FIG. 8 is a diagram illustrating a specific example configuration of a surgical system.

More specifically, the surgical system 1 of the present embodiment may be configured as illustrated in FIG. 8. In FIG. 8, the surgical system 1 includes the aforementioned control device 10, and further includes the console 60 and the driving unit 70. Although the console 60 is wirelessly connected to the control device 10, for example, by a communication method compliant with a wireless communication standard such as Wi-Fi®, wired communication connection may also be used, for example. In the surgical system 1 of present embodiment, the endoscope 40 is inserted into a body of a subject (not shown) lying on an operating table T to perform treatment such as ESD.

The driving unit 70 corresponds to the endoscope drive device 24 in FIG. 2, and electrically operates each section of the endoscope 40 based on the control signal from the control device 10. Note that, though not shown in the drawings, units corresponding to the first treatment tool drive device 21, the second treatment tool drive device 22, and the third treatment tool drive device 23 may be included in the driving unit 70 or separately provided from the driving unit 70, that may be decided by a user as appropriate.

Figure 9:
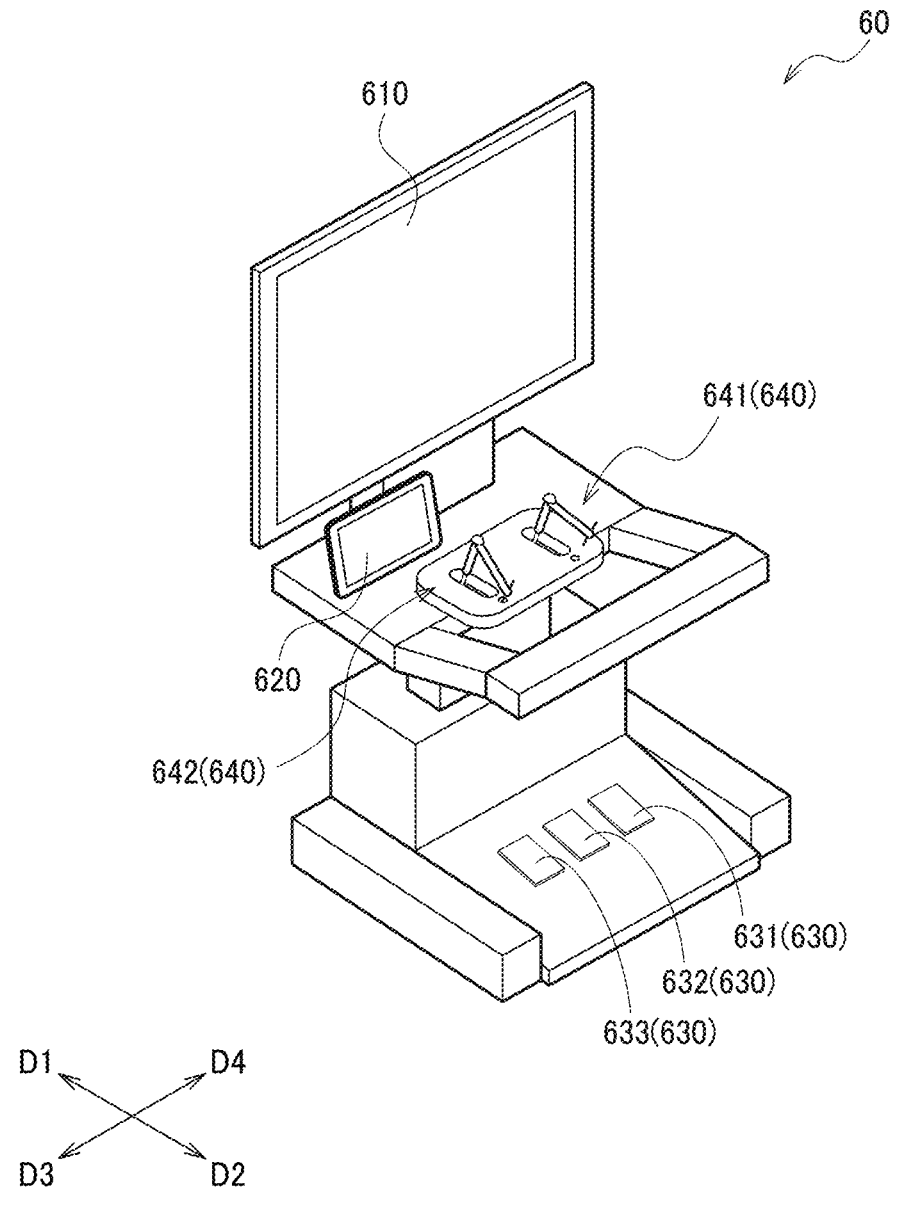
FIG. 9 is a diagram illustrating an example configuration of a console.

The console 60 includes, for example, the display 610, a touch panel 620, a foot pedal 630, and a handle 640. The display 610 displays an endoscopic image captured by the imager 42 via the control device 10. As described later in detail with reference to FIG. 38, the touch panel 620 displays the endoscopic image in the similar way as the display 610, and includes functions such as a drawing function. In addition, the touch panel 620 may display, for example, a part of a region including the center of the display 610. Note that there may be a plurality of foot pedals 630 and a plurality of handles 640 as shown in FIG. 9, for example, where the console 60 of the present embodiment includes a first foot pedal 631, a second foot pedal 632, and a third foot pedal 633 as the foot pedal 630. Note that there may be four or more foot pedals 630. Similarly, the console 60 of the present embodiment includes a first handle 641 and a second handle 642 as the handle 640. This allows a user to use the two handles 640 to perform treatment while properly using the endoscope 40 and a plurality of treatment tools 50 as appropriate. Although not shown in the drawings, the console 60 may further include an operation section for performing other operations, in addition to the handle 640. The other operations are, for example, an air and water delivery operation, an operation of changing illumination modes of a light source device, or the like.

Note that the direction indicated by D1 in FIG. 9 is a direction along which a user faces the console 60, also referred to as a forward direction. The direction indicated by D2 is a direction opposite to the direction indicated by D1, also referred to as a backward direction. The directions indicated by D1 and D2 together are also referred to as a forward and backward direction. The direction indicated by D3 is orthogonal to the forward and backward direction, also referred to as a left direction. The direction indicated by D4 is a direction opposite to the direction indicated by D3, also referred to as a right direction. The directions indicated by D3 and D4 together are also referred to as a left and right direction. The same applies to FIG. 11 described later.

For example, in the console 60 of the present embodiment, the foot pedal 630 includes a foot switch (not shown), and by an operation of stepping on the foot pedal 630 by a user, the control signal is transmitted from the foot switch to the control device 10. The control device 10 controls the endoscope 40 or the medical manipulator 500 in accordance with a combination of the control signal based on the operation of the foot pedal 630 and the control signal based on the operation of the handle 640 as described later.

More specifically, for example, the memory 130 of the control device 10 stores a table shown in FIG. 10. For example, when a user operates the first foot pedal 631 and the first handle 641, the control device 10 transmits the control signal from the first handle 641 to the third treatment tool drive device 23. In addition, when the user operates the first foot pedal 631 and the second handle 642, the control device 10 transmits the control signal from the second handle 642 to the second treatment tool drive device 22. Further, when the user operates the second foot pedal 632 and the first handle 641, the control device 10 transmits the control signal from the first handle 641 to the endoscope drive device 24. Further, when the user operates the third foot pedal 633 and the first handle 641, the control device 10 transmits the control signal from the first handle 641 to the first treatment tool drive device 21.

By making the control device 10 store the table shown in FIG. 10, for example, the user can operate the right first handle 641 while stepping on the second foot pedal 632 at the center of the console 60, thereby operating the endoscope 40. In addition, the user can operate the right first handle 641 while stepping on the third foot pedal 633 on the left side of the console 60, thereby operating the first treatment tool 51. Further, the user can operate the left second handle 642 while stepping on the first foot pedal 631 on the right side of the console 60, thereby operating the second treatment tool 52, and also operate the third treatment tool 53 by operating the right first handle 641.

Figure 11:
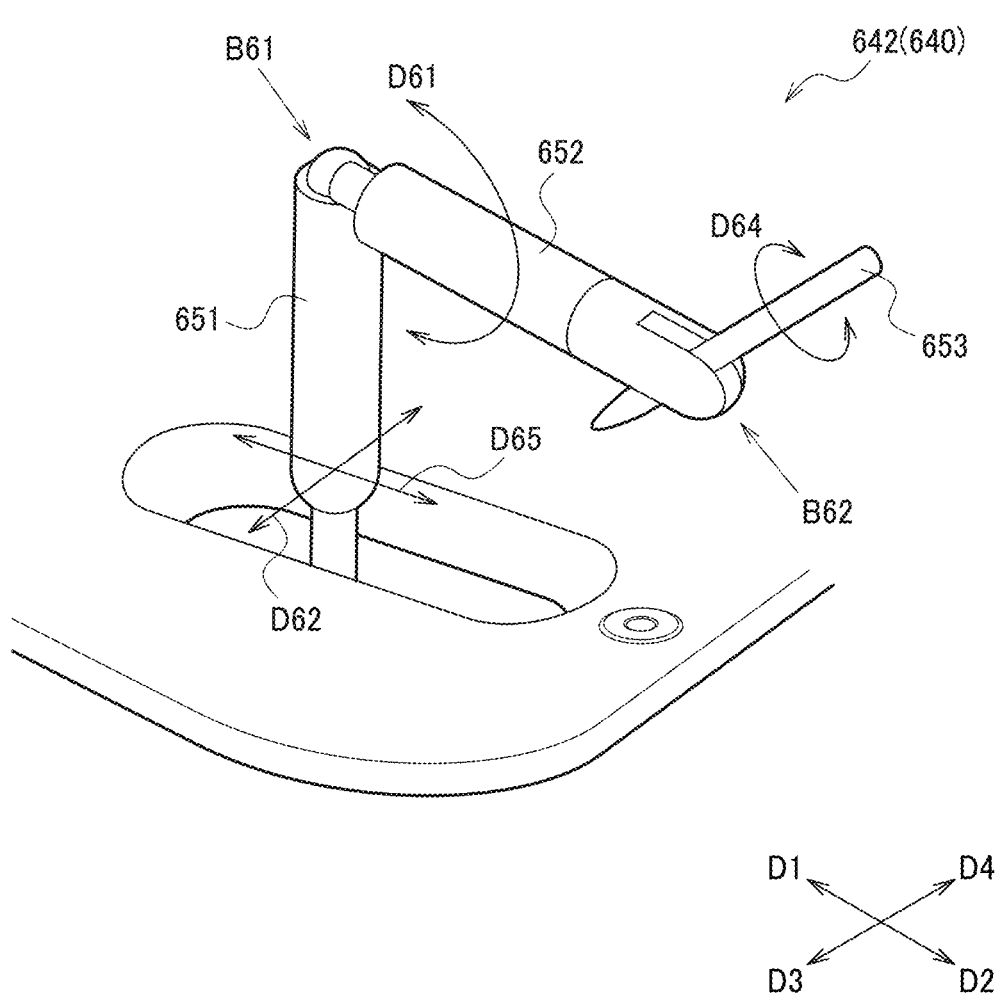
FIG. 11 is a diagram illustrating an example configuration of a handle.

More specifically, the handle 640 may be configured as illustrated in FIG. 11. In FIG. 11, the handle 640 includes a first part 651, a second part 652, and a third part 653. The first part 651 and the second part 652 are connected to each other via a joint indicated by B61. The second part 652 and the third part 653 are connected to each other via a joint indicated by B62. Note that although FIG. 11 only illustrates the second handle 642, the first handle 641 is similar to the second handle 642.

The first part 651 can be displaced in the directions indicated by D62 and D65. The direction indicated by D62 is the same as the left and right direction described above with reference to FIG. 9. The direction indicated by D65 is the same as the forward and backward direction described above with reference to FIG. 9. For example, a user moves the second part 652 along the direction indicated by D65 while holding the second part 652, such that the first part 651 is displaced in the forward and backward direction via the joint indicated by B61. Similarly, for example, the user moves the second part 652 along the direction indicated by D62 while holding the second part 652, such that the first part 651 is displaced in the left and right direction via the joint indicated by B61. Further, the user can rotate the second part 652 in the direction indicated by D61 about a rotation axis provided on the joint indicated by B61. Yet further, the user can roll the third part 653 around a longitudinal direction of the third part 653 in the direction indicated by D64.

As a result of the operation of the handle 640 by the user, the medical manipulator 500 advances/retreats, bends, rolls, or the like based on the control signal output by a sensor and the like (not shown). For example, suppose that the user wants to operate the second handle 642 while stepping on the first foot pedal 631 as described above, thereby operating the second treatment tool 52. For example, the user rotates the second part 652 in the direction indicated by D61 in FIG. 11, such that the second medical manipulator 520 bends in the direction indicated by D21 in FIG. 6. In addition, for example, the user operates the second handle 642 to displace the first part 651 in the direction indicated by D62 in FIG. 11, such that the second medical manipulator 520 bends in the direction indicated by D22 in FIG. 6. Further, for example, the user rolls the third part 653 in the direction indicated by D64 in FIG. 11, such that the second medical manipulator 520 rolls in the direction indicated by D24 in FIG. 6. Yet further, for example, the user operates the second handle 642 to displace the first part 651 in the direction indicated by D65 in FIG. 11, such that the second medical manipulator 520 advances/retreats in the direction indicated by D25 in FIG. 6.

Furthermore, the handle 640 may further include an operation section such as a button (not shown). For example, the user may operate a button included in the first handle 641 while stepping on the first foot pedal 631, such that a high frequency current can flow to the high frequency electrode of the third treatment tool 53. In addition, for example, the user may operate a button included in the second handle 642 while stepping on the first foot pedal 631, such that opening/closing of the grasping section 522 of the second treatment tool 52 can be controlled.

Further, for example, the control device 10 may be configured to be able to set whether to enable or disable reception of the control signal transmitted from the handle 640. Enabling reception of the control signal transmitted from the handle 640 refers to transmitting, based on the control signal received from the handle 640, a corresponding control signal to each section of the drive device 20. Disabling reception of the control signal transmitted from the handle 640 refers to discarding an instruction based on the control signal received from the handle 640. Specifically, for example, the memory 130 of the control device 10 stores a table shown in FIG. 12 as well as the aforementioned table shown in FIG. 10. For example, since the second medical manipulator 520 performs all the operations of advance/retreat, bend, and roll as described above with reference to FIG. 6, reception of the control signal based on the operations of all the first part 651, the second part 652, and the third part 653 is enabled as indicated by B71 in FIG. 12.

The third medical manipulator 530 may be designed to advance/retreat and bend, but not roll. In this case, as indicated by B72 in FIG. 12, reception of the control signal based on the operations of the first part 651 and the second part 652 is enabled, whereas reception of the control signal based on the operation of the third part 653 is disabled as indicated by B73 in FIG. 12.

Further, since the endoscope 40 performs all the operations of advance/retreat, bend, and roll as described above, for example, reception of the control signal based on the operations of all the first part 651, the second part 652, and the third part 653 is enabled as indicated by B74 in FIG. 12. In addition, according to the table in FIG. 10, a drive mechanism as a destination of the control signal based on the operation of the second handle 642 is not set when stepping on the second foot pedal 632, and thus, reception of the control signal based on the operation of the second handle 642 is disabled as indicated by B75 in FIG. 12.

Further, for example, the first treatment tool drive device 21 may be configured such that the first treatment tool 51 only advances/retreats as described above with reference to FIG. 7. In addition, when stepping on the third foot pedal 633, a drive mechanism as a destination of the control signal based on the operation of the second handle 642 is not set. In this case, as indicated by B76 in FIG. 12, reception of the control signal based on the operation of the first part 651 in the forward and backward direction is enabled, whereas reception of the control signal based on the operation of the first part 651 in the left and right direction is disabled. Further, as indicated by B77 in FIG. 12, reception of other control signals is disabled.

Note that a combination of the operations of the foot pedal 630 and the handle 640 is not limited to the above. For example, in a case that the drive device 20 further includes the aforementioned overtube drive device, a breakdown of the table in FIG. 10 may be changed as follows. For example, when the user operates the second foot pedal 632 and the second handle 642, the control device 10 may transmit the control signal from the second handle 642 to the first treatment tool drive device 21. In addition, for example, when the user operates the third foot pedal 633 and the first handle 641, the control device 10 may transmit the control signal from the first handle 641 to the overtube drive device.

Figure 13:
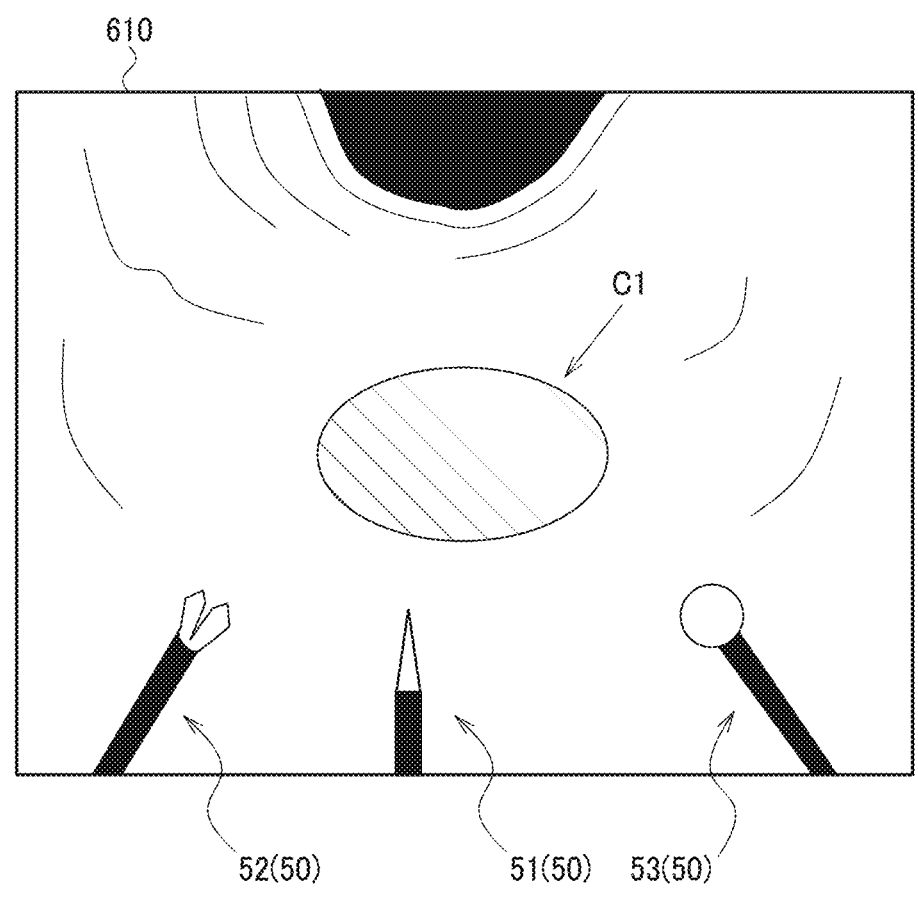
FIG. 13 is a diagram illustrating an example screen displayed on a display of a console.

By the console 60 thus configured, the user operates the treatment tool 50 as appropriate while watching the display 610, thereby performing treatment such as ESD on a treatment target indicated by C1, for example, as shown in FIG. 13. The treatment target can also be referred to as a lesion site. The lesion site herein refers to an area that appears to be different from a normal state, and is not necessarily limited to the one caused by a disease. For example, the lesion site is a tumor, but not limited thereto and may be a polyp, inflammation, diverticulum, and the like. Note that the treatment target of ESD is an early tumor. The early tumor refers to, for example, a tumor whose growth remains within a mucosal layer or a submucosal layer, as described later with reference to FIG. 20. Note that the display in FIG. 13 is merely an example, and it is not required that the first treatment tool 51, the second treatment tool 52, and the third treatment tool 53 are simultaneously displayed on the display 610.

A treatment flow with the technique of the present embodiment applied will be described with reference to FIG. 14. A user sets the first treatment tool 51, the second treatment tool 52, and the third treatment tool 53 (step S10). Setting of the first treatment tool 51, the second treatment tool 52, and the third treatment tool 53 means that three treatment tool channels are configured with the endoscope 40 or a combination of the endoscope 40 and the overtube 46, and the first treatment tool 51, the second treatment tool 52, and the third treatment tool 53 are inserted into respective treatment tool channels.

Thereafter, the user sets a injection position (step S100), a target amount (step S200), and direction information (step S300). The injection position refers to a position where the injection needle 516 is to be inserted, sometimes simply referred to as "position". The target amount refers to a target value of an injection amount of the injection fluid to be injected into the injection position. For example, the user sets a position around the lesion site into which the injection needle 516 is to be inserted, sets an angle of the injection needle 516 toward the position, and sets the target amount of the injection fluid to be injected after inserting the injection needle 516.

Figure 14:
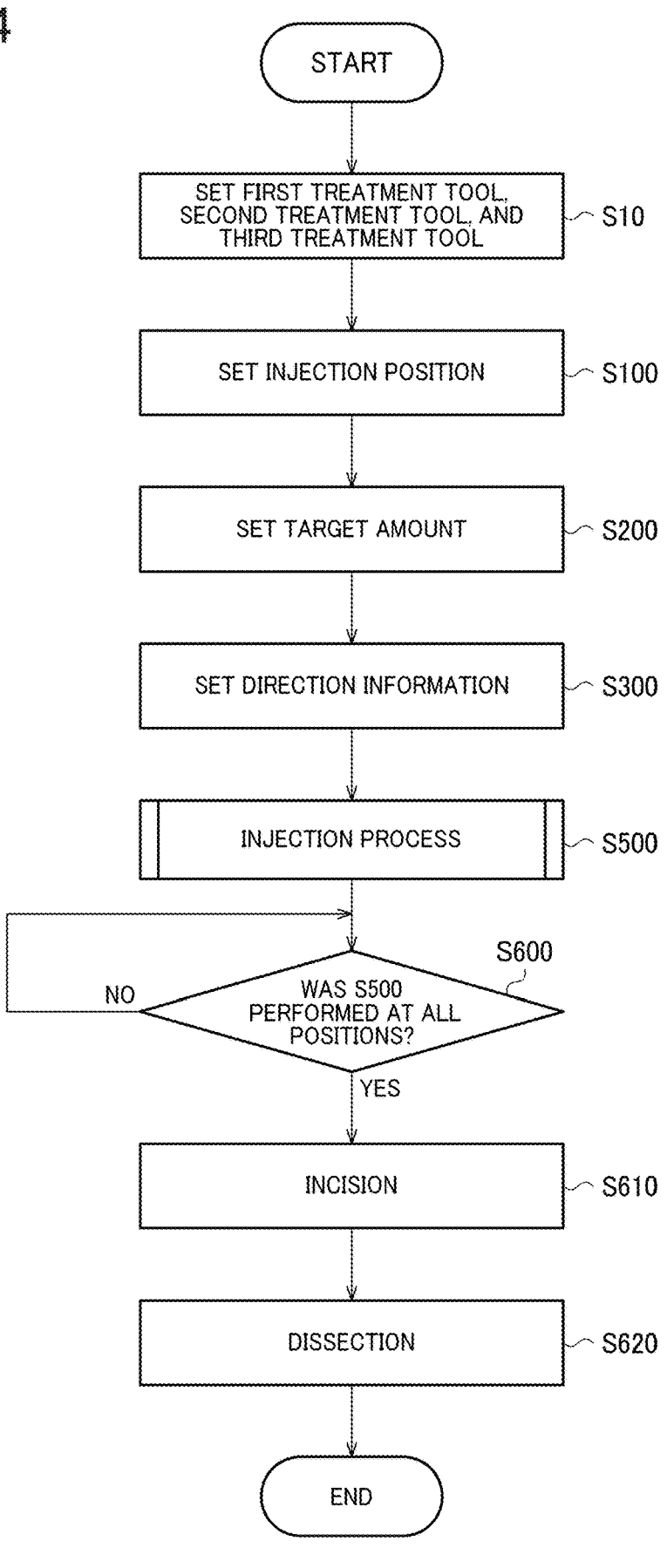
FIG. 14 is a diagram illustrating an example of a treatment flow of ESD.

Note that although not shown in FIG. 14, marking is performed after the step S300. The marking forms a predetermined marker for performing a injection process (step S500), incision (step S610), and the like described later. The predetermined marker is formed by performing a little cauterization around the lesion site using, for example, the aforementioned third treatment tool 53. Note that the marking may be, for example, segmentation of a region associated with the lesion site on a captured endoscopic image.

Figure 18:
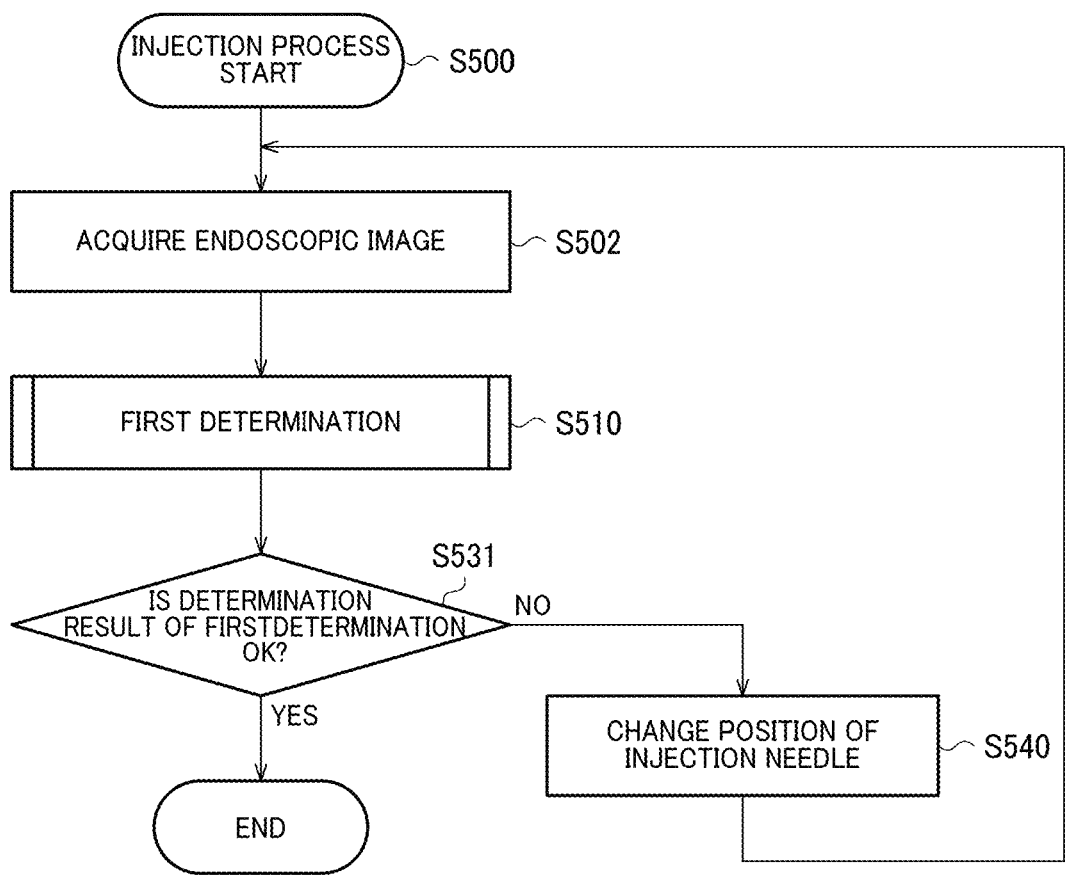
FIG. 18 is a flowchart illustrating example processing of a injection process.

Thereafter, the processor 100 performs the injection process (step S500). The details of the injection process (step S500) will be described later with reference to FIG. 18. The processor 100 performs a process of determining whether or not the injection process (step S500) was performed at all positions set in the step S100 (step S600). When the processor 100 determines that the injection process (step S500) was performed at all positions set in the step S100 (YES in step S600), the user performs incision (step S610). While the incision (step S610) is performed using, for example, the third treatment tool 53, the incision (step S610) can be performed smoothly by grasping the lesion site with the grasping section 522 of the second treatment tool 52, for example. On the other hand, in a case of determination NO in the step S600, the user inserts the injection needle 516 into a position where no injection process (step S500) has been performed, and the processor 100 performs the injection process (step S500) again.

Thereafter, the user performs dissection (step S620). For example, the user removes the lesion site which is lifted from the submucosal layer due to the incision (step S610). For example, the lesion site is collected by moving backward the second medical manipulator 520 to a position outside the body while grasping the lesion site with the grasping section 522 of the second treatment tool 52. Alternatively, the lesion site may be collected by replacing any of the first treatment tool 51, the second treatment tool 52, and the third treatment tool 53 with a dedicated treatment tool for collecting the lesion site, such as a net treatment tool. Note that when bleeding occurs, the step S620 may include, for example, a process of cauterization and hemostasis of the bleeding site using the third treatment tool 53. Note that when the size of the lesion site is larger than the diameter of the channel of the second medical manipulator 520, the endoscope 40 and the medical manipulator 500 may be moved backward to the position outside the body while grasping the lesion site with the grasping section 522.

Note that three treatment tool channels are not required for implementing the injection process (step S500) of the present embodiment. For example, the technique of the present embodiment is applicable to a case where two treatment tool channels are provided. In this case, ESD may be performed with the flow illustrated in FIG. 15, for example. Note that in FIG. 15, description of the processes similar to those in FIG. 14 will be omitted as appropriate.

Figure 15:
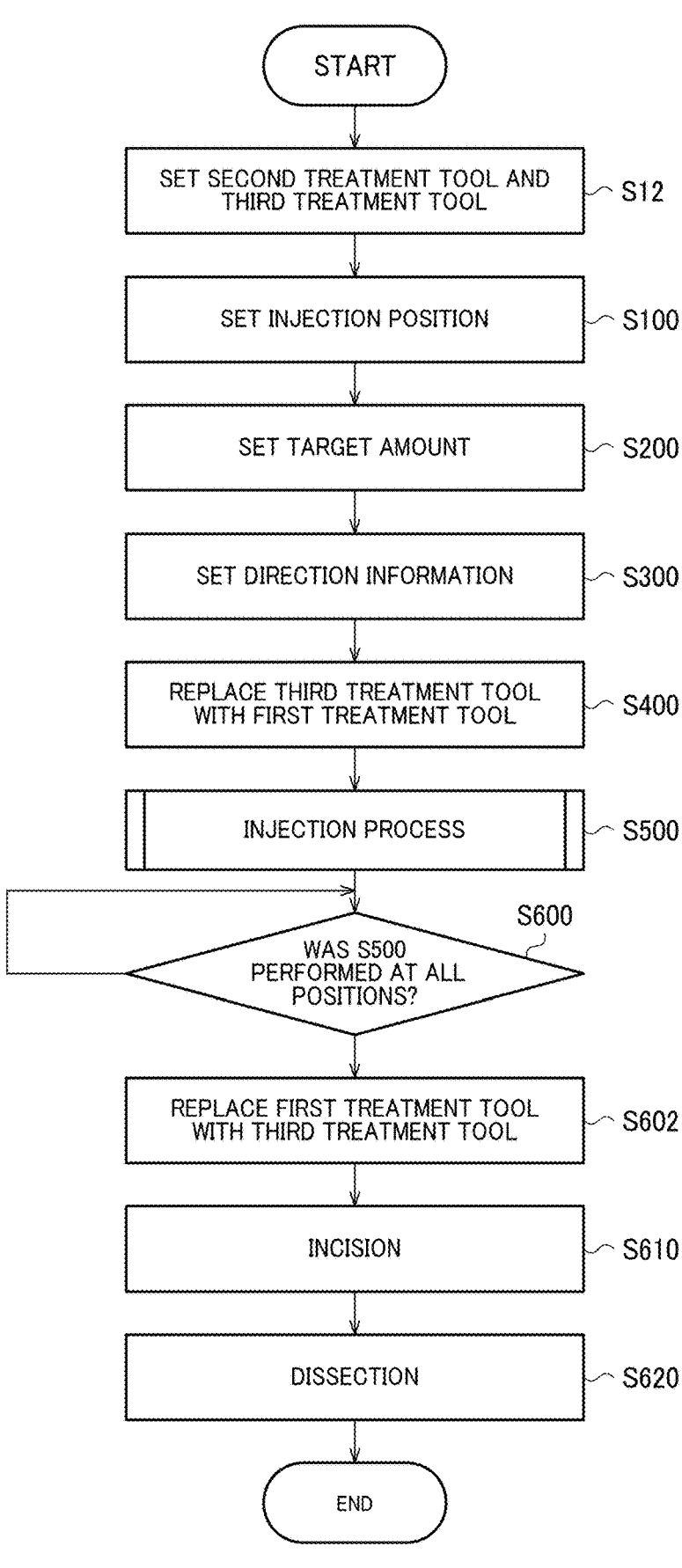
FIG. 15 is a diagram illustrating another example of the treatment flow of ESD.
Figure 16:
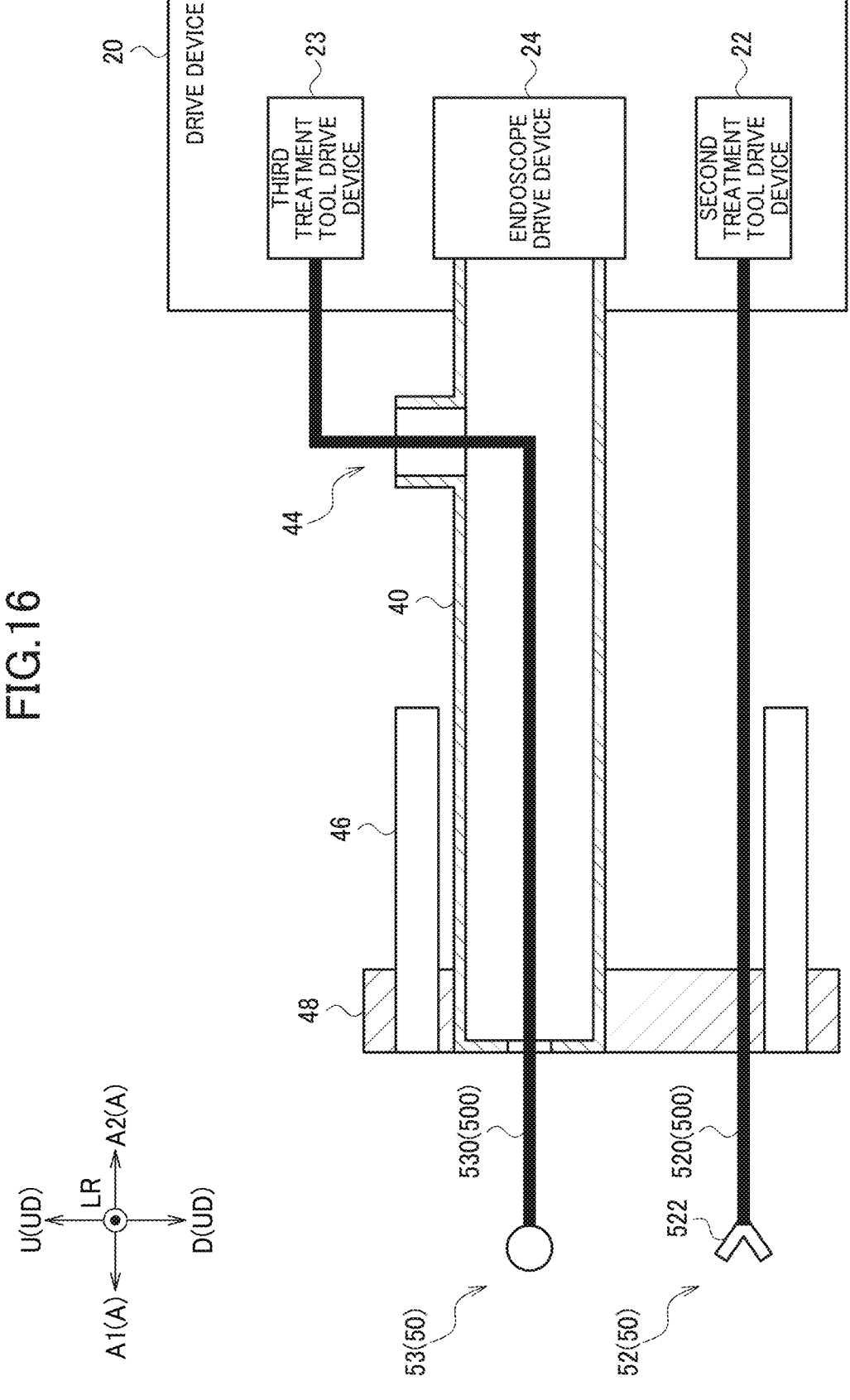
FIG. 16 is a diagram illustrating another example configuration of the drive device.

In FIG. 15, the user sets the second treatment tool 52 and the third treatment tool 53 (step S12). In other words, two treatment tool channels are configured with the endoscope 40 or the combination of the endoscope 40 and the overtube 46, and the second treatment tool 52 and the third treatment tool 53 are inserted into respective treatment tool channels. For example, as shown in FIG. 16, the third treatment tool 53 is inserted into the treatment tool insertion hole 44 of the endoscope 40, whereas the second treatment tool 52 is inserted into the treatment tool channel provided in the overtube 46. Then, in the same manner as in FIG. 14, the step S100, the step S200, and the step S300 as well as the marking using the third treatment tool 53 will be performed.

Figure 17:
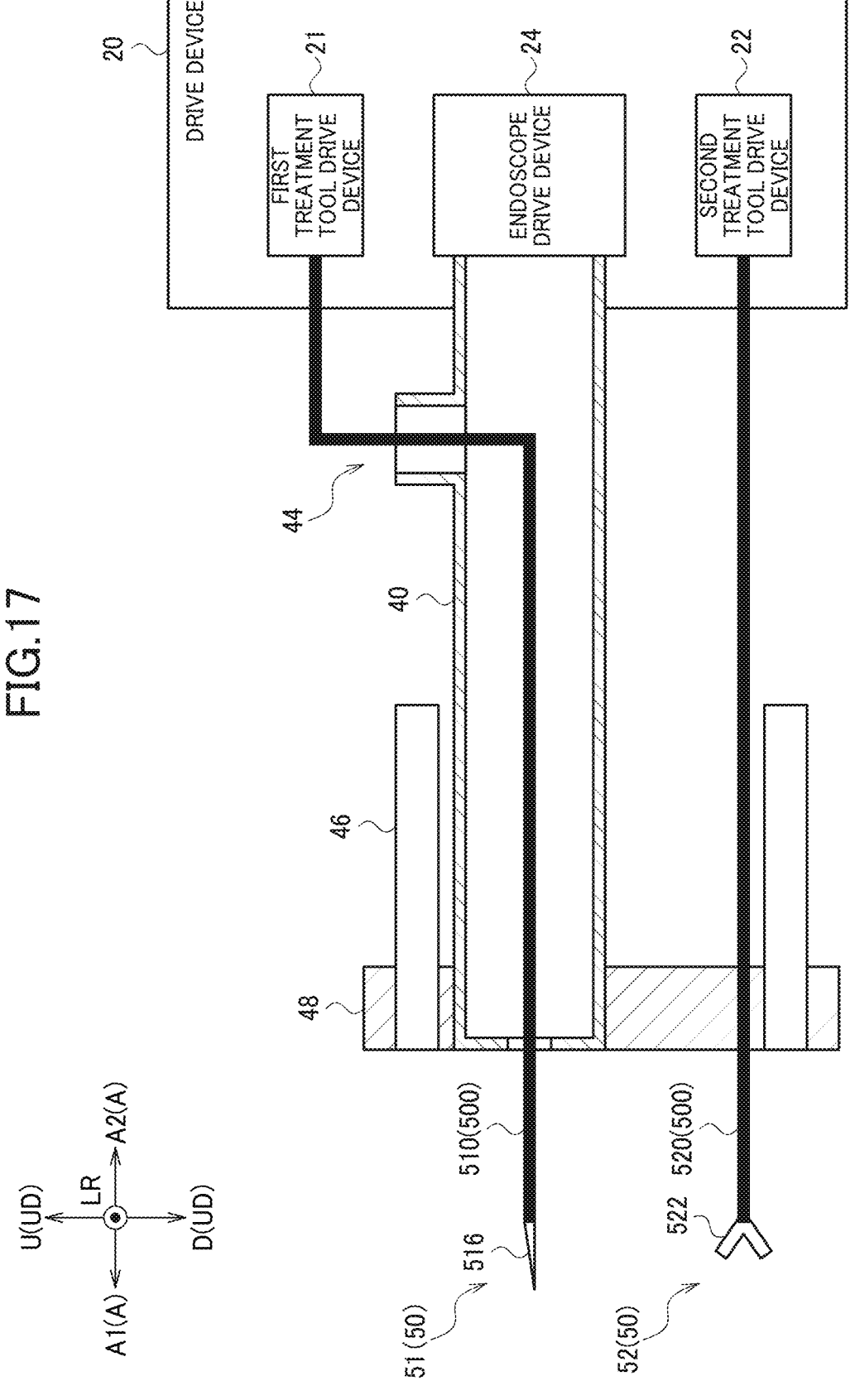
FIG. 17 is a diagram illustrating another example configuration of the drive device.

Thereafter, the user replaces the third treatment tool 53 with the first treatment tool 51. In other words, as shown in FIG. 17, the first treatment tool 51 is inserted into the treatment tool insertion hole 44 of the endoscope 40, whereas the second treatment tool 52 is continuously inserted into the treatment tool channel provided in the overtube 46. Then, the processor 100 performs the injection process (step S500) described later and the step S600. Thereafter, in a case of determination YES in the step S600, the user replaces the first treatment tool 51 with the third treatment tool 53. In other words, in the case of determination YES in the step S600, the injection has been completed and there is no need to use the first treatment tool 51, so that the incision (step S610) and the dissection (step S620) may be performed using the second treatment tool 52 and the third treatment tool 53.

The user may select, depending on the situation, the flow in FIG. 14 or the flow in FIG. 15 as appropriate to perform the treatment of ESD. Note that since the step S400 and the step S602 are added in FIG. 15 as compared to the FIG. 14, the user can complete the treatment in a shorter time by selecting the flow in FIG. 14. Further, the flow of the modification described later with reference to FIG. 46 can be applied to a case where three treatment tool channels are included.

Further, though illustration of the flow is omitted, for example, in a case where the incision (step S610) can be performed by only the third treatment tool 53 without using the second treatment tool 52, ESD may be performed using the endoscope 40 including one treatment tool channel.

The injection process (step S500) will be described. The injection process (step S500) is performed at the injection position set in the step S100 at a timing after starting control of the first medical manipulator 510 based on the direction information set in the step S300. In other words, the execution of the step S500 is started at a timing when the injection needle 516 is inserted into an inner wall and the control for the syringe pump 214 to push the plunger 514 in the direction indicated by D16 in FIG. 7 is started.

The processor 100 acquires an endoscopic image (step S502). For example, the processor 100 acquires an endoscopic image captured by the imager 42 at a timing of performing first determination (step S510) described later. Then, the processor 100 performs the first determination (step S510). Thereafter, the processor 100 determines whether a determination result of the first determination (step S510) is OK or NG (step S531).

When determining the determination result of the first determination (step S510) as NG (NO in step S531), the processor 100 changes the position of the injection needle 516 (step S540) and performs the step S502 again. In the step S540, for example, the processor 100 controls the first treatment tool drive device 21 such that the injection needle 516 at the distal end of the first medical manipulator 510 is pulled out by a predetermined length.

Figure 19:
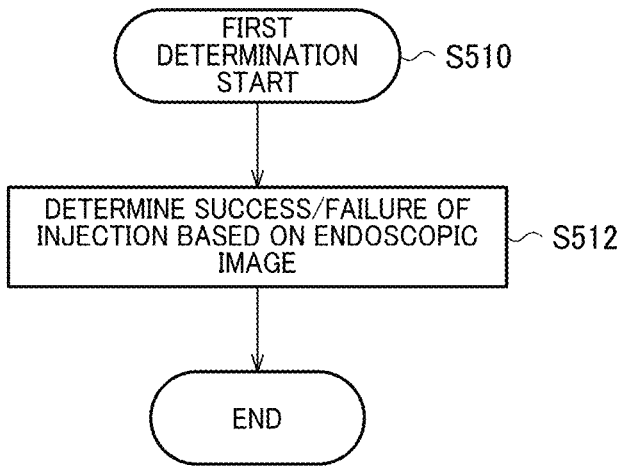
FIG. 19 is a flowchart illustrating example processing of first determination.

The first determination (step S510) as prescribed determination according to the technique of the present embodiment will be described using the flowchart in FIG. 19. Hereinafter, the first determination as the prescribed determination is simply referred to as first determination. The processor 100 determines, based on the endoscopic image, success/failure of the injection (step S512). In other words, once the endoscopic image as input data is input to the control device 10, the processor 100 outputs a determination result of success/failure of the injection. For example, though not shown in the drawings, the user sets around an area where the injection needle 516 is inserted as ROI (Region Of Interest) in the endoscopic image acquired in the step S502. Then, the processor 100 determines whether or not the injection fluid was injected. Note that ROI stands for Region of Interest.

A specific effect of the injection process (step S500) will be described with reference to FIGS. 20, 21, and 22. FIG. 20 is a cross-sectional view conceptually illustrating that the injection needle 516 is inserted into an inner wall of a digestive tract such as stomach, esophagus, and large intestine, that is the timing of starting the injection process (step S500). The inner wall consists of a mucosal layer indicated by L1, a submucosal layer indicated by L2, a muscle layer indicated by L3, and the like. Note that serosa and the like outside the muscle layer are omitted in FIG. 20. The lesion site indicated by C11 in FIG. 20 is an early tumor as described above, and assumed to be within the range of the mucosal layer indicated by L1.

Note that as shown in FIG. 20, the injection needle 516 is inserted into the inner wall along an inclined direction relative to a direction perpendicular to a direction along a surface of the inner wall. For example, as described above with reference to FIG. 7, when the first treatment tool drive device 21 can perform only the advance/retreat operation for the first medical manipulator 510, the processor 100 performs control to bend the endoscope 40 in the aforementioned step S300, thereby adjusting the direction of advance/retreat of the injection needle 516. This can reduce possibility that the injection needle 516 penetrates the inner wall. Particularly, since the large intestinal wall is thinner than the stomach wall, it is required that the injection needle 516 is not deeply inserted into the surface of the inner wall. In addition, since the submucosal layer is composed of fat, it is generally difficult to insert the injection needle 516 to keep it within the range of the submucosal layer of L2, and at the timing of starting the injection process (step S500), a distal end of the injection needle 516 typically reaches a part of the muscle layer.

Since the muscle layer is a hard layer made up of muscle fibers, the injection fluid does not enter the muscle layer even if the plunger drive section 212 drives the syringe pump 214. In other words, no change can be seen in the set ROI. In this case, the processor 100 determines NG in the first determination (step S510). Accordingly, the processor 100 determines NO in the step S531 and changes the position of the injection needle 516 in the step S540. More specifically, the processor 100 controls the advance/retreat operation drive section 215 to move the injection needle 516 by a predetermined amount in the direction A2. In other words, the injection needle 516 is pulled out from the inner wall by the predetermined amount in the step S540. Then, when the processor 100 determines NG in the repeated first determination (step S510), the step S540 is to be performed again.

By performing the step S540 a predetermined number of times, the distal end of the injection needle 516 is positioned within the submucosal layer indicated by L2, for example, as shown in FIG. 21. Since the syringe pump 214 keeps pushing the plunger 514, the injection fluid is ejected from the injection needle 516 at the timing shown in FIG. 21 to cause a state shown in FIG. 22. In FIG. 22, due to the injection fluid indicated by B81, the mucosal layer indicated by L11, the submucosal layer indicated by L12, and the lesion site indicated by C21 are in a raised state. Note that the muscle layer indicated by L13 in FIG. 22 is in substantially the same state as the muscle layer indicated by L3 in FIGS. 20 and 21. Though not shown in the drawings, this causes a change that each tissue is raised in the set ROI.

In this case, the processor 100 determines OK in the repeated first determination (step S510). Then, the processor 100 determine YES in the step S531 and the flow of the injection process (step S500) ends. This means that the injection has been completed at one position. Thereafter, for example, the user cauterizes and removes the area indicated by B82 and the like using the third treatment tool 53 by the incision (step S610), so that the lesion site indicated by C21 is lifted from the submucosal layer and can be subject to the dissection (step S620).

From the above, the surgical system 1 of the present embodiment includes the endoscope 40 including the imager 42 which captures an endoscopic image, the medical manipulator 500 with the injection needle 516 at the distal end section thereof, the drive device 20 which controls the medical manipulator 500 to control the position of the injection needle 516, and the processor 100. The processor 100 is configured to: control to inject the target amount of the injection fluid into the syringe 512 connected to the injection needle 516; acquire, from the imager 42, the endoscopic image in which the treatment target is captured; and perform the prescribed determination (first determination (step S510)) using the endoscopic image to determine success/failure of the injection. In addition, the processor 100 controls the drive device 20 to change the position of the injection needle 516 (step S540) based on the determination result of the prescribed determination (NO in step S531).

In this manner, the steps associated with the injection can be controlled automatically. As described above, ESD is a complex procedure using the first treatment tool 51, the second treatment tool 52, and the third treatment tool 53, which is a heavy burden on the user. In this respect, application of the technique of the present embodiment will reduce a burden on the user in the steps associated with the injection using the first treatment tool 51. This allows the user to concentrate on using the second treatment tool 52 and the third treatment tool 53 to perform the treatment smoothly. Note that in a case that three treatment tool channels are included, there is no step of replacing the first treatment tool 51 with the third treatment tool 53 and vice versa as described above so that the time of surgery can be shortened.

Further, the technique of the present embodiment may be implemented by the processor 100. That is, the processor 100 of the present embodiment controls the endoscope 40 including the imager 42 which captures an endoscopic image, and the drive device 20 which controls the medical manipulator 500 with the injection needle 516 at the distal end section thereof to control the position of the injection needle 516. In addition, the processor 100 of the present embodiment is configured to: control to inject the target amount of the injection fluid into the syringe 512 connected to the injection needle 516; acquire, from the imager 42, the endoscopic image in which the treatment target is captured; and perform the prescribed determination (first determination (step S510)) using the endoscopic image to determine success/failure of the injection, and control the drive device 20 to change the position of the injection needle 516 (step S540) based on the determination result of the prescribed determination (NO in step S531). In this manner, the effects similar to those described above can be obtained.

Furthermore, the technique of the present embodiment may be implemented by a control method. That is, the control method of the present embodiment is a method of controlling the endoscope 40 including the imager 42 which captures an endoscopic image, and the drive device 20 which controls the medical manipulator 500 with the injection needle 516 at the distal end section thereof to control the position of the injection needle 516. In addition, the control method of the present embodiment includes: controlling to inject the target amount of the injection fluid into the syringe 512 connected to the injection needle 516; acquiring, from the imager 42, the endoscopic image in which the treatment target is captured; and performing the prescribed determination (first determination (step S510)) using the endoscopic image to determine success/failure of the injection, and controlling the drive device 20 to change the position of the injection needle 516 (step S540) based on the determination result of the prescribed determination (NO in step S531). In this manner, the effects similar to those described above can be obtained.

Figure 23:
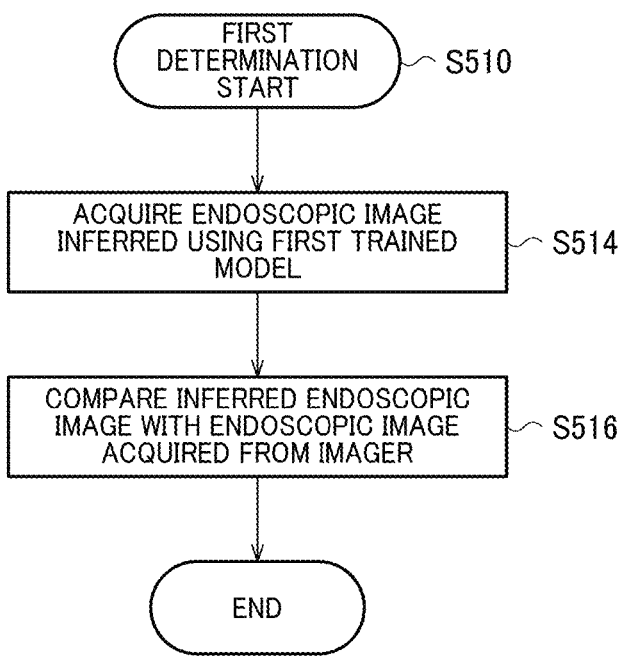
FIG. 23 is a flowchart illustrating another example processing of the first determination.

The technique of the present embodiment is not limited to the above, and various modifications can be made such as adding other features. For example, the aforementioned first determination (step S510) may be implemented as the example processing shown in the flowchart of FIG. 23. In FIG. 23, the processor 100 acquires an endoscopic image inferred by using the first trained model 141 (step S514). For example, the processor 100 infers, based on an endoscopic image captured immediately before starting the injection process (step S500), what kind of endoscopic image will be acquired when the injection is successful. Thereafter, the processor 100 compares the inferred endoscopic image with the endoscopic image actually acquired from the imager 42

(step S516). The first determination (step S510) shown in FIG. 23 can be implemented by configuring the control device 10 as the example configuration shown in FIG. 24.

Figure 24:
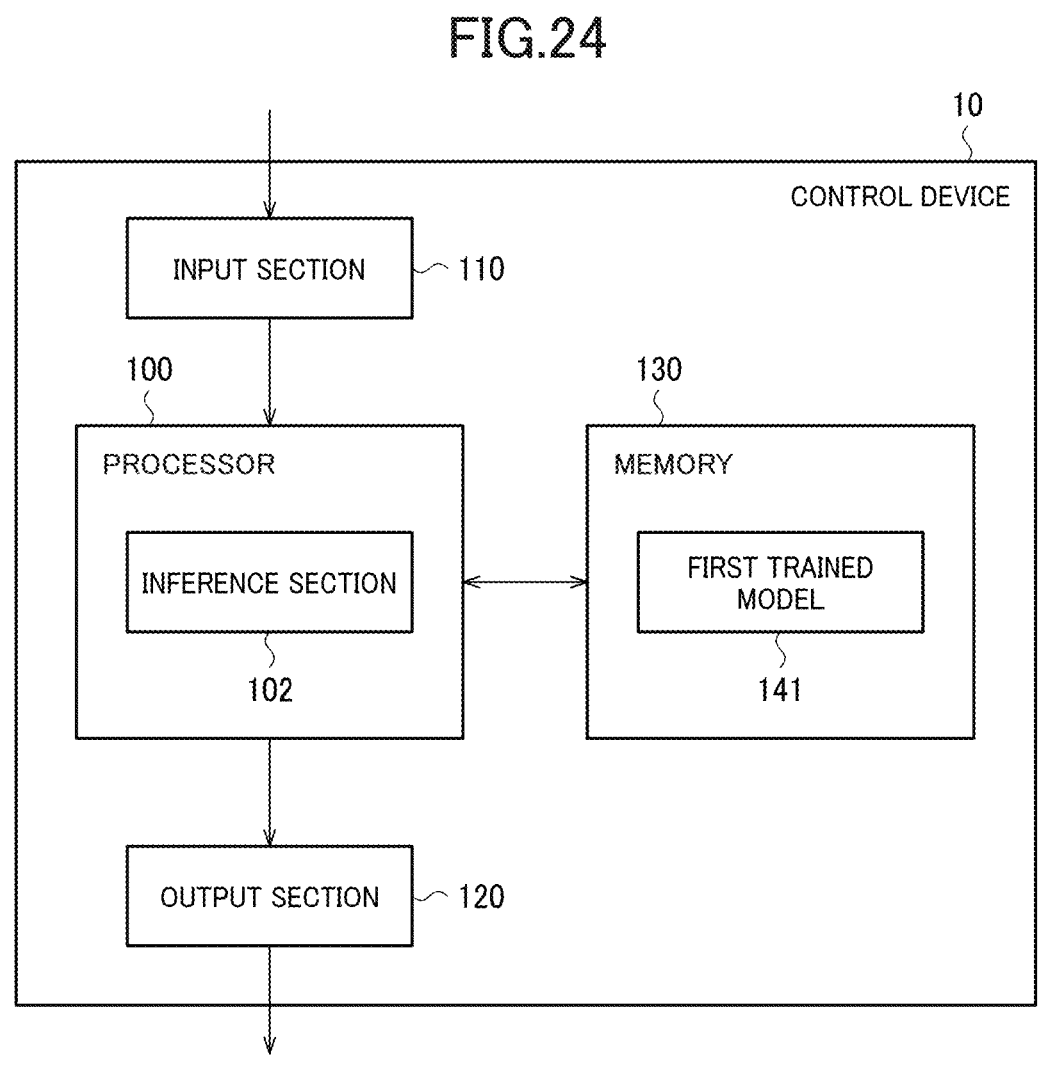

In FIG. 24, the control device 10 includes an input section 110, the processor 100 including an inference section 102, an output section 120, and the memory 130 which stores the first trained model 141. That is, the processor 100 reads out the first trained model 141 from the memory 130 and executes a program associated with the first trained model 141, thereby functioning as the inference section 102. Note that the inference section 102 can also execute programs associated with a second trained model 142, a third trained model 143, a fourth trained model 144, a fifth trained model 145, and a sixth trained model 146 described later.

The first trained model 141 of the present embodiment is a program module generated by performing machine learning, which is supervised learning. In other words, the first trained model 141 is generated through supervised learning based on a dataset in which input data is associated with a ground truth label. The same applies to the second trained model 142, the third trained model 143, the fourth trained model 144, the fifth trained model 145, and the sixth trained model 146 described later.

Further, in the first trained model 141 of the present embodiment, a neural network is included in at least a part of the model. Though not shown in the drawings, the neural network has an input layer to which data is input, an intermediate layer that performs computation based on output from the input layer, and an output layer that outputs data based on output from the intermediate layer. The number of the intermediate layer is not particularly limited. In addition, the number of nodes included in the intermediate layer is not particularly limited. In the intermediate layer, the node included in a given layer is connected to the node in the adjacent layer. A weighting coefficient is set for each connection. Each node multiplies output of the previous node by the weighting coefficient and obtains a total value of multiplication results. Further, each node adds a bias to the total value and applies an activation function to the addition result, thereby obtaining the output of the node. By sequentially performing this processing from the input layer to the output layer, the output of the neural network can be obtained. Note that various functions such as a sigmoid function and an ReLU function are known as the activation function, and these can be widely applied to the present embodiment. Note that the second trained model 142, the third trained model 143, the fourth trained model 144, the fifth trained model 145, and the sixth trained model 146 described later include the neural network as well.

The input section 110 is an interface that receives input data from the outside. For example, an input section 14 achieves the function as the input section 110 by inputting, to the input section 110, image data of the endoscopic image in which the lesion site as the treatment target before performing the injection is captured in the step S514.

The output section 120 is an interface that transmits data estimated by the inference section 102 to the outside. For example, by outputting data of the endoscopic image inferred by the inference section 102 as output data from the first trained model 141 in the step S514, the function as the output section 120 can be achieved.

Figure 25:
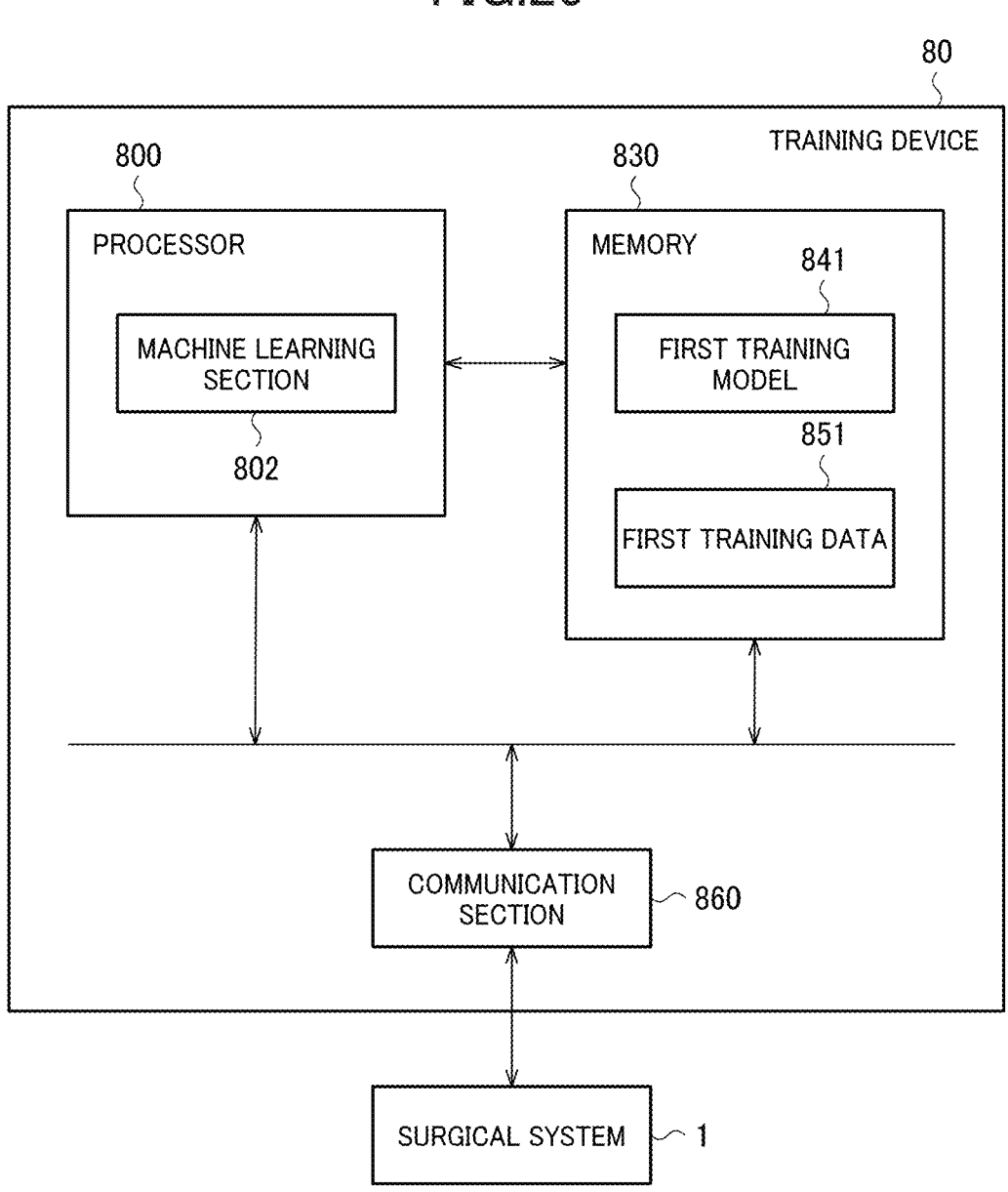
FIG. 25 is a diagram illustrating an example configuration of a training device.

Machine learning of the first trained model 141 is performed by, for example, a training device 80. FIG. 25 is a block diagram illustrating an example configuration of the training device 80. The training device 80 includes, for example, a processor 800, a memory 830, and a communication section 860, wherein the processor 800 includes a machine learning section 802.

The processor 800 controls input/output of data between each functional section such as the memory 830 and the communication section 860. The processor 800 can be implemented by hardware and the like similar to that of the processor 100 described above with reference to FIG. 1. The processor 800 performs various computation processing and controls operations such as data input to/output from the surgical system 1 based on a predetermined program read out from the memory 830, an operation input signal from the operation section (not shown in FIG. 25), and the like. The predetermined program herein includes a machine learning program (not shown). In other words, the processor 800 reads out, from the memory 830, and executes the machine learning program, necessary data, and the like as appropriate, thereby functioning as the machine learning section 802. The memory 830 stores a first training model 841 and first training data 851, as well as the machine learning program (not shown). The memory 830 can be implemented by a semiconductor memory and the like similar to the memory 130 described above with reference to FIG. 1.

The communication section 860 is a communication interface which can communicate with the surgical system 1 by a predetermined communication method. The predetermined communication method is, for example, the aforementioned Wi-Fi® and the like, but not limited thereto, and may be a communication method compliant with a wired communication standard such as USB. In this way, the training device 80 can transmit the first trained model 141 subjected to the machine learning to the surgical system 1, and the surgical system 1 can update the first trained model 141. Note that though FIG. 25 is an example in which the training device 80 is separate from the surgical system 1, it shall not preclude an example configuration in which the surgical system 1 includes a training server corresponding to the training device 80.

Though not shown in the drawings, the first training data 851 is a dataset including, as the ground truth label, the endoscopic image in which the lesion site as the treatment target before performing the injection is captured, and the endoscopic image in which shape change of the lesion site due to the injection is captured. The ground truth label is the endoscopic image showing that the area around the inserted injection needle 516 is raised and three-dimensional shape change is caused by successful injection as described above with reference to FIG. 22. The machine learning section 802 inputs numerous first training data 851 to the first training model 841, thereby updating the first training model 841 to give the first trained model 141.

Then, as described above, in the step S514 of FIG. 23, by inputting the endoscopic image in which the lesion site before performing the injection is captured to the input section 110 as the input data, the inference section 102 infers and outputs via the output section 120 the endoscopic image in which the lesion site after performing the injection is captured. Thereafter, in the step S516, the processor 100 compares the endoscopic image inferred in the step S514 with the endoscopic image actually acquired in the step S502 to determine success/failure of the injection. Then, when similarity between the images is equal to or greater than a predetermined threshold, the determination result of the first determination (step S510) is OK, and the processor 100 determines YES in the step S531. On the other hand, the similarity between the images is less than the predetermined threshold, the determination result of the first determination (step S510) is NG, and the processor 100 determines NO in the step S531 and performs the step S540 and the subsequent steps.

Note that the technique of the first determination (step S510) is not limited to the above. For example, the first training data 851 may be a dataset including, as the ground truth label, the endoscopic image after starting the injection process (step S500) and information indicating whether or not the injection is successful. The machine learning section 802 inputs, in the training phase, the first training data 851 to the first training model 841, which is to be updated as the first trained model 141. For example, the endoscopic image is input to the first training model 841 in the training phase, and the first training model 841 outputs the determination result of whether or not the injection is successful. Then, the machine learning section 802 provides feedback to optimize parameters of the neural network included in the first training model 841, based on an error between the output result and the ground truth label. As a result, the first trained model 141 is updated. Note that the technique related to the training phase is the same for the second trained model 142, the third trained model 143, the fourth trained model 144, the fifth trained model 145, and the sixth trained model 146 described later, and thus, the description thereof will be omitted in the following.

Then, in the first determination (step S510), the endoscopic image acquired in the step S502 is input to the input section 110, the processor 100 reads out the first trained model 141 from the memory 130, and the inference section 102 infers success/failure of the injection based on the input endoscopic image. Then, when information indicative of success of the injection is output from the output section 120, the determination result of the first determination (step S510) is OK, and the processor 100 determines YES in the step S531. On the other hand, when information indicative of failure of the injection is output from the output section 120, the determination result of the first determination (step S510) is NG, and the processor 100 determines NO in the step S531 and performs the step S540 and the subsequent steps.

As a result, the surgical system 1 of the present embodiment includes the first trained model 141 trained based on learning data (first training data 851) including the endoscopic image in which the treatment target into which the injection fluid was injected is captured. The processor 100 uses the first trained model 141 to determine, based on the endoscopic image, sufficiency of shape change of the treatment target (step S516), and when the shape change of the treatment target is determined to be insufficient (NO in step S532), the processor 100 controls the drive device 20 to pull out the injection needle 516 by a predetermined amount (step S540). In this manner, the injection step can be automatically controlled using machine learning based on the endoscopic image.

Note that machine learning of the second trained model 142 described later can be performed in a similar manner using the training device 80. In this case, the memory 830 of the training device 80 stores a second training model 842 and second training data 852. Then, the processor 800 performs machine learning on the second training model 842 using the second training data 852, such that the second training model 842 is updated as the second trained model 142 and is output to the surgical system 1. In addition, machine learning of the third trained model 143 described later can also be performed in a similar manner using the training device 80. In this case, the memory 830 of the training device 80 stores a third training model 843 and third training data 853. Then, the processor 800 performs machine learning on the third training model 843 using the third training data 853, such that the third training model 843 is updated as the third trained model 143 and is output to the surgical system 1. Further, machine learning of the fourth trained model 144 described later can be performed in a similar manner using the training device 80. In this case, the memory 830 of the training device 80 stores a fourth training model 844 and fourth training data 854. Then, the processor 800 performs machine learning on the fourth training model 844 using the fourth training data 854, such that the fourth training model 844 is updated as the fourth trained model 144 and is output to the surgical system 1. Further, machine learning of the fifth trained model 145 described later can be performed in a similar manner using the training device 80. In this case, the memory 830 of the training device 80 stores a fifth training model 845 and fifth training data 855. Then, the processor 800 performs machine learning on the fifth training model 845 using the fifth training data 855, such that the fifth training model 845 is updated as the fifth trained model 145 and is output to the surgical system 1. Yet further, machine learning of the sixth trained model 146 described later can be performed in a similar manner using the training device 80. In this case, the memory 830 of the training device 80 stores a sixth training model 846 and sixth training data 856. Then, the processor 800 performs machine learning on the sixth training model 846 using the sixth training data 856, such that the sixth training model 846 is updated as the sixth trained model 146 and is output to the surgical system 1.

Figure 26:
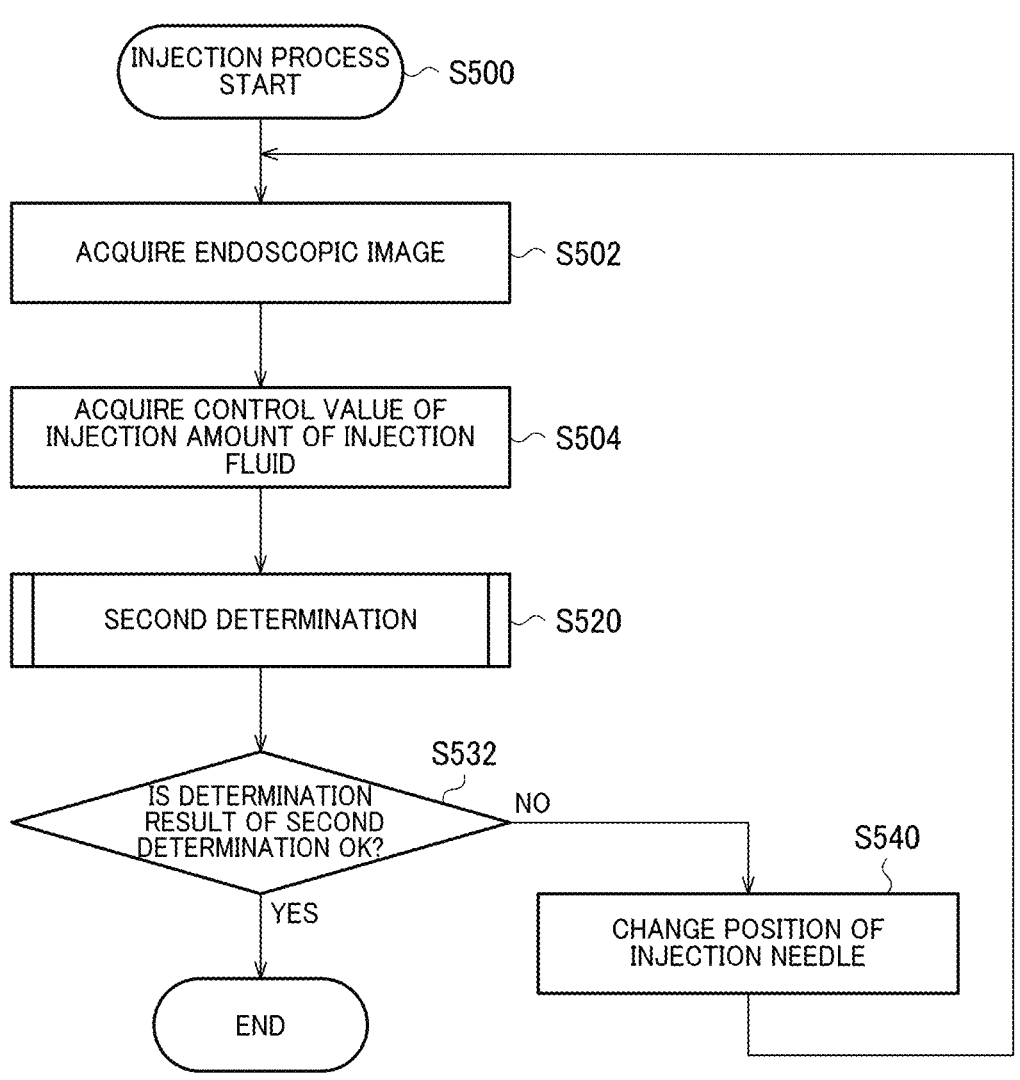
FIG. 26 is a flowchart illustrating another example processing of the injection process.

Further, for example, the injection process (step S500) of the present embodiment may be implemented as the example processing shown in the flowchart of FIG. 26. In this case, second determination (step S520) is performed as the prescribed determination of the present embodiment. Hereinafter, the second determination as the prescribed determination is simply referred to as second determination. After performing the aforementioned step S502, the processor 100 acquires a control value of the injection amount of the injection fluid (step S504). For example, the processor 100 acquires information indicative of the control value which is transmitted by the plunger drive section 212 to the syringe pump 214. Thereafter, the processor 100 performs the second determination (step S520) to confirm the determination result (OK or NG) of the second determination (step S532). When the determination result of the second determination is NG (NO in step S532), the processor 100 performs the aforementioned step S540 and performs the step S502 again.

Figure 27:
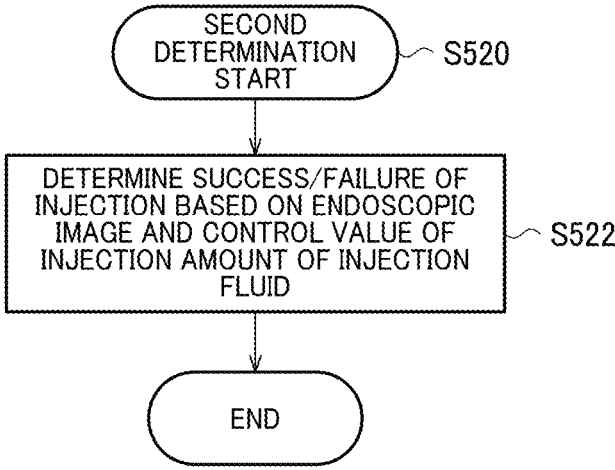
FIG. 27 is a flowchart illustrating example processing of second determination.

The second determination (step S520) determines, for example, as shown in the flowchart of FIG. 27, success/failure of the injection based on the endoscopic image acquired in the step S502 and the control value of the injection amount of the injection fluid acquired in the step S504 (step S522). That is, once the endoscopic image and the control value of the injection amount of the injection fluid are input to the control device 10 as the input data, the processor 100 outputs the determination result of success/failure of the injection. In other words, the step S522 in FIG. 27 is different from the step S512 in FIG. 19 in that the input data used for determination of success/failure of the injection is added.

For example, though not shown in the drawings, a physical model of the mucosa and the submucosal layer are stored in the memory 130. Then, the processor 100 calculates, for example, a first region based on the physical model, the first region being a region that will be raised when the injection fluid of the injection amount corresponding to the control value enters the submucosal layer. In addition, the processor 100 extracts, from the endoscopic image, a second region which is an actually raised region. Then, the processor 100 obtains the degree of coincidence between the first region and the second region, and when the degree of coincidence is equal to or greater than a predetermined reference value, the injection is successful so that the processor 100 determines OK in the second determination (step S520). Accordingly, the processor 100 determines YES in the step S532 and ends the injection process (step S500). On the other hand, when the degree of coincidence is less than the predetermined reference value, the processor 100 determines NG in the second determination (step S520) because the shape change of the treatment target is considered to be insufficient. Accordingly, the processor 100 determines NO in the step S532 and performs the aforementioned step S540 to change the position of the injection needle 516. Thereafter, when the second region changes and the degree of coincidence between the first region and the second region becomes equal to or greater than the predetermined reference value in the repeated step S522, the injection is successful due to the position change of the injection needle 516 so that the processor 100 determines OK in the second determination (step S520).

From the above, in the surgical system 1 of the present embodiment, the processor 100 determines success/failure of the injection further using the control value of the injection amount of the injection fluid in the prescribed determination (second determination (step S520)), and controls the drive device 20 to change the position of the injection needle 516 based on the determination result of the prescribed determination (NO in step S532, step S540). In this manner, the injection step can be automatically controlled based on the control value of the injection amount of the injection fluid and the endoscopic image.

Figure 28:
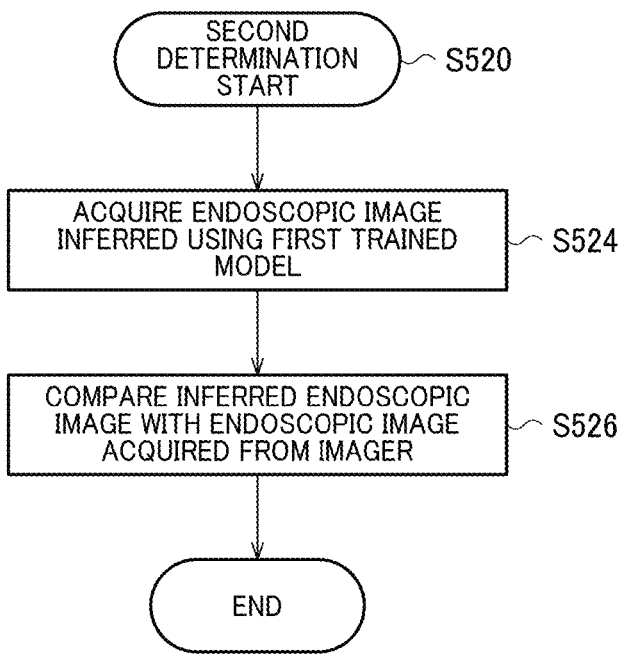
FIG. 28 is a flowchart illustrating another example processing of the second determination.
Figure 29:
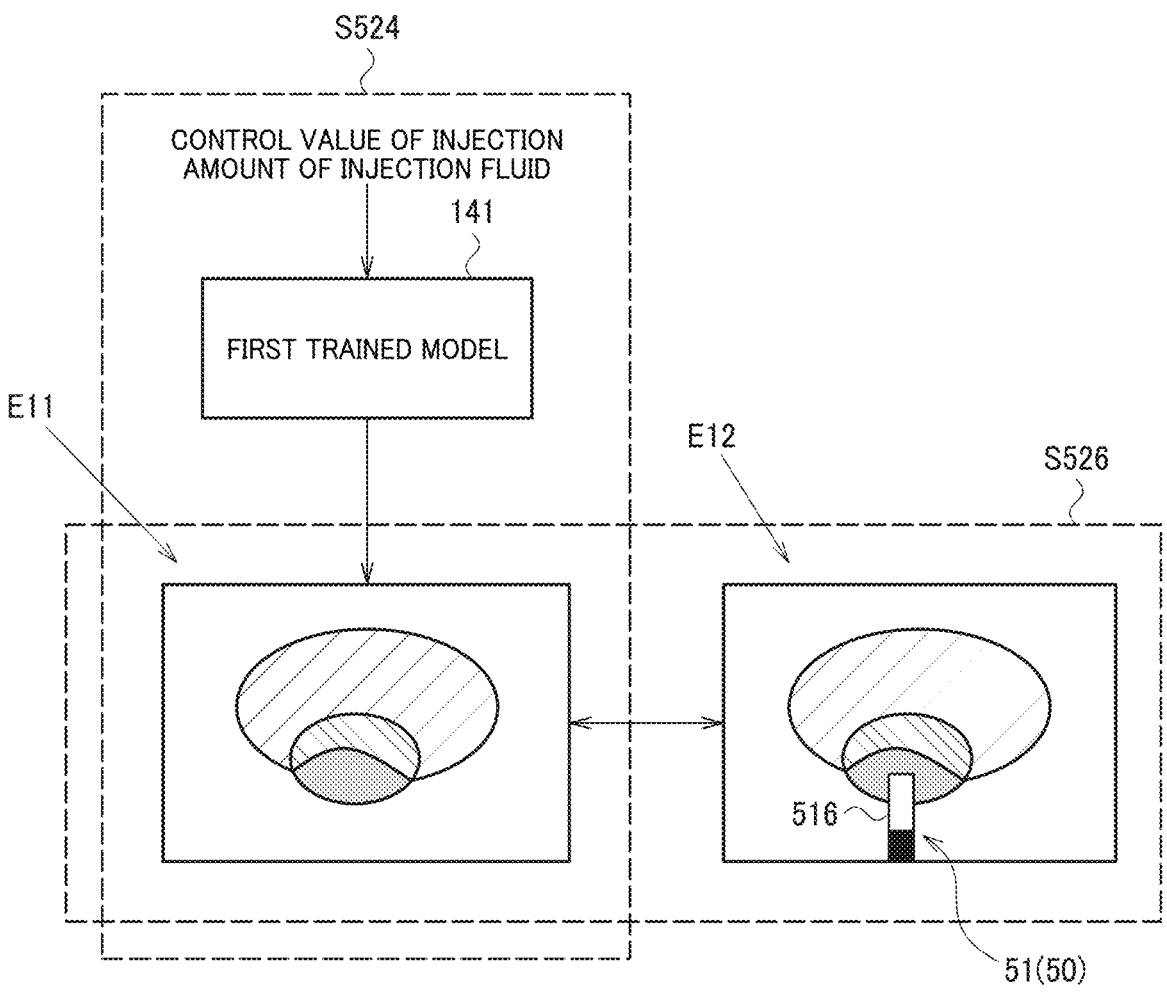
FIG. 29 is a diagram illustrating example data to be input to or output from a first trained model.

Further, for example, the second determination (step S520) may be implemented as the example processing shown in the flowchart of FIG. 28. In FIG. 28, the processor 100 acquires the endoscopic image inferred by using the first trained model 141 (step S524). Though the wording of the step S524 of FIG. 28 is the same as the step S514 of FIG. 23, the dataset used for inference is different. As shown in FIG. 29, the control value of the injection amount of the injection fluid acquired in the step S504 is to be the input data, and the inference section 102 uses the first trained model 141 to infer the endoscopic image including the raised lesion site based on the control value of the injection amount of the injection fluid. Note that the input data may include, for example, information indicative of the injection position as metadata. Then, as indicated by E11, for example, data of the endoscopic image inferred by the inference section 102 is to be the output data. That is, the dataset used for machine learning of the first trained model 141 in the second determination (step S520) in FIG. 28 is different from that of the first determination (step S510) in FIG. 23 in that it includes the endoscopic image as well as the control value of the injection amount of the injection fluid.

Note that FIG. 29 is a simplified view with only the input data, the first trained model 141, and the output data, illustrating that the input data is input to the input section 110, the processor 100 reads out the first trained model 141 from the memory 130, the inference section 102 performs inference based on the input data, and the inferred output data is output via the output section 120. The same applies to FIGS. 32, 35, 40, and 43 described later.

Thereafter, the processor 100 compares the inferred endoscopic image with the endoscopic image acquired from the imager 42 (step S526). That is, the endoscopic image indicated by E11 in FIG. 29 is compared with the endoscopic image in which the injection needle 516 is actually inserted to perform the injection as indicated by E12. Note that a process of excluding a part of the endoscopic image indicated by E12, in which the injection needle 516 and the like is captured, from the comparison may be added. Then, for example, when similarity between the endoscopic image indicated by E11 and the endoscopic image indicated by E12 is less than a predetermined threshold, the shape change of the treatment target is insufficient so that the processor 100 determines NG in the second determination (step S520). In this case, the processor 100 determines NO in the step S532 and performs the aforementioned step S540. Thereafter, when the similarity between the endoscopic image indicated by E11 and the endoscopic image indicated by E12 becomes the predetermined threshold or greater in the repeated step S522, the injection is successful so that the processor 100 determines OK in the second determination (step S520), determines YES in the subsequent step S532, and ends the injection process (step S500).

Figure 30:
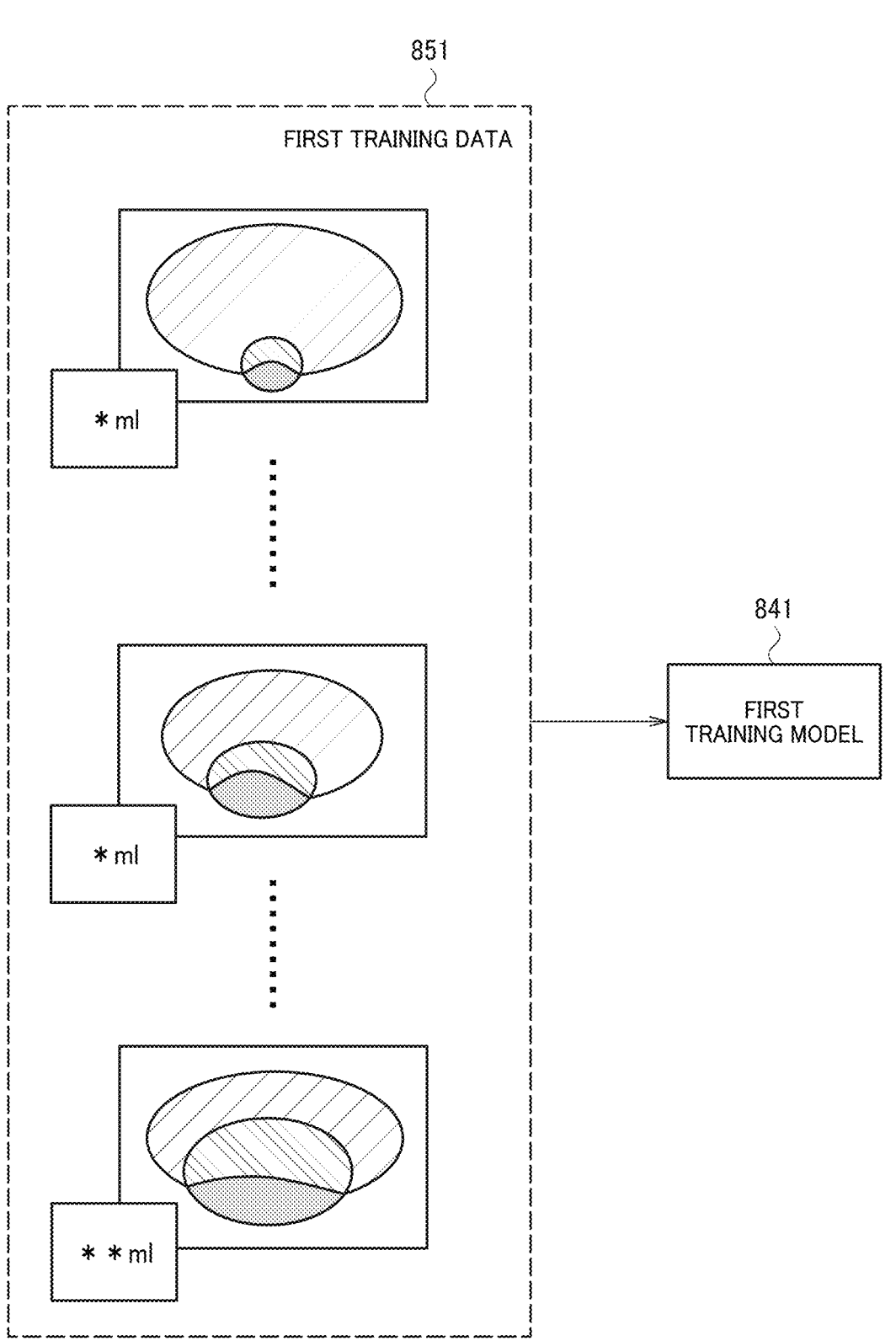
FIG. 30 is a diagram illustrating an example of first training data.

The first training data 851 in this case is, for example, a dataset in which the endoscopic image data as the ground truth label, in which the lesion site into which the target amount of the injection fluid was injected is captured, is associated with data of the target injection amount of the injection fluid as shown in FIG. 30. The machine learning section 802 inputs such first training data 851 to the first training model 841, thereby updating the first trained model 141.

Note that for example, the first training data 851 may further add, to the above data, endoscopic image data in which the lesion site before injecting the injection fluid is captured. That is, the first training data 851 may be a dataset in which the endoscopic image data as the ground truth label, in which the lesion site into which the target amount of the injection fluid was injected is captured, is associated with data including a combination of the data of the target amount injection of the injection fluid and the endoscopic image data in which the lesion site before injecting the injection fluid is captured. Then, the inference section 102 uses the first trained model 141 trained based on such first training data 851 to infer the endoscopic image including the raised lesion site based on the control value of the injection amount of the injection fluid acquired in the step S504 and the endoscopic image data in which the lesion site before injecting the injection fluid is captured.

Further, for example, though not shown in the drawings, the first training data 851 may be a dataset in which a value of area of the raised region after the injection as the ground truth label is associated with the data of the target amount injection of the injection fluid. Alternatively, a value of volume of the raised site after the injection may be the ground truth label. Then, the inference section 102 uses first trained model 141 trained based on such first training data 851 to infer the area of the raised region and the like based on the control value of the injection amount of the injection fluid acquired in the step S504. Then, the processor 100 performs processes of extracting the raised region from the endoscopic image, obtaining the degree of coincidence of the area and the like between the extracted region and the inferred region, and determining whether or not the obtained degree of coincidence is equal to or greater than the predetermined reference value. When the obtained degree of coincidence is equal to or greater than the predetermined reference value, the processor 100 determines OK in the second determination (step S520), determines YES in the subsequent step S532, and ends the injection process (step S500).

As a result, the surgical system 1 of the present embodiment includes the first trained model 141 trained based on learning data (first training data 851) including the injection amount of the injection fluid and the endoscopic image in which the treatment target, into which the injection fluid corresponding to the injection amount was injected, is captured. The processor 100 uses the first trained model 141 to determine, based on the endoscopic image, sufficiency of the shape change of the treatment target for the control value, and controls the drive device 20 to pull out the injection needle 516 by the predetermined amount (step S540) when the shape change of the treatment target is insufficient (NO in step S532). In this manner, the injection step can be automatically controlled using the control value of the injection amount of the injection fluid and machine learning using the endoscopic image.

Further, for example, measurement by a sensor provided around the syringe 512 may be performed in conjunction with the first determination (step S510) described above with reference to FIG. 19 or the second determination (step S520) described above with reference to FIG. 27, thereby determining success/failure of the injection. As described above with reference to FIG. 20, when the distal end of the injection needle 516 is located within the muscle layer indicated by L3 in FIG. 20, the injection fluid does not enter. Accordingly, even if the syringe pump 214 pushes the plunger 514 based on the control value transmitted to the syringe pump 214 by the plunger drive section 212, the force of the syringe pump 214 pushing the plunger 514 is in balance with the resistance received by the syringe pump 214 from the plunger 514, so that the plunger 514 appears to be stationary.

Therefore, though detailed illustration is omitted, a force sensor which measures the resistance from the plunger 514 is provided, for example, on the part of the syringe pump 214 indicated by B11 in FIG. 7. Then, the processor 100 determines, based on the endoscopic image, whether or not the shape change of the treatment target is caused by injection of the injection fluid as described above, and measures a detection value of the force sensor. When the distal end of the injection needle 516 is located within muscle layer, it is considered that the resistance from the plunger 514 is equal to an upper limit value of the force of the syringe pump 214 pushing the plunger 514. Hence, for example, a value obtained by multiplying the upper limit value by a predetermined percentage is set as a first predetermined value, and when the resistance measured by the force sensor becomes equal to or greater than the first predetermined value, it can be determined that the distal end of the injection needle 516 is located within the muscle layer. This can further support the determination result in a case that the determination result of the first determination (step S510) or the second determination (step S520) is NG.

On the other hand, when the resistance measured by the force sensor is less than the first predetermined value, the plunger 514 is moving forward, and thus, it can be determined that the distal end of the injection needle 516 is located within the submucosal layer indicated by L2 in FIG. 21. As a result, the processor 100 determines YES as the determination result of the second determination (step S520), and the flow of the injection process (step S500) ends. That is, the surgical system 1 of the present embodiment includes the force sensor that can detect the resistance upon injection of the injection fluid into the treatment target. When the shape change of the treatment target is insufficient and the detection value of the force sensor is equal to or greater than the first predetermined value (NO in step S531, NO in step S532), the processor 100 controls the drive device 20 to pull out the injection needle 516 by the predetermined amount (step S540). This enables more accurate determination of success/failure of the injection based on the measurement result of the resistance from the syringe 512.

Alternatively, though not shown in the drawings, a position sensor that can detect a displacement amount of the plunger 514 may be used. The plunger 514 can be displaced within the range indicated by D18 in FIG. 7. The position sensor herein may be a range sensor or an encoder. When the distal end of the injection needle 516 is located within the muscle layer indicated by L3 in FIG. 20 as described above, it is considered that the plunger 514 has hardly moved. Therefore, for example, a detection value of the position sensor corresponding to the displacement amount, based on which the plunger 514 is considered to be not substantially moving forward, is set as a second predetermined value. Then, when the measured detection value of the position sensor is less than the second predetermined value, it can be determined that the distal end of the injection needle 516 is located within the muscle layer because the plunger is not substantially moving forward. This can further support the determination result in a case that the determination result of the first determination (step S510) or the second determination (step S520) is NG.

In other words, the surgical system 1 of the present embodiment includes the position sensor that can detect the displacement amount of the plunger 514. When the shape change of the treatment target is insufficient and the detection value of the position sensor is less than the second predetermined value (NO in step S531, NO in step S532), the processor 100 controls the drive device 20 to pull out the injection needle 516 by the predetermined amount (step S540). This enables more accurate determination of success/failure of the injection based on the measurement result of the movement amount of the plunger 514.

Figure 31:
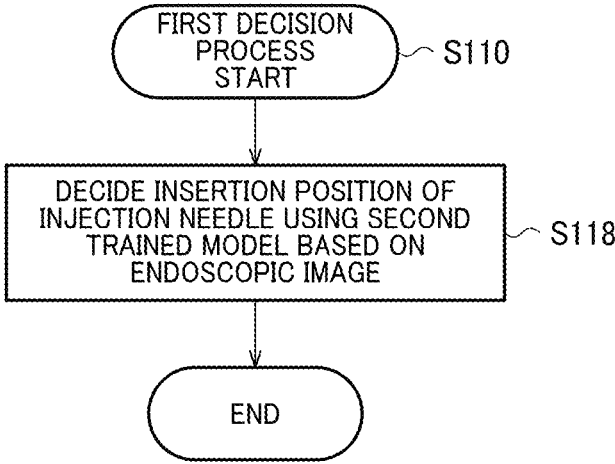
FIG. 31 is a flowchart illustrating example processing of a first decision process.

Further, instead of the aforementioned step S100, for example, a first decision process (step S110) may be performed, which decides the insertion position of the injection needle 516 by machine learning. The example processing of the first decision process (step S110) will be described using the flowchart in FIG. 31. The processor 100 uses the second trained model 142 to decide, based on the endoscopic image, where to insert the injection needle 516 (step S118).

Figure 32:
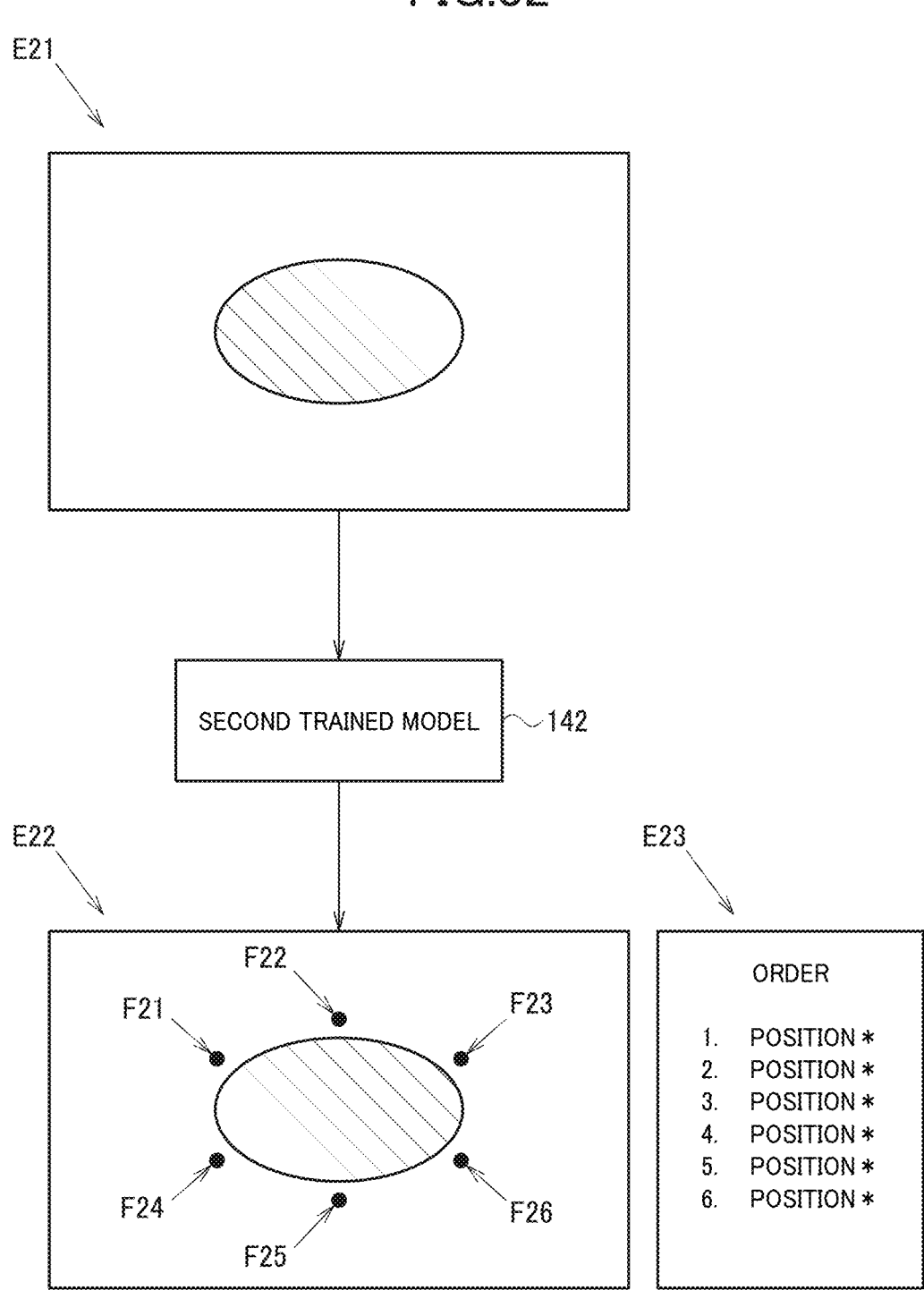
FIG. 32 is a diagram illustrating example data to be input to or output from a second trained model.

For example, as indicated by E21 in FIG. 32, the endoscopic image in which the lesion site as the treatment target is captured is input to the input section 110 as the input data. Then, the inference section 102 performs inference using the second trained model 142, and the endoscopic image with the information indicative of the injection positions added as indicated by E22 is output from the output section 120. More specifically, in the endoscopic image indicated by E22, position information indicated by F21, position information indicated by F22, position information indicated by F23, position information indicated by F24, position information indicated by F25, and position information indicated by F26 are added around the lesion site.

Further, as indicated by E23 in FIG. 32, order information indicative of order of inserting the injection needle 516 is output from the output section 120 as the output data. For example, the position indicated by F21 is displayed as a first insertion position of the injection needle 516, the position indicated by F22 is displayed as a second insertion position of the injection needle 516, and the position indicated by F23 is displayed as a third insertion position of the injection needle 516. In addition, the information indicative of the order indicated by E23 is displayed with the position indicated by F24 as a fourth insertion position of the injection needle 516, the position indicated by F25 as a fifth insertion position of the injection needle 516, and the position indicated by F26 as a sixth insertion position of the injection needle 516.

Figure 33:
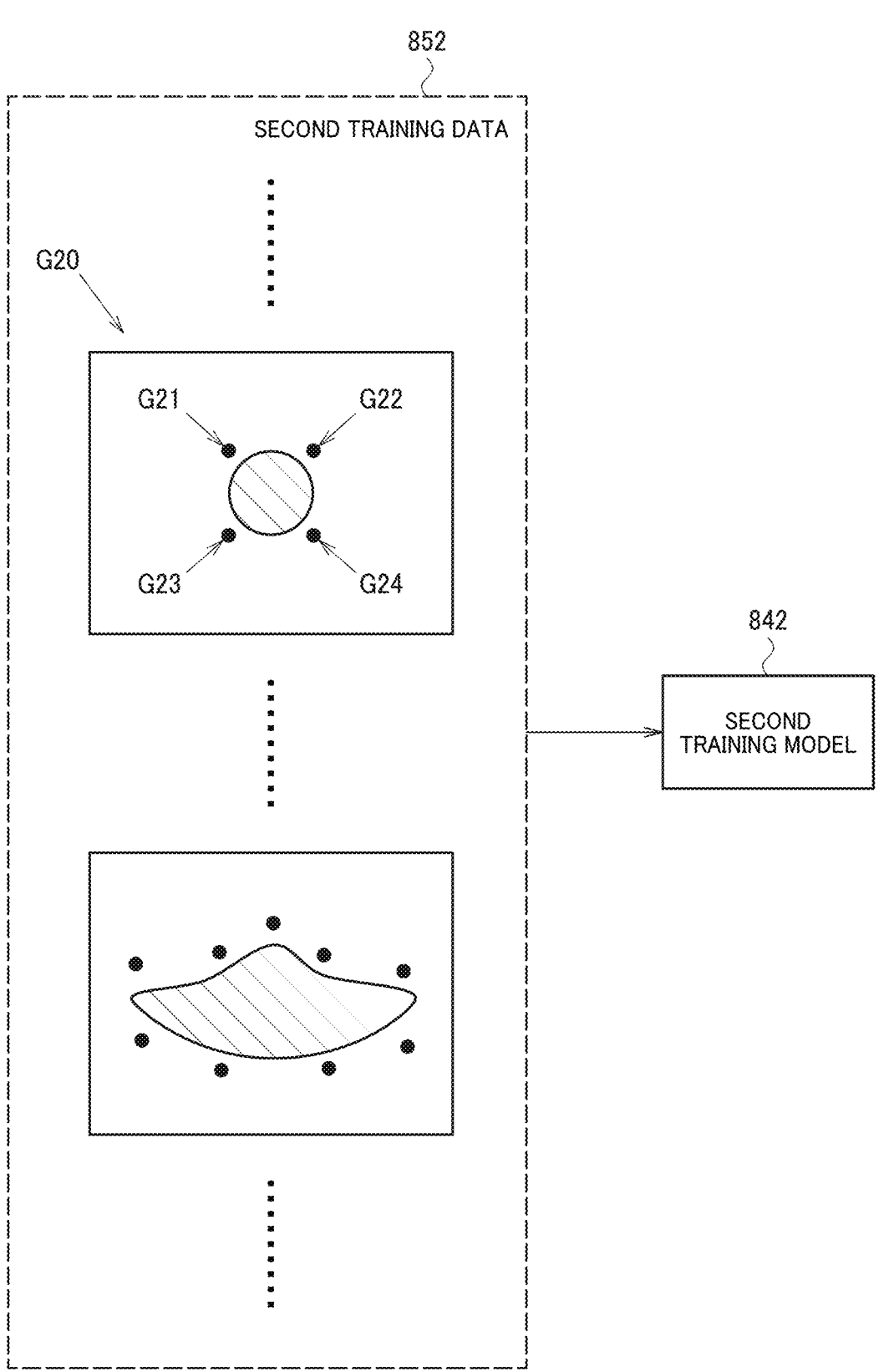
FIG. 33 is a diagram illustrating an example of second training data.

The second trained model 142 is generated, as shown in FIG. 33, by performing machine learning on the second training model 842 using the second training data 852 as the dataset. The second training data 852 is a dataset in which the information indicative of the injection positions as the ground truth label is associated with the endoscopic image in which the lesion site is captured, based on past cases. The second training data 852 includes numerous data including a combination of the lesion sites of various shapes and the injection positions for the lesion sites. In addition, the order information may be further added to the second training data 852 as the ground truth label. For example, the data indicated by G20 in FIG. 33 is based on the case where the injection needle 516 was inserted into the lesion site in the order of the positions indicated by G21, G22, G23, and G24.

From the above, the surgical system 1 of the present embodiment includes the second trained model 142 trained based on the learning data including the endoscopic image in which the treatment target is captured, and the information indicative of the insertion position of the injection needle 516. The processor 100 uses the second trained model 142 to perform the first decision process (step S110) based on the endoscopic image to decide the insertion position of the injection needle 516. In this manner, it is possible to automatically decide where to insert the injection needle 516 in the treatment of ESD and the like.

Figure 34:
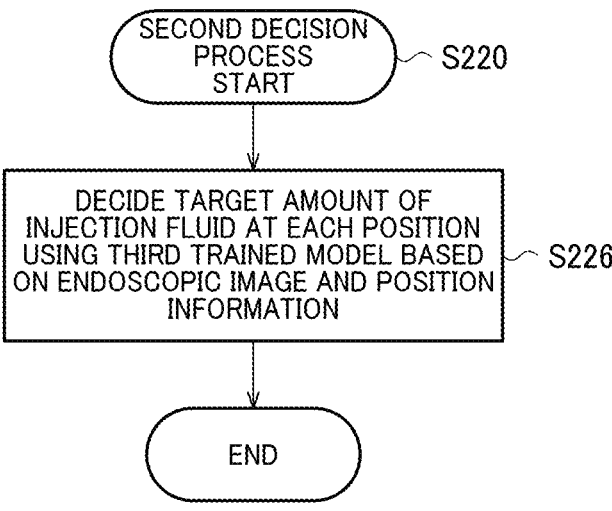
FIG. 34 is a flowchart illustrating example processing of a second decision process.

Further, instead of the aforementioned step S200, for example, a second decision process (step S220) may be performed, which decides the target amount of the injection fluid by machine learning. The example processing of the second decision process (step S220) will be described using the flowchart in FIG. 34. The processor 100 uses the third trained model 143 to decide, based on the endoscopic image and the position information, the target amount of the injection fluid at each position (step S226). For example, as indicated by E31 and E32 in FIG. 35, data including the endoscopic image, the position information, and the order information output by the aforementioned step S118 is input to the input section 110. That is, the data output from the output section 120 by inference according to the step S110 is input to the input section 110 as it is.

Figure 35:
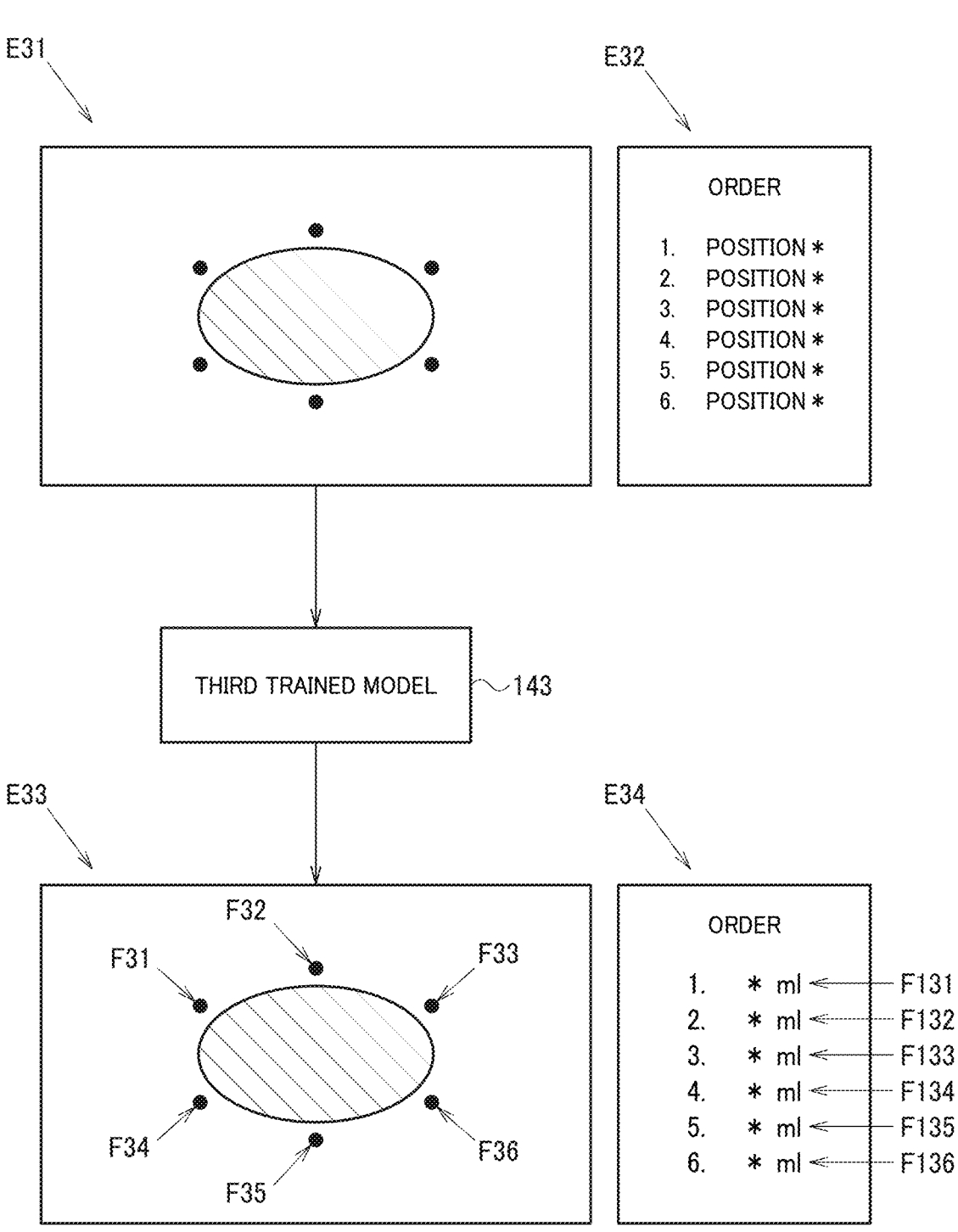
FIG. 35 is a diagram illustrating example data to be input to or output from a third trained model.

Then, the inference section 102 reads out the third trained model 143 to perform inference, and the endoscopic image indicated by E33 in FIG. 35 and the position information as well as the target amount of the injection fluid at each position as indicated by E34 are output from the output section 120 as the output data. For example, the target amount indicated by F131 is displayed for the position indicated by F31, the target amount indicated by F132 is displayed for the position indicated by F32, the target amount indicated by F133 is displayed for the position indicated by F33, the target amount indicated by F134 is displayed for the position indicated by F34, the target amount indicated by F135 is displayed for the position indicated by F35, and the target amount indicated by F136 is displayed for the position indicated by F36.

Figure 36:
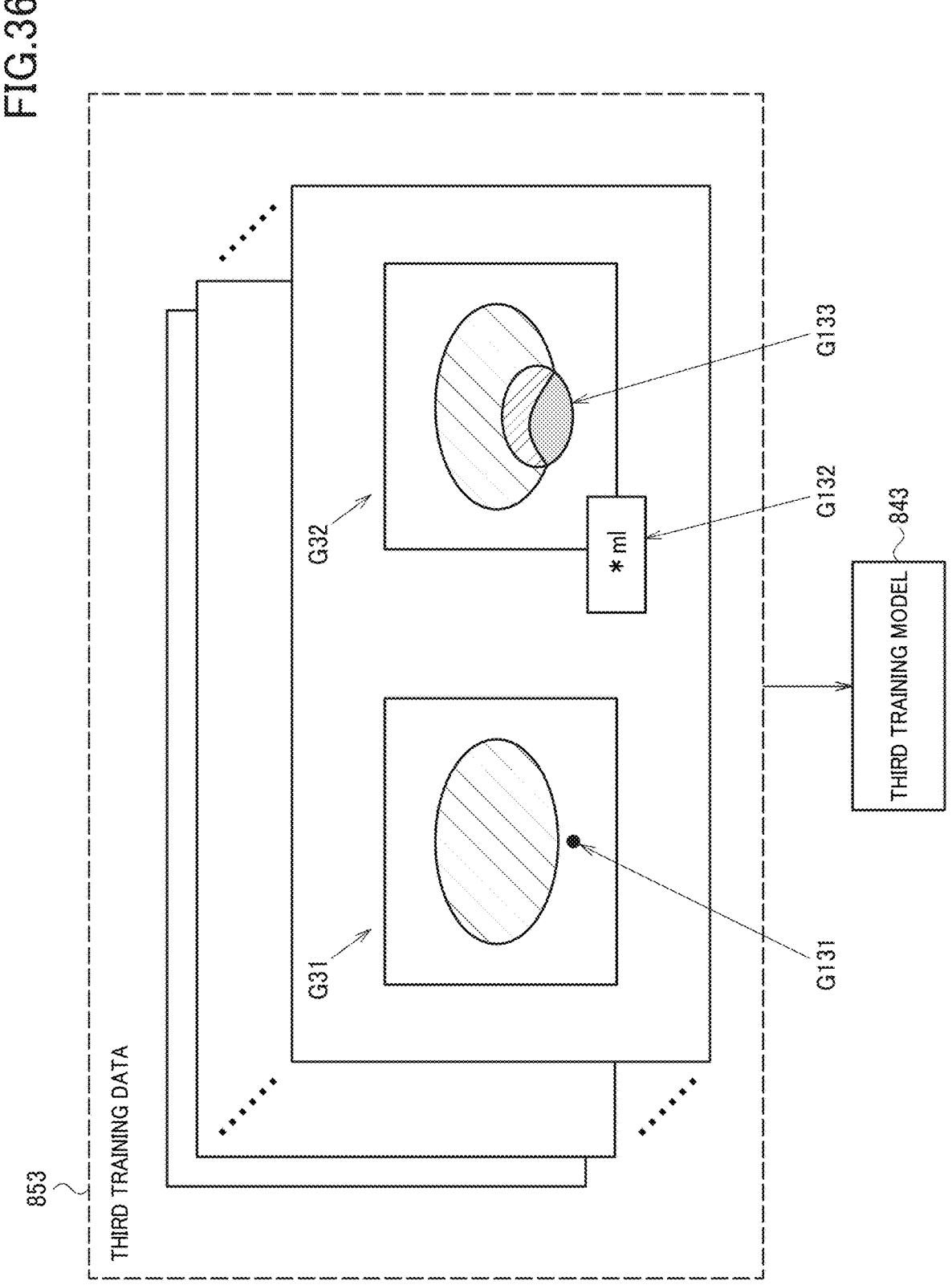
FIG. 36 is a diagram illustrating an example of third training data.

The third trained model 143 is generated, as shown in FIG. 36, by performing machine learning on the third training model 843 using the third training data 853 as the dataset. In the third training data 853, the endoscopic image indicated by G31 is associated with the information about the endoscopic image indicated by G32 as the ground truth label. The endoscopic image indicated by G31 includes the image of the lesion site and the information indicative of the injection position indicated by G131. The endoscopic image indicated by G32 is the image after performing the injection into the injection position indicated by G131. More specifically, it is the endoscopic image in which the information indicative of the injection amount of the injection fluid indicated by G132 is associated with the image information about the raised lesion site due to the injection amount indicated by G133.

From the above, the surgical system 1 of the present embodiment includes the third trained model 143 trained based on the learning data (third training data 853) including the endoscopic image in which the treatment target is captured, the information indicative of the insertion position of the injection needle 516, and the target amount of the injection fluid corresponding to the position information. The processor 100 uses the third trained model 143 to perform the second decision process (step S220) which decides the target amount of the injection fluid at each insertion position of the injection needle 516 based on the endoscopic image and the position information decided in the first decision process (step S110). In this manner, it is possible to automatically decide the target amount of the injection fluid at each insertion position of the injection needle 516.

Figure 37:
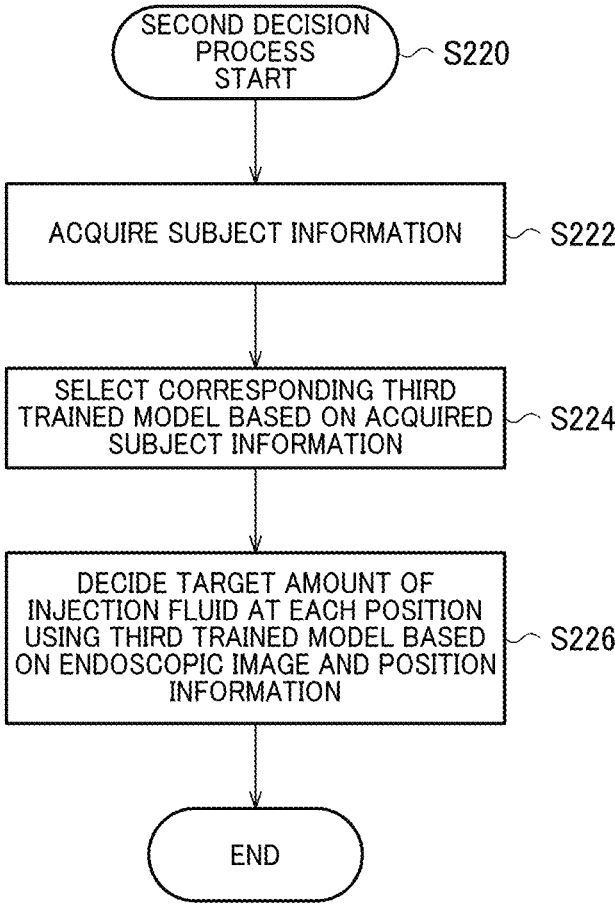
FIG. 37 is a flowchart illustrating another example processing of the second decision process.

Note that there may be a plurality of third trained models 143. Specifically, for example, a subject may be classified into a plurality of categories considering sex, age, and the like, and the third trained models 143 corresponding to respective categories may be stored in the memory 130. In this case, the second decision process (step S220) may be implemented as the example processing shown in the flowchart of FIG. 37. The processor 100 acquires subject information (step S222), and selects the corresponding third trained model 143 based on the acquired subject information (step S224). More specifically, a user inputs information indicating that the subject is a female in her 40s from a medical record to the control device 10 and stores in the memory 130. Then, in the step S222, the processor 100 acquires the information indicating that the subject is a female in her 40s. Then, in the step S224, the processor 100 reads out the third trained model 143 corresponding to a female in her 40s from the memory 130. Thereafter, the processor 100 performs the process of the aforementioned step S226 using the third trained model 143 read out in the step S224.

Further, though not shown in the drawings, for example in FIG. 35, the information indicated by E33 may be three-dimensional shape information that has changed due to the injection performed at each position, instead of the injection amount of the injection fluid at each position. That is, a target indicator is how much the area around the inserted injection needle 516 is to be raised by performing the injection into each insertion position of the injection needle 516. In this case, the third training data 853 may associate the three-dimensional shape information that has changed due to the injection performed, instead of the injection amount of the injection fluid indicated by G132 in FIG. 36, in the dataset described above with reference to FIG. 36.

Figure 38:
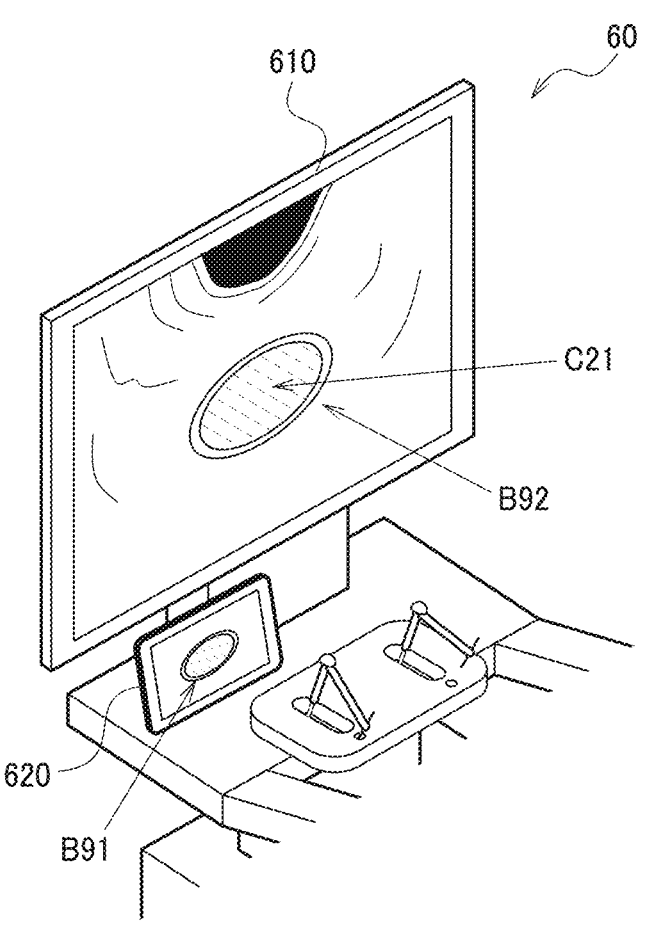
FIG. 38 is a diagram illustrating an example in which a touch panel is used to acquire an endoscopic image.

Further, the endoscopic image indicated by E21 in FIG. 32 may be acquired using the touch panel 620 of the console 60. Specifically, as shown in FIG. 38, for example, suppose that the lesion site indicated by C21 is displayed on the display 610 and also displayed on the touch panel 620. In this case, a user operates the touch panel 620 to enclose the area around the lesion site with an icon of a predetermined shape indicated by B91. Note that the predetermined shape is an ellipse in FIG. 38, but may be a polygon, or the user may be able to create a given shape by using a drawing function. In addition, it is possible that the icon of the predetermined shape indicated by B91 may be displayed on the display 610 as indicated by B92. Then, it is possible that, through the first decision process (step S110) and the second decision process (step S220) described above, the position information indicated by E32 and the information indicative of the injection amount of the injection fluid indicated by E33 in FIG. 35 may be displayed on the display 610. From the above, in the surgical system 1 of the present embodiment, the processor 100 decides, based on the endoscopic image, the insertion position of the injection needle 516 in the treatment target and the target amount of the injection fluid corresponding to the insertion position of the injection needle 516. In this manner, it is possible to construct a system which automatically decides the insertion position of the injection needle 516 and the injection amount of the injection fluid at the position by acquiring the endoscopic image.

Further, the direction information related to the step S300 in FIG. 14 etc. may be set using machine learning. Specifically, for example, the processor 100 may perform a third decision process (step S330) shown in the flowchart of FIG. 39, instead of the step S300.

The processor 100 acquires the output data from the aforementioned third trained model 143 (step S332). That is, the data output from the output section 120 by inference in accordance with the step S220 is input to the input section 110 as it is. Thereafter, the processor 100 decides the direction information about the injection needle 516 using the fourth trained model 144 (step S334).

For example, the data indicated by E41 and E42 in FIG. 40 is input to the input section 110. The data indicated by E41 and E42 in FIG. 40 corresponds to the data indicated by E22 and E23 in FIG. 32. Then, the inference section 102 performs inference using the fourth trained model 144. As a result, as indicated by E43, data is output via the output section 120, wherein in the data, the injection position included in the data of E41 is associated with the injection needle direction information indicative of the direction of the injection needle 516 when performing the aforementioned injection process (step S500).

Figure 41:
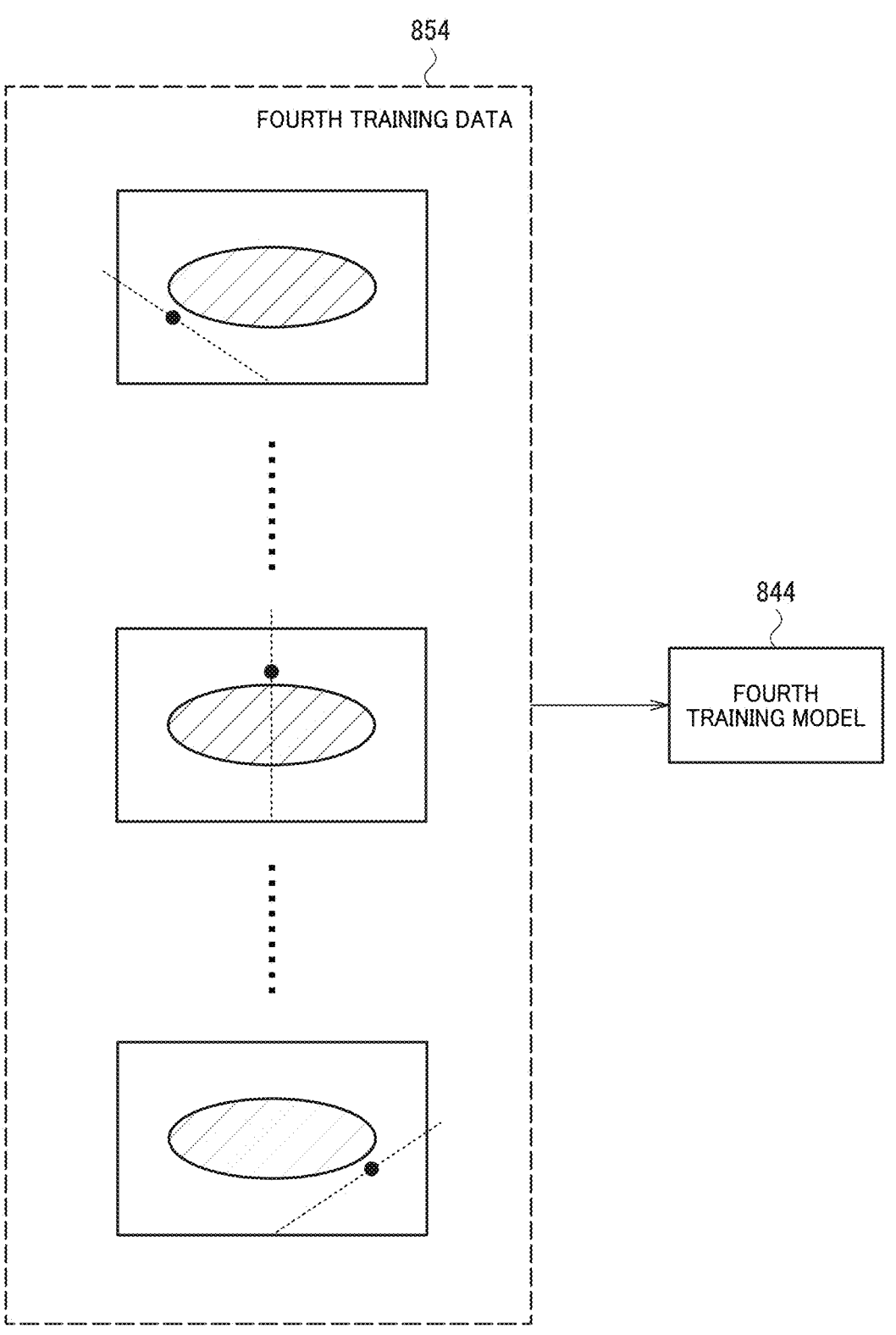
FIG. 41 is a diagram illustrating an example of fourth training data.

The fourth trained model 144 is generated, as shown in FIG. 41, by performing machine learning on the fourth training model 844 using the fourth training data 854 as the dataset. The fourth training data 854 is a dataset in which the endoscopic image including the information indicative of the injection position is associated with the injection needle direction information corresponding to the position as the ground truth label.

Figure 39:
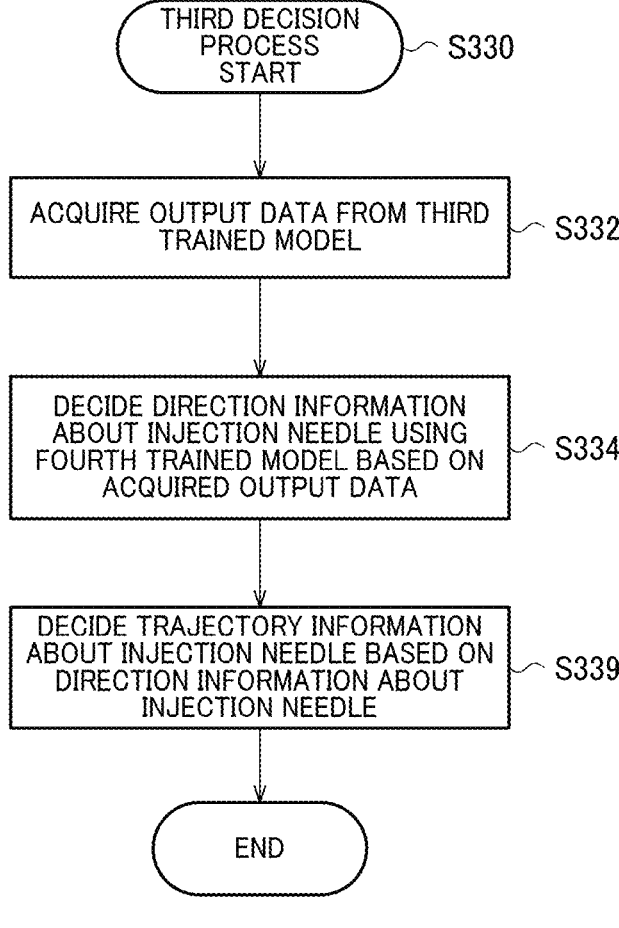
FIG. 39 is a flowchart illustrating example processing of a third decision process.

Return to the description of FIG. 39. After performing the aforementioned step S334, the processor 100 decides trajectory information about the injection needle 516 based on the direction information about the injection needle 516 (step S339). In other words, a calculation process of parameters for controlling the drive device 20 is performed to make the position information on the image acquired by the first decision process (step S110), the second decision process (step S220), and the third decision process (step S330) correspond to coordinate information about the endoscope 40 and the like in actual treatment. As such, the position where the injection process (step S500) is to be performed, the amount of the injection fluid, and drive information about the endoscope 40 and the first medical manipulator 510 are obtained, and the control device 10 controls the drive device 20 in accordance with such information, thereby achieving automatic control of the injection.

Figure 42:
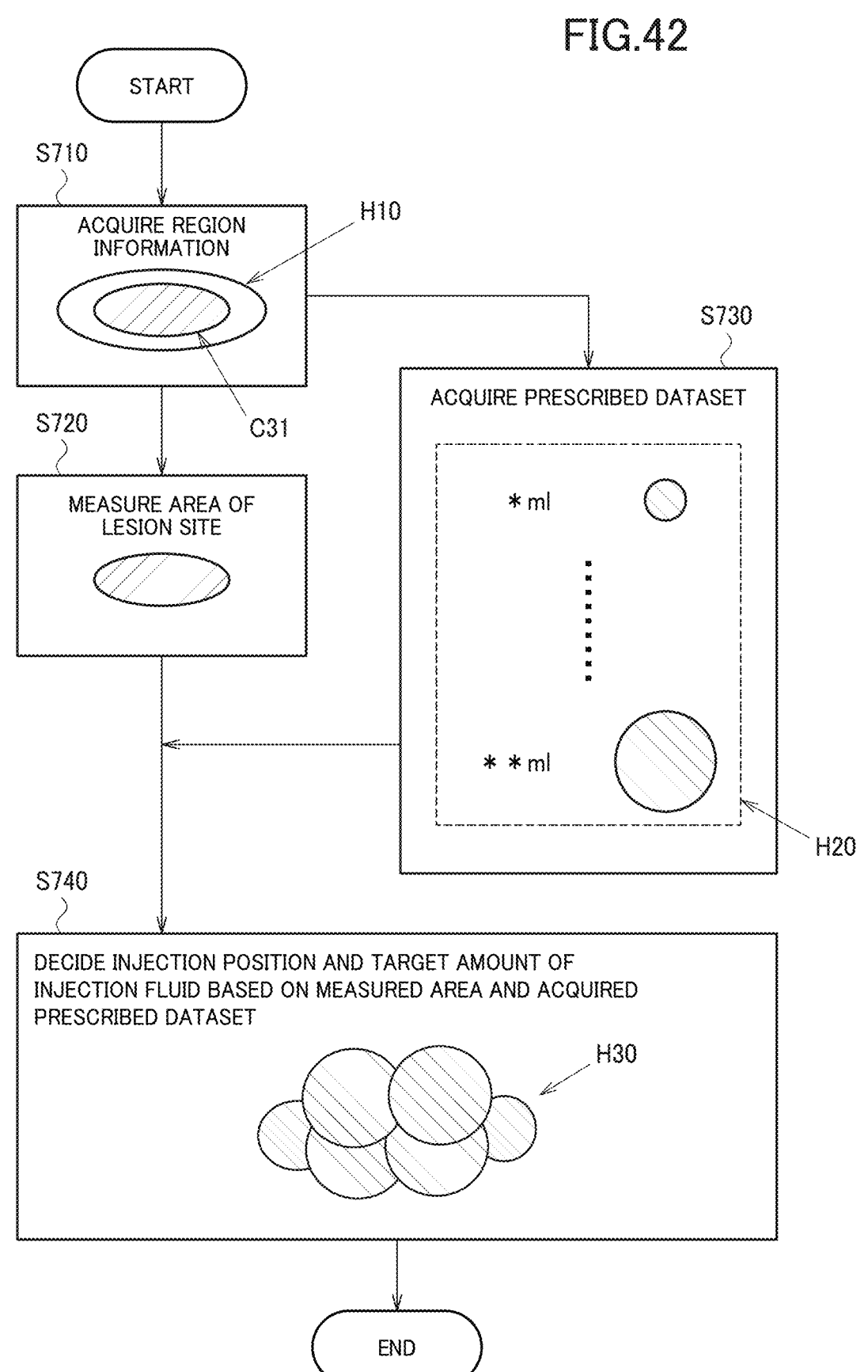
FIG. 42 is a diagram illustrating another technique for deciding position information and a target amount of a injection fluid.

Further, for example, by performing the example processing shown in FIG. 42 instead of the step S100 and the step S200 described above with reference to FIG. 14, etc., the position where the injection is to be performed and the target amount of the injection fluid at the position may be set. The processor 100 acquires region information (step S710). For example, as described above, a user uses the touch panel 620 to designate around the lesion site as the treatment target indicated by C31 with the predetermined shape indicated by H10, and the processor 100 acquires a region associated with the predetermined shape as the region information.

After performing the step S710, the processor 100 measures area of the lesion site included in the region information (step S720). In addition, after performing the step S710, the processor 100 acquires a prescribed dataset indicated by H20 based on the region information (step S730). Though the details of the step S730 will be described later, the prescribed dataset is, for example, a dataset in which the target amount of the injection is associated with a predetermined image corresponding to the target amount, which shows the shape change resulting from raising. That is, when the target amount of the injection fluid is small, it is associated with the small predetermined image, whereas when the target amount of the injection fluid is large, it is associated with the large predetermined image.

The processor 100 performs a step S740 based on the step S720 and the step S730, and ends the flow. The step S740 sets the injection position and the target amount of the injection fluid based on the area measured in the step S720 and the prescribed dataset acquired in the step S730.

Then, as indicated by H30, the size and arrangement of the predetermined image are decided such that the entire lesion site indicated by C31 will be raised. In this manner, it is possible to understand into which position relative to the lesion site and how much the injection fluid is to be injected so as to raise the entire lesion site.

The step S730 will be conceptually described with reference to FIG. 43. Once data of the region information acquired in the step S710 is input to the input section 110, the processor 100 reads out the fifth trained model 145 from the memory 130. Then, the inference section 102 outputs, based on the fifth trained model 145, data of features of the tissue associated with the region information via the output section 120. The features of the tissue refer to, for example, viscoelasticity of the tissue, tissue thickness, and the like.

Further, the output data of the features of the tissue is again input to the input section 110, and the processor 100 reads out the sixth trained model 146 from the memory 130. Then, the inference section 102 outputs, based on the sixth trained model 146, the prescribed dataset corresponding to the features of the tissue via the output section 120.

Figure 44:
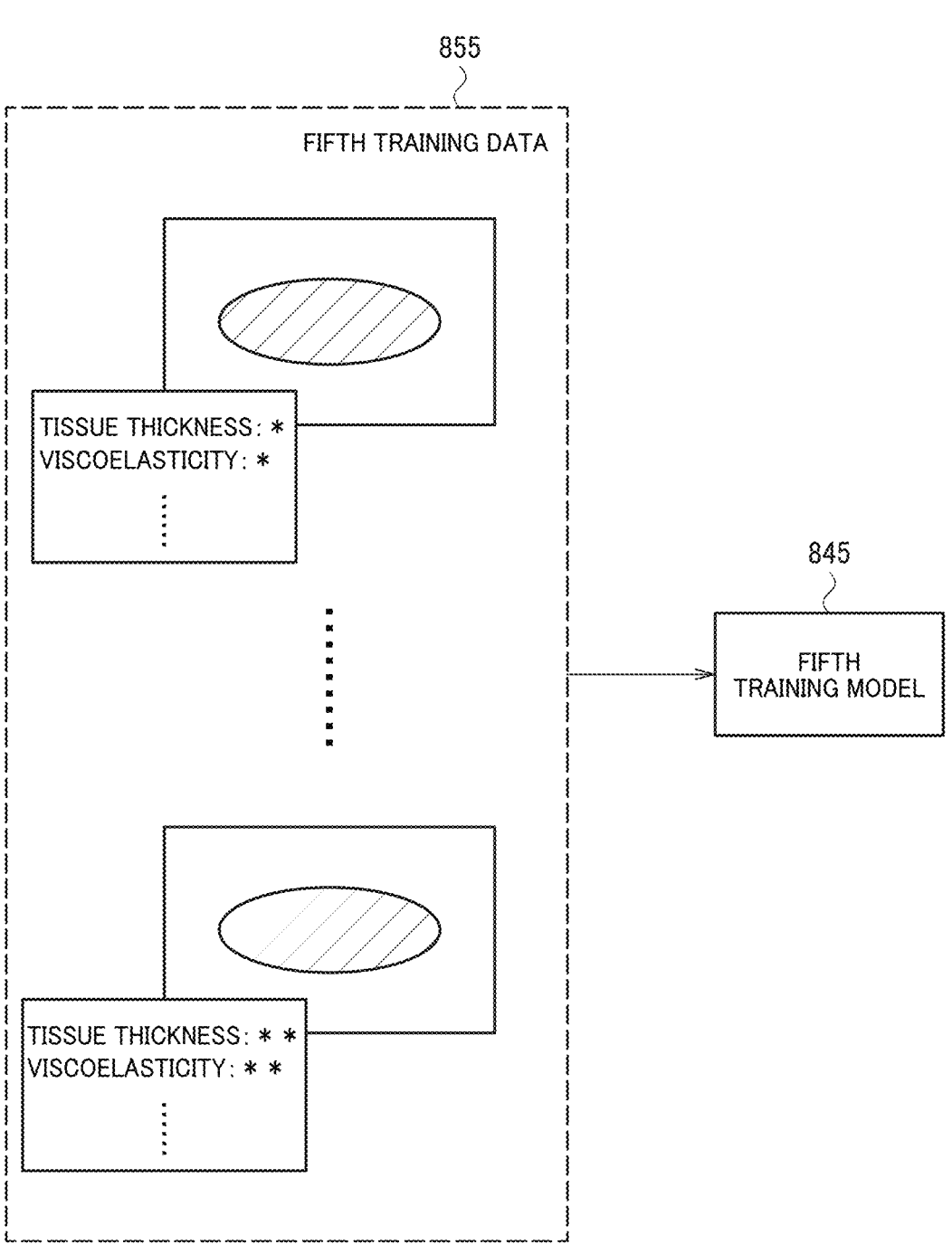
FIG. 44 is a diagram illustrating an example of fifth training data.

The fifth trained model 145 is generated by performing machine learning on the fifth training model 845 using the fifth training data 855 as the dataset as shown in FIG. 44. The fifth training data 855 is a dataset in which the endoscopic image in which a tissue including the lesion site is captured is associated with the information of the features about the tissue as the ground truth label.

Figure 45:
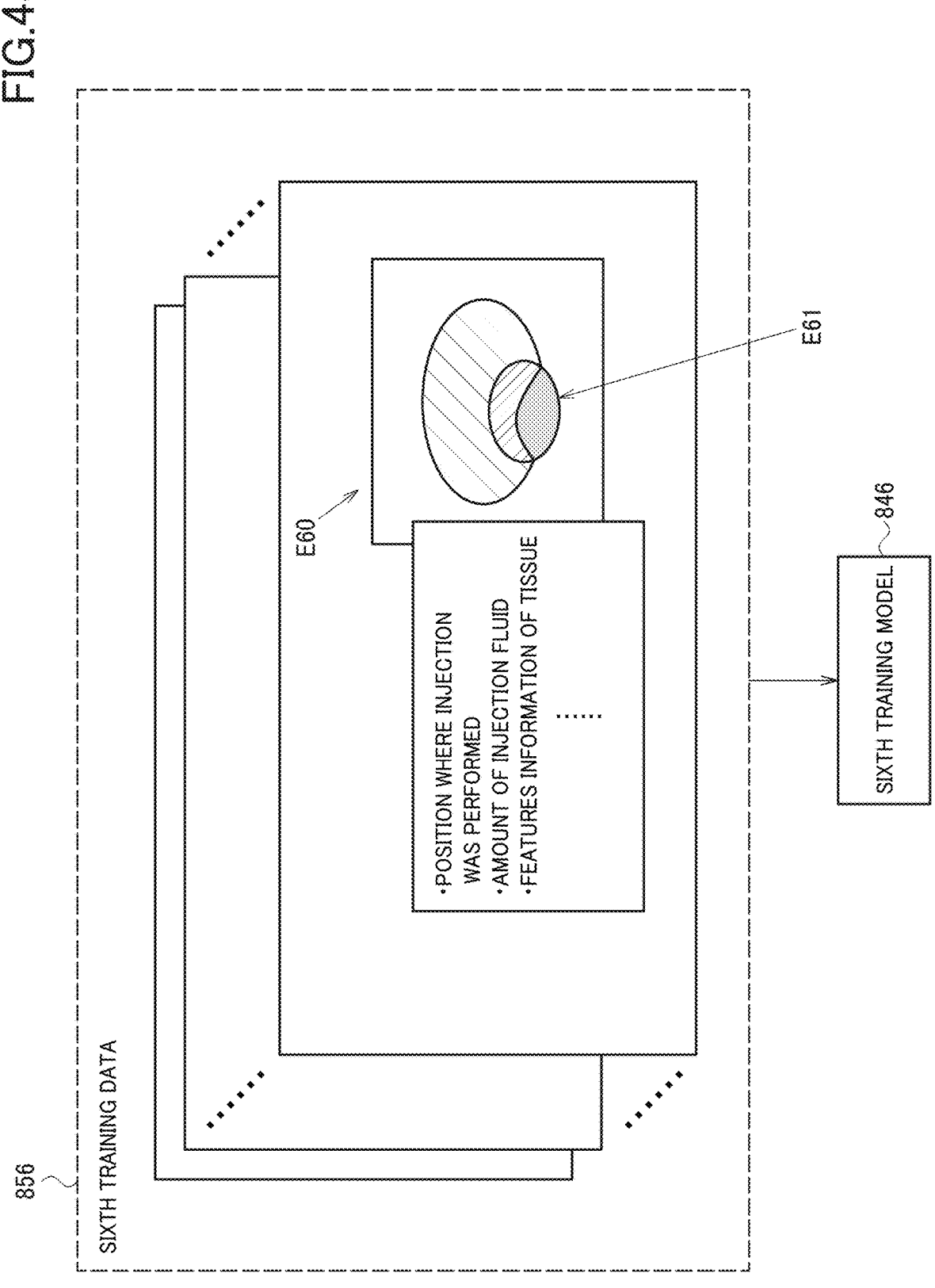
FIG. 45 is a diagram illustrating an example of sixth training data.

The sixth trained model 146 is generated, as shown in FIG. 45, by performing machine learning on the sixth training model 846 using the sixth training data 856 as the dataset. The sixth training data 856 is a dataset in which prescribed data described below as the ground truth label is associated with the features information of the tissue. The prescribed data is, for example, information indicative of the height and size of the raised site indicated by E61, information indicative of the position where the injection was performed, information indicative of the injection amount of the injection fluid, and the like extracted from the endoscopic image, which shows that the tissue including the lesion site is raised by performing the injection, as indicated by E60.

Figure 46:
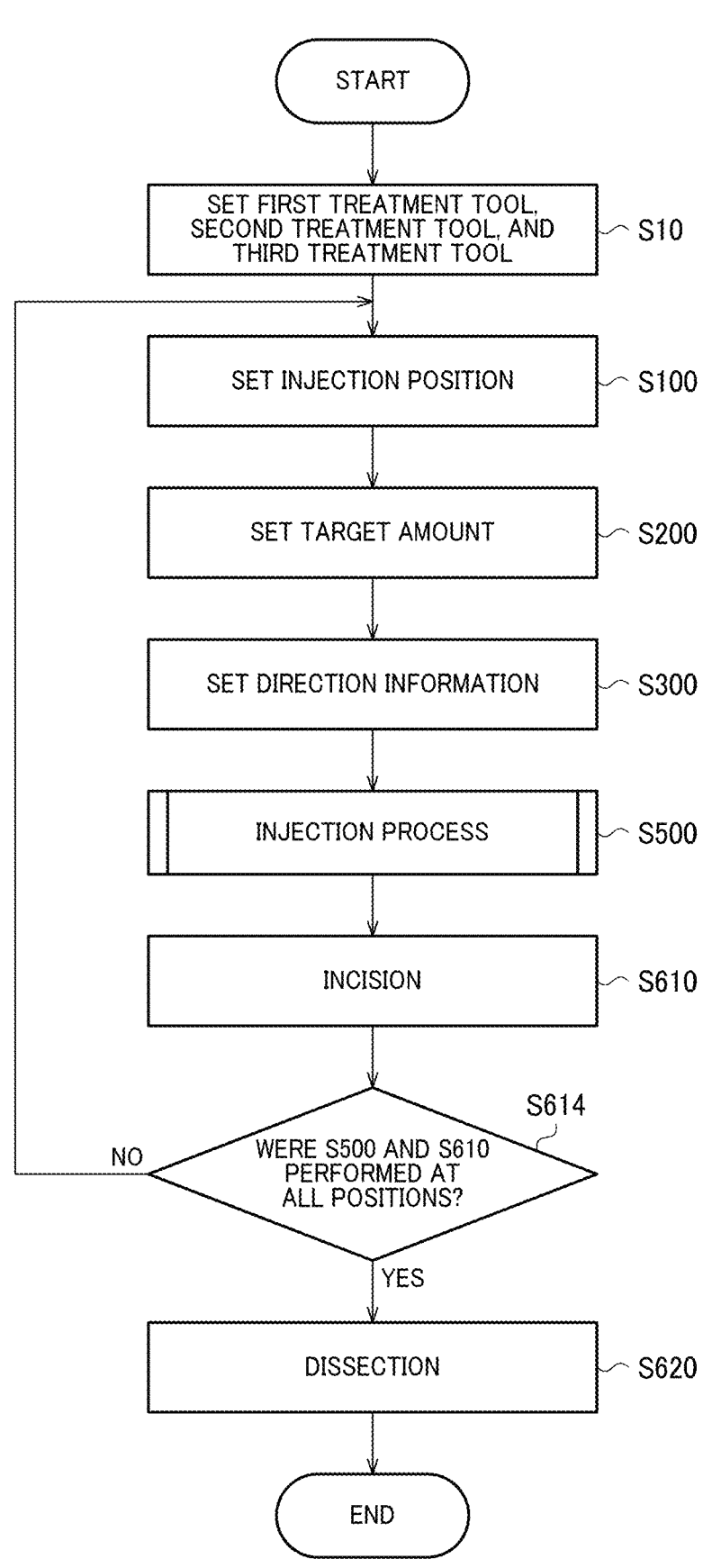
FIG. 46 is a diagram illustrating another example of the treatment flow of ESD.

Further, as modifications of the technique of the present embodiment, ESD may be performed according to the treatment flow shown in FIG. 46. The aforementioned FIG. 14 is a treatment flow where the incision (step S610) is performed after performing the injection process (step S500) to the entire area around the lesion site as the treatment target, whereas FIG. 46 is a treatment flow where the injection process (step S500) and the incision (step S610) are locally and repeatedly performed. More specifically, after setting the first treatment tool 51, the second treatment tool 52, and the third treatment tool 53 (step S10), the processor 100 decides one injection position by the aforementioned step S100. Thereafter, the processor 100 performs the step S200, the step S300, the injection process (step S500), and the incision (step S610) at one injection position thus decided. In the treatment flow of FIG. 46, since the injection is performed at one position, it is possible to perform the incision (step S610) immediately after performing the injection process (step S500). Thereafter, a user determines whether or not the injection process (step S500) and the incision (step S610) were performed at all positions (step S614). For example, the user determines, based on the endoscopic image, whether or not the lesion site subjected to the incision (step S610) is lifted from the submucosal layer. Then, when determining that the injection process (step S500) and the incision (step S610) were performed at all positions (YES in step S614), the user performs the dissection (step S620) in the same manner as in FIG. 14. On the other hand, when determining that the lesion site is not lifted from the submucosal layer, the user determines NO in the step S614 and performs the step S100 again.

Note that the first decision process (step S110) described above with reference to FIG. 31, etc., the second decision process (step S220) described above with reference to FIG. 34, etc., and the third decision process (step S330) described above with reference to FIG. 39, etc. may be applied to the treatment flow in FIG. 46. In other words, though not shown in the drawings, FIG. 46 may be a treatment flow where the first decision process (step S110), the second decision process (step S220), the third decision process (step S330), the injection process (step S500), and the incision (step S610) are repeated after the step S10.

An example treatment in the modification will be specifically described. A user sets, by the step S10, the first treatment tool 51, the second treatment tool 52, and the third treatment tool 53 (step S10) as in FIG. 2. Then, the user operates the first handle 641 while stepping on the second foot pedal 632 of the console 60, thereby operating the endoscope 40 such that the lesion site as the treatment target indicated by C41 is displayed on the display 610, as the example screen indicated by J10 in FIG. 47. Then, the user operates the touch panel 620, thereby selecting a part of the lesion site as indicated by J11. The processor 100 performs the first decision process (step S110) based on the endoscopic image within the selected range to decide the position where the injection process is to be performed (step S500). Then, the processor 100 performs the second decision process (step S220) to set the target amount of the injection fluid at the position. Then, the processor 100 performs the third decision process (step S330) to decide the direction information indicative of the insertion direction of the injection needle 516 relative to the position.

Note that the processor 100 may further perform a process of presenting the result of at least one of the first decision process (step S110), the second decision process (step S220), and the third decision process (step S330) to the user, and requesting the user to determine OK or NG. For example, in the example screen of J20 in FIG. 47, the position information regarding the position indicated by J21 where the injection process (step S500) is to be performed, the information regarding the target amount of the injection fluid indicated by J22, and the direction information regarding the insertion direction of the injection needle 516 indicated by J23 are displayed on the display 610.

Figure 47:
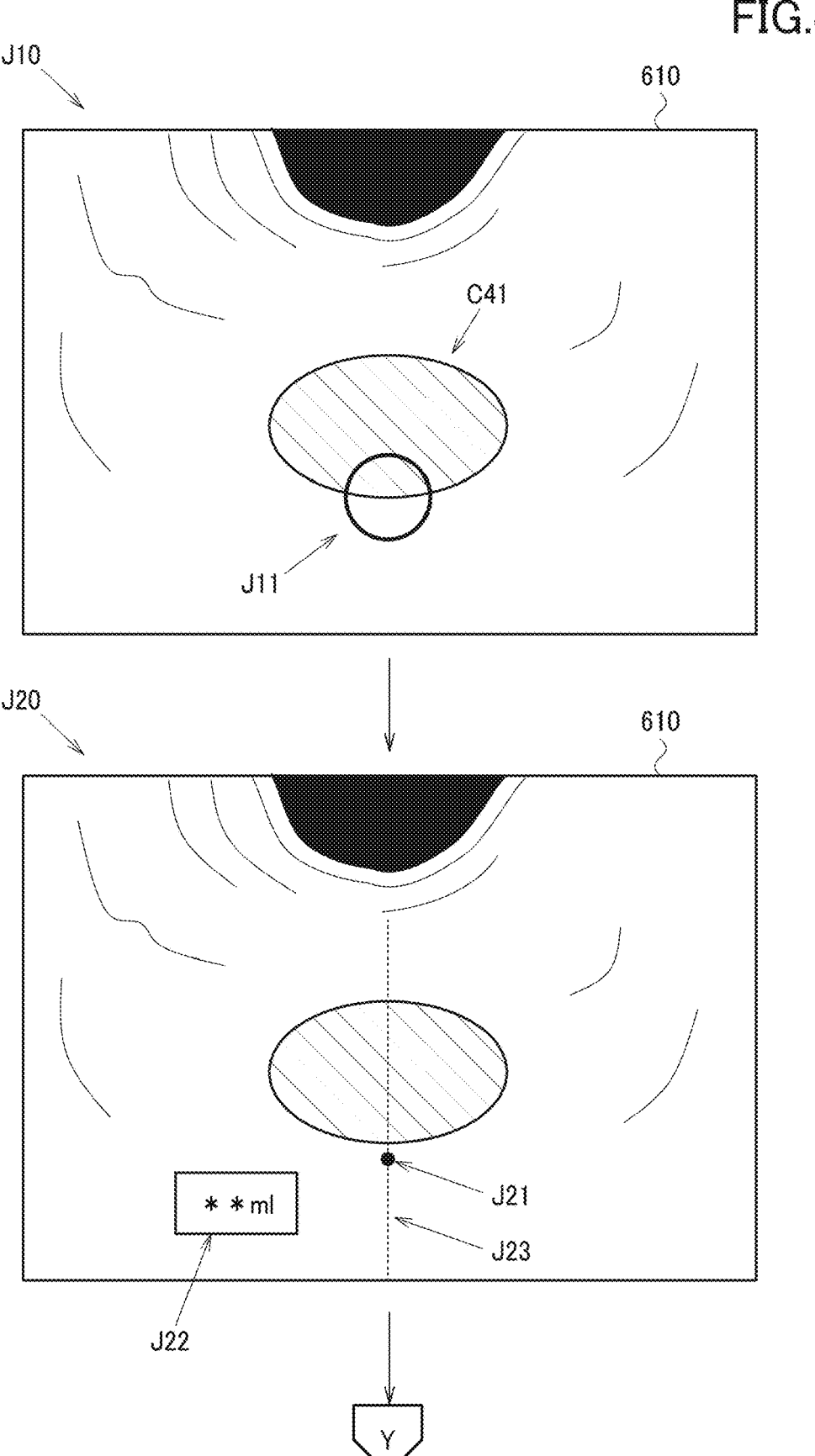
FIG. 47 is a diagram illustrating an example screen of treatment of ESD.
Figure 48:
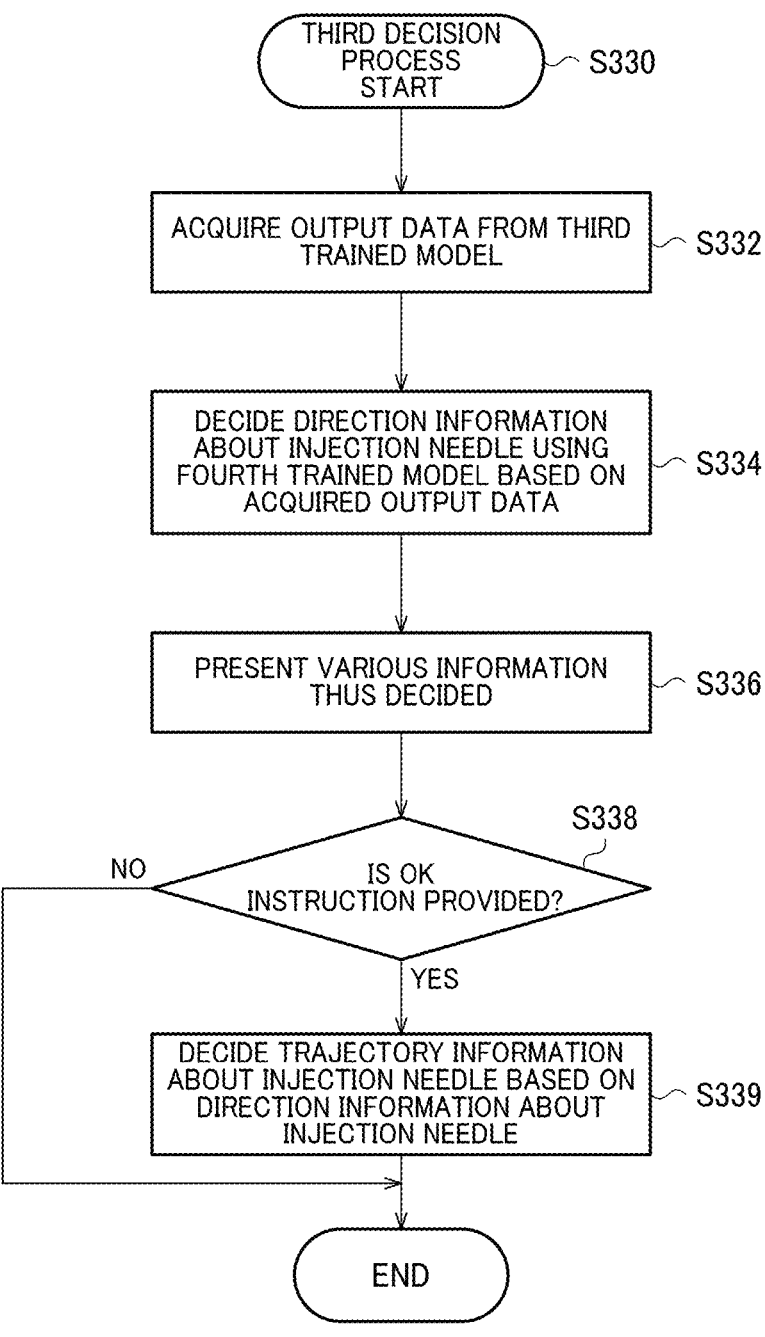
FIG. 48 is a flowchart illustrating another example processing of the third decision process.

The example screen indicated by J20 in FIG. 47 can be implemented, for example, by performing the third decision process (step S330) in accordance with the example processing shown in the flowchart of FIG. 48, and the like. The processor 100 performs a process of presenting various information thus decided (step S336) after performing the step S322 and the step S334 in the same manner as in FIG. 39. Then, it performs a process of determining whether or not an OK instruction is provided from a user (step S338). For example, the processor 100 determines OK or NG based on the control signal transmitted from a switch (not shown) of the console 60 and the like. When the OK instruction is provided from the user (YES in step S338), the processor 100 performs the aforementioned step S339. After performing the step S339, the user operates the first handle 641 while stepping on the first foot pedal 631 of the console 60, thereby marking the position indicated by J21 using the third treatment tool 53. Note that although illustration of the flow is omitted, when an NG instruction is provided from the user (NO in step S338), the flow of the third decision process (step S330) ends and then, the step S100 is performed again.

Thereafter, the user inserts the injection needle 516 into the marked position and performs the injection process (step S500). For example, the user operates the first handle 641 while stepping on the second foot pedal 632 of the console 60, thereby operating the endoscope 40 such that the distal end section of the endoscope 40 faces the position indicated by J21. Then, the user operates the first handle 641 while stepping on the third foot pedal 633 of the console 60, thereby moving forward the first medical manipulator 510 and inserting the injection needle 516 into the marked position. Alternatively, by the step S339, the drive information about the endoscope 40 and the drive information about the first medical manipulator 510 required for inserting the injection needle 516 may be programmed to automatically control the step of inserting the injection needle 516. Then, by the injection process (step S500), the step of the injection fluid entering the submucosal layer is automatically controlled. This can reduce a treatment burden on the user since the user watches the example screen indicated by J30 in FIG. 49 and observes success/failure of the injection.

Thereafter, when the injection is determined as success, the user operates the second handle 642 while stepping on the first foot pedal 631 of the console 60, thereby operating the second treatment tool 52, and also operates the third treatment tool 53 by operating the first handle 641. In this way, as shown in the example screen of J40 in FIG. 49, a desired portion is incised by the third treatment tool 53 while grasping the raised lesion site by the grasping section 522.

Figure 49:
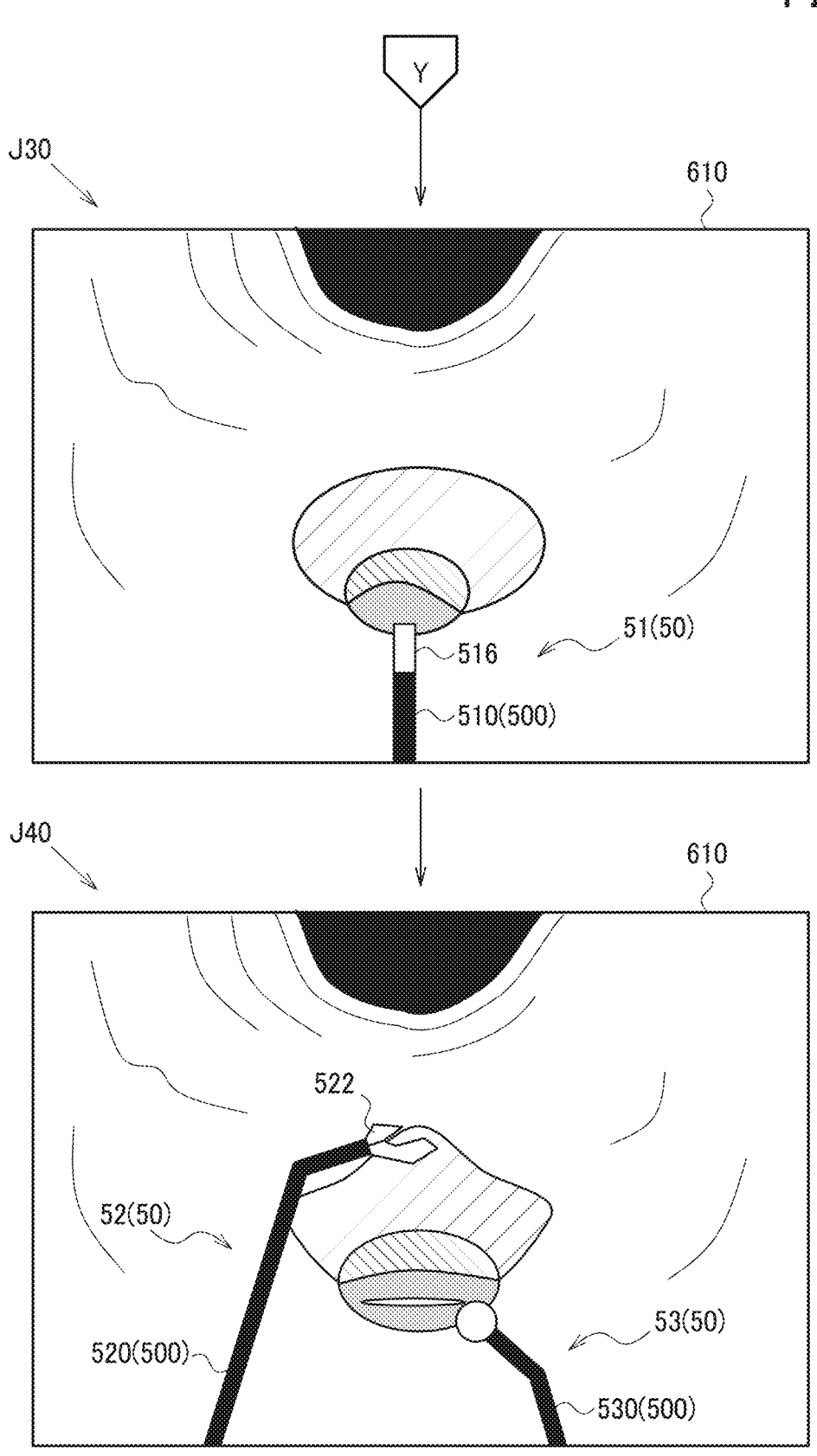
FIG. 49 is a diagram illustrating another example screen of the treatment of ESD.

In this manner, the steps shown in the example screens of FIGS. 47 and 49 are repeatedly performed. Then, once the entire lesion site is lifted from the submucosal layer, the user operates the second handle 642 while stepping on the first foot pedal 631 of the console 60, and moves backward the second medical manipulator 520 to the outside of the body while grasping the lesion site by the grasping section 522, thereby collecting the incised lesion site.

Figure 50:
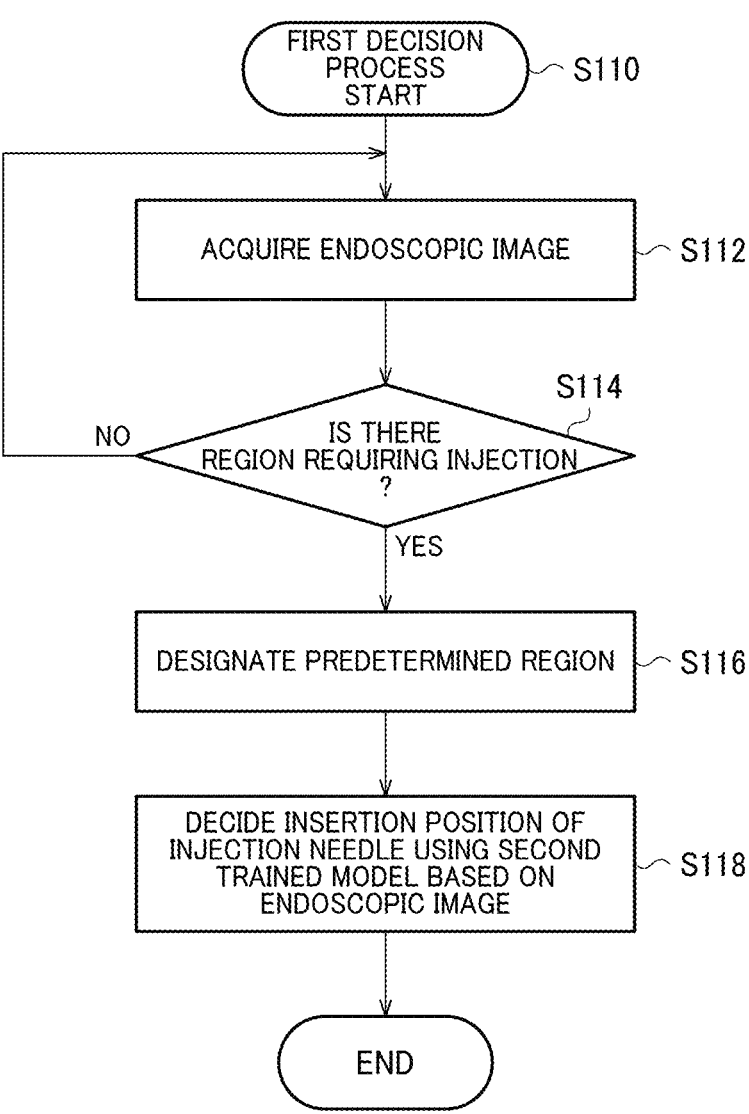
FIG. 50 is a flowchart illustrating another example processing of the first decision process.

Note that in the example screen of J10 in FIG. 47, though not limited thereto, the user operates the touch panel 620 to decide where to perform the injection. For example, the processor 100 may be configured to be able to automatically decide where to perform the injection. In this case, the first decision process (step S110) may be implemented as, for example, the example processing shown in the flowchart of FIG. 50. The processor 100 performs a process of determining whether or not there is a region requiring the injection (step S114) after performing the step S112. When determining that there is the region requiring the injection (YES in step S114), the processor 100 performs a process of designating a predetermined region (step S116). The step S116 can be implemented, for example, by the following technique. For example, the distal end section of the endoscope 40 includes a position sensor and the processor 100 acquires the position information about the distal end of the endoscope 40. Then, the processor 100 compares an endoscopic image of a luminal surface expected based on the position information with the endoscopic image of the luminal surface actually displayed, and when there is a difference, designates a corresponding region as the predetermined region with the possible lesion site. Thereafter, the processor 100 performs the aforementioned step S118.

Further, the timing of performing the step S114 may be automatically decided. For example, polling may be performed for a certain period of time after performing the injection process (step S500), and the step S114 in the first decision process (step S110) may be performed again after the elapse of the certain period of time. Alternatively, the processor 100 may determine, based on the endoscopic image being captured by a 3D camera, the timing of determining that the raised site is changed to a nearly flat shape due to the injection as the timing when the injection is completed, and perform the step S114. Alternatively, the processor 100 may determine, based on the endoscopic image, whether or not color of the submucosal layer reflects color of the pigment contained in the injection fluid, and determine that the injection is completed when color strength of the pigmen becomes less than a certain value. Alternatively, the third treatment tool 53 may include a position sensor and the processor 100 may determine the timing when the third treatment tool 53 is a certain distance away from the position of the treatment target as the timing when the injection is completed. In this manner, the step S114 is automatically performed so that the looping processes in the treatment flow of FIG. 46 are automatically performed. In other words, the injection using the first treatment tool 51 is completely automated so that the user can concentrate on the incision (step S610) and the dissection (step S620) using the second treatment tool 52 and the third treatment tool 53.

Although the embodiments to which the present disclosure is applied and the modifications thereof have been described above, the present disclosure is not limited to the embodiments and the modifications thereof, and various modifications and variations in components may be made in implementation without departing from the spirit and scope of the present disclosure. In addition, the plurality of components disclosed in the embodiments and the modifications described above may be combined as appropriate to implement the present disclosure in various ways. For example, some of all the components described in the embodiments and the modifications may be deleted. Furthermore, components in different embodiments and modifications may be combined as appropriate. Thus, various modifications and applications can be made without departing from the spirit and scope of the present disclosure. Further, any term cited with a different term having a broader meaning or the same meaning at least once in the specification and the drawings can be replaced by the different term in any place in the specification and the drawings.

The invention claimed is:

1. A surgical system comprising:

an endoscope including an imager which captures an endoscopic image;

a medical manipulator with an injection needle at a distal end section of the medical manipulator;

a drive device which controls the medical manipulator to control a position of the injection needle; and a processor, wherein the processor is configured to;

control to inject a target amount of a injection fluid into a syringe connected to the injection needle;

acquire, from the imager, the endoscopic image in which a treatment target is captured; and perform a prescribed determination using the endoscopic image to determine success/failure of injection, and control the drive device to change the position of the injection needle based on a determination result of the prescribed determination.

2. The surgical system as defined in claim 1, comprising a first trained model trained based on learning data including the endoscopic image in which the treatment target, into which the injection fluid was injected, is captured, wherein the processor:

determines, based on the endoscopic image, sufficiency of shape change of the treatment target using the first trained model; and controls the drive device to pull out the injection needle by a predetermined amount when determining that the shape change of the treatment target is insufficient.

3. The surgical system as defined in claim 1, wherein the processor:

determines success/failure of the injection in the prescribed determination, further using a control value of an injection amount of the injection fluid; and controls the drive device based on the determination result of the prescribed determination to change the position of the injection needle.

4. The surgical system as defined in claim 3, comprising a first trained model trained based on learning data including the injection amount of the injection fluid and the endoscopic image in which the treatment target, into which the injection fluid corresponding to the injection amount was injected, is captured, wherein the processor:

determines, based on the endoscopic image, sufficiency of shape change of the treatment target for the control value using the first trained model; and controls the drive device to pull out the injection needle by a predetermined amount when the shape change of the treatment target is insufficient.

5. The surgical system as defined in claim 1, comprising a force sensor that is capable of detecting resistance upon injecting the injection fluid into the treatment target, wherein the processor controls the drive device to pull out the injection needle by a predetermined amount when shape change of the treatment target is insufficient and a detection value of the force sensor is equal to or greater than a predetermined value.

6. The surgical system as defined in claim 1, comprising a position sensor that is capable of detecting a displacement amount of a plunger, wherein the processor controls the drive device to pull out the injection needle by a predetermined amount when shape change of the treatment target is insufficient and a detection value of the position sensor is less than a predetermined value.

7. The surgical system as defined in claim 1, wherein the processor decides, based on the endoscopic image, a position in the treatment target where the injection needle is to be inserted and the target amount of the injection fluid corresponding to the position where the injection needle is to be inserted.

8. The surgical system as defined in claim 7, comprising a second trained model trained based on learning data including the endoscopic image in which the treatment target is captured and position information indicative of the position where the injection needle is to be inserted, wherein the processor performs a first decision process using the second trained model to decide, based on the endoscopic image, the position where the injection needle is to be inserted.

9. The surgical system as defined in claim 8, comprising a third trained model trained based on learning data including the endoscopic image in which the treatment target is captured, the position information indicative of the position where the injection needle is to be inserted, and the target amount of the injection fluid corresponding to the position information, wherein the processor performs a second decision process using the third trained model to decide the target amount of the injection fluid at each position where the injection needle is to be inserted based on the endoscopic image and the position information decided in the first decision process.

* * * * *